US007211560B2

(12) United States Patent
Looker et al.

(10) Patent No.: US 7,211,560 B2
(45) Date of Patent: *May 1, 2007

(54) REDUCED SIDE-EFFECT HEMOGLOBIN COMPOSITIONS

(75) Inventors: Douglas L. Looker, Fort Lupton, CO (US); Izydor Z. Apostol, Boulder, CO (US); Eric A. Brucker, Evergreen, CO (US); Michael P. Doyle, Boulder, CO (US); David L. Foster, Lafayette, CO (US); Christopher B. Glascock, Louisville, CO (US); James C. Hartman, Boulder, CO (US); Geoffrey F. Lee, Boulder, CO (US); Douglas D. Lemon, Louisville, CO (US); Edwin G. Moore, Boulder, CO (US); Jane P. Richards, Longmont, CO (US); Michael R. Schick, Louisville, CO (US); Stephen P. Trimble, Boulder, CO (US); David Pereira, Apex, NC (US); Ton-That Hai, Mundelein, IL (US); Kenneth E. Burhop, Longmont, CO (US)

(73) Assignees: Baxter International, Inc., Deerfield, IL (US); Baxter Healthcare S.A., Zurich (CH)

( * ) Notice: Subject to any disclaimer, the term of this patent is extended or adjusted under 35 U.S.C. 154(b) by 360 days.

This patent is subject to a terminal disclaimer.

(21) Appl. No.: 10/747,580

(22) Filed: Dec. 29, 2003

(65) Prior Publication Data

US 2004/0259769 A1 Dec. 23, 2004

Related U.S. Application Data

(63) Continuation of application No. 09/709,914, filed on Nov. 10, 2000, now Pat. No. 6,670,323.

(60) Provisional application No. 60/165,289, filed on Nov. 12, 1999.

(51) Int. Cl.
*A61K 35/14* (2006.01)
(52) U.S. Cl. .......................... 514/6; 530/385
(58) Field of Classification Search ............ 514/6; 530/385
See application file for complete search history.

(56) References Cited

U.S. PATENT DOCUMENTS 4,001,200 A * 1/1977 Bonsen et al. ............ 530/385
4,001,401 A * 1/1977 Bonsen et al. ............ 514/6
4,703,008 A 10/1987 Lin
4,810,643 A 3/1989 Souza
4,868,119 A 9/1989 Clark et al.
5,028,588 A 7/1991 Hoffman et al.
5,032,676 A 7/1991 Deeley et al.
5,428,007 A 6/1995 Fischer et al.
5,545,727 A 8/1996 Hoffman et al.
5,585,484 A 12/1996 Acharya et al.
5,614,490 A 3/1997 Przybelski
5,631,219 A 5/1997 Rosenthal et al.
5,658,879 A 8/1997 Nho
5,679,638 A 10/1997 Teicher et al.
5,750,725 A 5/1998 Acharya et al.
5,844,088 A 12/1998 Hoffman et al.
5,844,089 A 12/1998 Hoffman et al.
5,844,090 A 12/1998 Anderson et al.
5,914,391 A 6/1999 Gerber et al.
6,017,943 A * 1/2000 Acharya et al. ............ 514/410
6,048,967 A * 4/2000 Hsia ....................... 530/385
6,670,323 B1 * 12/2003 Looker et al. ............. 514/6

FOREIGN PATENT DOCUMENTS

| EP | 0 561 245 A1 | 9/1993 |
|---|---|---|
| WO | WO 88/06161 A1 | 8/1988 |
| WO | WO 91/05795 A1 | 5/1991 |
| WO | WO 95/14038 A3 | 5/1995 |
| WO | WO 95/24213 A1 | 9/1995 |
| WO | WO 98/17289 A1 | 4/1998 |
| WO | WO 98/50430 A2 | 11/1998 |

OTHER PUBLICATIONS

Conklin, et al. "Effects of Recombinant Human Hemoglobin on Motor Functions of the Opossum Esophagus." The Journal of Pharmacology and Experimental Therapeutice, 1995, vol. 273, No. 2, pp. 762-767.

(Continued)

*Primary Examiner*—Karen Cochrane Carlson
(74) *Attorney, Agent, or Firm*—Senniger Powers

(57) ABSTRACT

The invention relates to novel hemoglobin compositions, particularly novel recombinant mutant hemoglobin compositions, which eliminate or substantially reduce 1) the creation of heart lesions, 2) gastrointestinal discomfort, 3) pressor effects, and 4) endotoxin hypersensitivity associated with the administration of extracellular hemoglobin compositions in various therapeutic applications. Applications described include treatments for anemia, head injury, hemorrhage or hypovolemia, ischemia, cachexia, sickle cell crisis and stroke; enhancing cancer treatments; stimulating hematopoiesis; improving repair of physically damaged tissues; alleviating cardiogenic shock; and shock resuscitation.

31 Claims, 18 Drawing Sheets

OTHER PUBLICATIONS

Conover, et al., "The Influence of Polyethylene Glycol Conjugation on Bovine Hemoglobin's Intrinsic Effect on the Gastrointestinal System of the Rat." Life Sciences, 1996, vol. 59, No. 22, pp. 1861-1869.

Cupane et al. "Modification of α-chain Heme Pocket Polarity by Val(E11) Thr Substitution has Different Effects on the Steric, Dynamic, and Functional Properties of Human Recombinant Hemoglobin." The Journal of Biological Chemistry, 1997, pp. 26271-26278, vol. 272, No. 42.

Deligné, P., "Quoi de neuf en 1990 en matiére de substituts de sang? I. Améliorations des solutions d' heémoglobin modifiée et hémoglobines issues de la bio-ingénierie et du génie génétique." Urgences, 1990, pp. 76-85, vol. 9.

Doyle, et al., "Oxidation of Nitrogen Oxides by Bound Dioxygen in Hemoproteins." Journal of Inorganic Biochemistry, 1981, pp. 351-358, vol. 14, Elsevier North Holland, Inc., New York.

Eich, et al., "Mechanism of NO-Induced Oxidation of Myoglobin and Hemoglobin." Biochemistry, 1996, vol. 35, pp. 6676-6983.

Feola, et al. "Clinical Trial of a Hemoglobin Based Blood Substitute in Patients with Sickle Cell Anemia". Surgery, Gynecology & Obstetrics, 1992, vol. 174, pp. 379-386.

Gould et al., "Clinical Development of Human Polymerized Hemoglobin as a Blood Substitute." World Journal of Surgery, 1996, vol. 20, No. 9, pp. 1200-1207.

Hartman et al., "Reduced Nitric Oxide Reactivity of a New Recombinant Human Hemoglobin Attenuates Gastric Dysmotility." European Journal of Pharmacology, 1998, pp. 175-178, vol. 363.

Huisman T., "Recombinant Hemoglobin Variants", Hemoblobin, 1998, pp. 99-112, vol. 22, No. 2.

Looker, et al., "A Human Recombinant Haemoglobin Designed for use as a Blood Substitute." Letters to Nature, 1992, vol. 356, pp. 258-260.

Moore, et al., "Cooperativity in the Dissociation of Nitric Oxide From Hemoglobin." The Journal of Biological Chemistry, 1976, pp. 2788-2794, vol. 251, No. 9, Waverly Press, Inc., Baltimore.

Reddy, et al., "Role of β87 Thr in the β6 Val Acceptor Site during Deoxy Hb S Polymerization." Biochemistry, 1997, vol. 36, pp. 15992-15998.

Remy et al, "Apports et perspectives des dérivé de l'hémoglobine". Schweiz Med Wochenschr, 1997, pp. 1088-1096, vol. 127.

Tsuchida, E., "Introduction: Overview and Perspectives". Artificial Red Cells: Materials, Performances and Clinical Study as Blood Substitutes, Liely, New York, NY, pp. 1-20, 1995.

Viele, et al., "Recombinant Human Hemoglobin Does not Affect Renal Function in Humans: Analysis of Safety and Pharmacokinetics." Anesthesiology, 1997, vol. 86, No. 4, pp. 848-858.

Walder, et al. "Development of Antisickling Compounds that Chemically Modify Hemoglobin S Specifically within the 2,3-Diphosphoglycerate Binding Site". J. Mol. Biol., 1980, vol. 141, pp. 195-216, Academic Press, Inc. (London) Ltd.

* cited by examiner

REDUCED SIDE-EFFECT HEMOGLOBIN COMPOSITIONS

CROSS-REFERENCE TO RELATED APPLICATION

This application claims priority from prior application Ser. No. 09/709,914 filed Nov. 10, 2000 now U.S. Pat. No. 6,670,323 and provisional application Ser. No. 60/165,289 filed Nov. 12, 1999, which are both hereby incorporated by reference in their entirety.

FIELD OF THE INVENTION

The invention relates to novel hemoglobin compositions, particularly novel recombinant mutant hemoglobin compositions, which eliminate or substantially reduce 1) the creation of heart lesions, 2) gastrointestinal discomfort, 3) pressor effects, and 4) endotoxin hypersensitivity associated with the administration of extracellular hemoglobin compositions in various therapeutic applications. Applications described include use as a blood substitute, volume expander and/or oxygen carrier in various therapeutic treatments.

BACKGROUND OF THE INVENTION

Hemoglobin (Hb) is the oxygen-carrying protein of blood, comprised of four associated polypeptide chains that bear prosthetic groups known as hemes. About 92% of adult human hemoglobin is composed of two alpha globin subunits ($\alpha 1$, $\alpha 2$) and two beta globin subunits ($\beta 1$, $\beta 2$) that associate noncovalently to form $\alpha 2\beta 2$, commonly known as hemoglobin $A_0$ (WO 93/09143). However, adult hemoglobin may also comprise delta globin subunits. The delta globin subunit replaces beta globin and pairs with alpha globin as alpha2delta2 to form hemoglobin A2. In addition to the globin subunits of adult hemoglobin, a number of hemoglobin subunits are expressed in nature only during embryonic and fetal development including, gamma globin, zeta globin, and epsilon globin. To form embryonic or fetal hemoglobin, zeta globin may replace alpha globin and epsilon and gamma globin may replace beta globin (e.g. to form tetrameric hemoglobin such as alpha2epsilon2, alpha2gamma2, zeta2epsilon2, and zeta2gamma2). Embryonic hemoglobin confers a biological advantage to the developing fetus because it generally has a higher oxygen affinity relative to adult hemoglobin and thus, facilitates fetal oxygen uptake from the maternal blood stream. The structure of hemoglobin is well known and described in Bunn & Forget, eds., *Hemoglobin: Molecular Genetic and Clinical Aspects* (W.B. Saunders Co., Philadelphia, Pa.: 1986) and Fermi & Perutz "Hemoglobin and Myoglobin," in Phillips and Richards, *Atlas of Molecular Structures in Biology* (Clarendon Press: 1981).

Expression of various recombinant hemoglobins containing naturally-occurring and non-naturally occurring globin mutants has been achieved. Such methods include the expression of individual globins in recombinant cells, as described, for example, in U.S. Pat. No. 5,028,588, and co-expression of alpha and beta globins in the same cell, as described in U.S. Pat. No. 5,545,727. In addition, di-alpha globin expression, wherein two alpha globins are joined with a short polypeptide linker through genetic fusion and are later coupled with two beta globins to produce a pseudotetrameric hemoglobin molecule, has been described in U.S. Pat. No. 5,545,727 and Looker et al., *Nature* 356:258–260 (1992). Other modified recombinant hemoglobins are disclosed, e.g., in U.S. Pat. No. 5,844,090.

Solutions of extracellular hemoglobin have been demonstrated to have many therapeutic uses. U.S. Pat. Nos. 5,658,879 and 5,659,638 describe the administration of stroma-free purified wildtype hemoglobin to cancer patients in order to enhance the effects of chemotherapy or radiation therapy. U.S. Pat. No. 5,614,490 describes the use of stroma-free diaspirin crosslinked hemoglobin to increase the perfusion of tissues to treat stroke and ischemia, and to treat hypovolemic, cardiogenic, and septic shock. U.S. Pat. No. 5,428,007 describes the use of recombinant mutant hemoglobin with altered oxygen affinity to increase tissue oxygenation in order to treat burn victims. U.S. Pat. No. 5,631,219 teaches the use of recombinant mutant hemoglobin with altered oxygen affinity to treat anemias, cytopenias, and cachexia, and to stimulate hematopoiesis. And, WO 98/17289 describes the use of stroma-free diaspirin crosslinked hemoglobin to treat head injuries in mammals. The use of crosslinked oxyhemoglobin to treat sickle cell disease is described by Walder et al., *J. Mol. Bio.*, vol. 141, 195–216 (1980).

Nitric oxide acts as a chemical messenger in the control of many important processes in vivo, including neurotransmission, inflammation, platelet aggregation, and regulation of gastrointestinal and vascular smooth muscle tone. The biological actions of nitric oxide are mediated by binding to and activation of soluble guanylyl cyclase, which initiates a biochemical cascade resulting in a variety of tissue-specific responses (Feldman et al., *Chem. Eng. News* December 26–38 (1993)).

Elucidating the functions of nitric oxide has depended largely on inhibition of the nitric oxide-generating enzyme, nitric oxide synthase. Most conclusions about the effects of cell-free hemoglobin have been drawn based on experiments involving nitric oxide synthase inhibitors and/or nitric oxide donors. While the rapid, high-affinity binding of nitric oxide to deoxyhemoglobin is well known, the importance of the oxidative reaction between nitric oxide and oxyhemoglobin is not as widely appreciated. In this reaction, the nitric oxide molecule does not bind to the heme, but reacts directly with the bound oxygen of the oxyhemoglobin complex to form methemoglobin and nitrate (Doyle et al., *J. Inorg. Biochem.* 14: 351–358 (1981)). The chemistry is analogous to the rapid reaction of nitric oxide with free superoxide in solution (Huie et al., *Free Rad. Res. Comms.* 18: 195–199 (1993)). Both the heme iron and nitric oxide become oxidized by the bound oxygen atoms, and the reaction occurs so rapidly that no replacement of oxygen by nitric oxide is observed (Eich et al., infra.).

Since nitric oxide is produced and consumed on a continuous basis, there is a natural turnover of nitric oxide in vivo. When a cell-free hemoglobin is administered, the balance between nitric oxide production and consumption is altered by reactions with hemoglobin. The most relevant parameter for nitric oxide scavenging by hemoglobin is the rate of reaction with nitric oxide, not the position of the hemoglobin allosteric (R/T) equilibrium. The oxidative reaction is irreversible, and nitric oxide binding to deoxyhemoglobin is effectively irreversible on physiologic timescales since the half-life for dissociation of nitrosylhemoglobin is 5–6 hours (Moore et al., *J. Biol. Chem.* 251: 2788–2794 (1976).

When nitric oxide molecules react with oxyhemoglobin or deoxyhemoglobin, they are eliminated from the pool of signal molecules. Once sufficient nitric oxide molecules are eliminated, it is believed, certain adverse conditions are created. For example, hemoglobin can bind nitric oxide causing the prevention of vascular relaxation and potentially leading to hypertension that is sometimes observed after administration of certain extracellular hemoglobin solutions. In addition, the ability of nitric oxide to oxidize oxyhemoglobin producing nitrate and methemoglobin could also lower free concentrations of nitric oxide and lead to hypertension.

Nitric oxide is also needed to mediate certain inflammatory responses. For example, nitric oxide produced by the endothelium inhibits platelet aggregation. Consequently, as nitric oxide is bound by cell-free hemoglobin, platelet aggregation may be increased. As platelets aggregate, they release potent vasoconstrictor compounds such as thromboxane $A_2$ and serotinin. These compounds may act synergistically with the reduced nitric oxide levels caused by hemoglobin scavenging resulting in significant vasoconstriction. In addition to inhibiting platelet aggregation, nitric oxide also inhibits neutrophil attachment to cell walls, which in turn may lead to cell wall damage.

Several undesirable side effects have been observed by applicants upon administering solutions of extracellular wild-type human hemoglobin to test subjects. Applicants' experimental results in sensitive test animals, as described in detail below, demonstrate that extracellular hemoglobin compositions such as those including wild-type adult human hemoglobin molecules administered at therapeutic dosages result in the formation of myocardial necrosis in heart tissue. While not being bound to a particular theory, applicants believe that there is a direct correlation between nitric oxide (NO) scavenging by these extracellular hemoglobin molecules and the incidence of myocardial necrosis in treated animals. Applicants found that administration of nitric oxide synthase (NOS) inhibiting drugs to test animals generates heart lesions similar to those observed with the administration of extracellular hemoglobin compositions.

In addition, several other undesirable side effects have been observed by others with the use of previously described hemoglobins. Mild hypertension has sometimes been observed following administration of certain extracellular hemoglobin solutions. It is believed by many that the hypertension is due to depletion of nitric oxide in the wall of the vasculature, based in part on the known high affinity of deoxyhemoglobin for nitric oxide (Schultz et al., *J. Lab. Clin. Med.* 122:301–308 (1993); Thompson et al., *J. Appl. Physiol.* 77:2348–2354 (1994); Rooney et al., *Anesthesiology* 79:60–72 (1993)). Extravasation of the hemoglobin into endothelial cells or interstitial spaces may cause significant consumption of nitric oxide (Gould et al., *World J. Surg.* 20: 1200–1207 (1996)). A recent study also suggests that the oxidative reaction of nitric oxide with the bound oxygen of oxyhemoglobin may be of greater significance in vivo than simple binding to the iron atom as reported in Eich et al., *Biochemistry* 35: 6976–6983 (1996). Eich et al. showed that steric hindrance introduced by substitution of amino acids adjacent to bound oxygen can markedly lower the rate of nitric oxide-induced oxidation.

Transient mild to moderate gastrointestinal effects are another side effect that has been commonly observed with the administration of extracellular hemoglobin compositions (Tsuchida, et al., introduction, *Artificial Red Cells: Materials, Performances and Clinical Study as Blood Substitutes.* Liely, New Your, N.Y., p. 1–20 (1995), and Viele, et al., *Anesthesiology*, 86: 848–58 (1997)). These effects include upper gastrointestinal discomfort including mid-epigastric discomfort, abdominal pain and/or dyspepsia and/or lower gastrointestinal discomfort including lower abdominal pain, flatulence and/or diarrhea. The gastrointestinal events typically develop one to three hours post infusion, last from one to several hours, and wax and wane over time. Nitric oxide is known to be an important modulator of the proper function of the smooth muscle tissue which regulates gastrointestinal contractility. Observed gastrointestinal effects are thus thought to be due in part to gastrointestinal dysmotility caused by hemoglobin reactivity with nitric oxide (Conklin, et al., *J. Pharmacol. Exp.* 273: 762–67 (1995), and Conover, et al., *Life Sci.* 59: 1861–69 (1995).).

In addition, endotoxin hypersensitivity has also been observed in animals which are co-administered extracellular hemoglobin solutions and low doses of lipopolysaccharide. These animals usually die from septic shock within 48 hours of co-administration.

Thus, the need exists for a method of eliminating or substantially reducing the creation of heart lesions in mammals treated with the extracellular hemoglobin used in these applications, as well as other deleterious side effects, such as pressor effects or gastric discomfort, associated with such use. Accordingly, a need exists for hemoglobin compositions which eliminate or substantially reduce the occurrence of heart lesions and other adverse conditions, while still functioning as an effective oxygen carrying agent.

One problem which has been encountered in storing purified extracellular hemoglobin solutions for therapeutic use is the formation of hemoglobin aggregates and precipitates over time. Addition of antioxidants, such as n-acetylcysteine, dihydrolipoic acid, or ascorbate, is known to prevent precipitate formation. However, chemical-free methods of preventing hemoglobin aggregate formation are preferred to simplify regulatory approval of the hemoglobin solutions.

SUMMARY OF THE INVENTION

The invention relates to hemoglobins which reduce (reduced lesion) or eliminate heart lesions (lesion free) when administered as a therapeutic agent. These hemoglobins are preferably recombinantly produced mutant hemoglobins, which may be chemically crosslinked. Therefore, in one aspect, the invention is directed to pharmaceutical compositions comprising recombinant hemoglobins which cause reduced or no heart lesions in a suitable pharmaceutical carrier.

The invention also relates to hemoglobins with moderately reduced (reduced gastrointestinal effect) or greatly reduced deleterious gastrointestinal effects (low gastrointestinal effect) when administered as a therapeutic agent. These hemoglobins are preferably recombinantly produced mutant hemoglobins, which may be chemically crosslinked. Therefore, in another aspect, the invention is directed to pharmaceutical compositions comprising recombinant hemoglobins which cause moderately or greatly reduced gastrointestinal effects in a suitable pharmaceutical carrier.

The invention also relates to hemoglobins with moderately reduced (reduced pressor effect) or greatly reduced pressor effects (low pressor effect) when administered as a therapeutic agent. These hemoglobins are preferably recombinantly produced mutant hemoglobins, which may be chemically crosslinked. Therefore, in another aspect, the invention is directed to pharmaceutical compositions comprising recombinant hemoglobins which cause moderately or greatly reduced pressor effects in a suitable pharmaceutical carrier.

The invention also relates to hemoglobins which cause reduced endotoxin hypersensitivity effects (reduced endotoxin effect) when administered as a therapeutic agent. These hemoglobins are preferably recombinantly produced mutant hemoglobins, which may be chemically crosslinked. Therefore, in another aspect, the invention is directed to pharmaceutical compositions comprising recombinant hemoglobins which cause reduced endotoxin hypersensitivity effects in a suitable pharmaceutical carrier.

The invention also relates to hemoglobins which have any combination or permutation of the above biological characteristics, in either a reduced or low to zero degree. Therefore, in another aspect, the invention is directed to pharmaceutical compositions comprising recombinant hemoglobins which cause a combination of the above effects in a suitable pharmaceutical carrier.

The present invention is also directed to the use of any of the above hemoglobins in a physiologically acceptable solution as an oxygen carrying whole blood substitute.

The present invention is also directed to the use of any of the above hemoglobins to treat hypovolemia, and to resuscitate a mammal suffering from hemorrhagic or cardiogenic shock.

Another aspect of the present invention is the use of any of the above hemoglobins to increase tissue perfusion in order to treat ischemia or stroke, and to increase oxygenation of tissues which have been subject to physical damage, such as wounds and burns.

Another aspect of the present invention is the use of any of the above hemoglobins to treat anemia and to stimulate hematopoiesis.

Another aspect of the present invention is the use of any of the above hemoglobins to treat head injury in a mammal.

Another aspect of the invention is directed to the administration of a cancer therapy enhancing amount of any of the above hemoglobins to a patient undergoing radiation or chemotherapy in order to enhance the tumor-reducing effects of that therapy.

Yet another aspect of the present invention is directed to the use of any of the above hemoglobins to treat sickle cell anemia patients, in particular such patients undergoing vaso-occlusive crisis.

In addition to hemoglobin compositions with novel biological properties, as described above, the present invention is also directed to novel recombinant mutant hemoglobins which demonstrate a reduced rate of reactivity with nitric oxide. Specifically, the invention is directed to recombinant mutant hemoglobins comprising a mutation or mutations in the α subunit corresponding to B10(Leu→Tyr); B10(Leu→Trp)+E11(Val→Phe)+G8(Leu→Ala); B10(Leu→Trp)+E7(His→Gln)+E11(Val→Met)+G8(Leu→Val); B10(Leu→Trp)+E7(His→Gln)+E11(Val→Phe)+G8(Leu→Val); B10(Leu→Trp)+E7(His→Gln)+E11(Val→Leu)+G8(Leu→Val); B10(Leu→Phe)+E7(His→Gln)+E11(Val→Met)+G8(Leu→Phe); B10(Leu→Phe)+E7(His→Gln)+E11(Val→Met)+G8(Leu→Met); B10(Leu→Phe)+E7(His→Gln)+E11(Val→Met)+G8(Leu→Ile); or B9(Ala→Phe). The invention is also directed to recombinant mutant hemoglobins comprising a mutation or mutations in the β subunit corresponding to B9(Ala→Leu)+E11(Val→Met)+G8(Leu→Trp); B9(Ala→Leu)+E11(Val→Leu)+G8(Leu→Trp); B9(Ala→Leu)+E11(Val→Leu); B9(Ala→Phe)+E11(Val→Leu); B9(Ala→Trp)+E11(Val→Leu); B9(Ala→Phe); B9(Ala→Trp); B9(Ala→Leu); B9(Ala→Met); E11(Val→Met); B10(Leu→Phe)+B14(Leu→Phe); B9(Ala→Leu)+G8(Leu→Trp); B9(Ala→Trp)+G8(Leu→Phe); B9(Ala→Phe)+G8(Leu→Trp); B9(Ala→Trp)+G8(Leu→Trp); B10(Leu→Ala)+E7(His→Phe)+G8(Leu→Trp); or E11(Val→Trp)+G8(Leu→Trp). In addition, the invention is also directed to recombinant hemoglobin mutants comprising a combination of any of the preceding mutations in both α and β subunits.

In addition, the present invention is also directed towards recombinant mutant hemoglobins which exhibit decreased aggregate formation when stored in solution in deoxygenated form for prolonged periods of time, and which do not comprise the sickle cell mutation, β6 Glu→Val. Preferably, such hemoglobins comprise a mutation to a hydrophilic or bulky amino acid in the β subunit at the 87 threonine, and comprise the native amino acid β6 Glu. More preferably, such hemoglobins comprise a mutation chosen from the group consisting of β87 Thr→Asp, Glu, Arg, Lys, His, Tyr, Gln, or Trp. Even more preferably, such hemoglobins comprise a mutation chosen from the group consisting of β87 Thr→Asp, Gln, Glu, Arg, Lys, or His. Most preferably, such hemoglobins comprise the mutation β87 Thr→Gln.

DESCRIPTION OF THE PREFERRED EMBODIMENT

Figure 1:
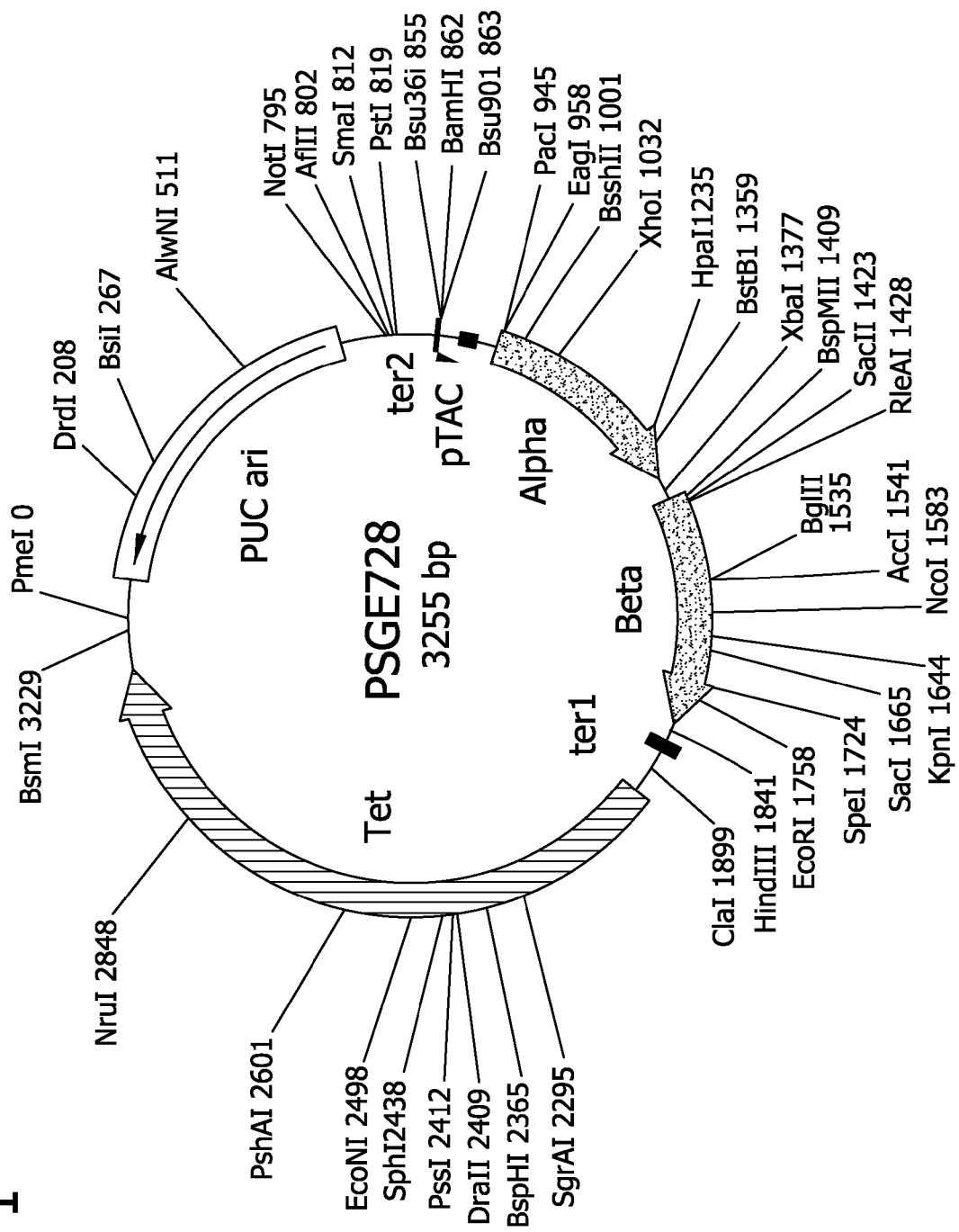
FIG. 1 shows the plasmid pSGE728 which was used for certain mutagenesis and expression experiments.

Various terms are used herein in describing this aspect of the present invention. Unless defined otherwise, all technical and scientific terms used herein have the same meaning as commonly understood by those skilled in the art.

"Affinity" refers to the equilibrium binding of a ligand to hemoglobin, and is described by the thermodynamic equilibrium constant, Keq. Keq is equal to the ratio of the ligand association rate constant and the hemoglobin-ligand dissociation rate constant, and thus changes in association rate constant, dissociation rate constant or both can lead to changes in ligand affinity. When a hemoglobin molecule exhibits cooperativity, affinity is also affected by the R/T equilibrium and differences between the Keq of the individual subunits of the hemoglobin molecule.

As used herein, an "alpha globin" has at least about 75% sequence identity with native human alpha globin. However, a polypeptide of lesser sequence identity may still be considered substantially homologous with native human alpha globin, and thus may be an alpha globin, if it has a greater sequence identity than would be expected from chance and also has the characteristic higher structure of native human alpha globin and similar biological activity. Likewise, a "beta globin" has at least about 75% sequence identity with native human beta globin. However, a polypeptide of lesser sequence identity may still be considered substantially homologous with native human beta globin, and thus may be a beta globin, if it has a greater sequence identity than would be expected from chance and also has the characteristic higher structure of native human beta globin and similar biological activity. Additionally, a "delta globin" has at least about 75% sequence identity with native human delta globin. However, a polypeptide of lesser sequence identity may still be considered substantially homologous with native human delta globin and thus may be a delta globin, if it has a greater sequence identity than would be expected from chance and also has characteristic higher structure of native human delta globin and similar biological activity. Equally, an "epsilon globin" has at least about 75% sequence identity with native human epsilon globin. However, a polypeptide of lesser sequence identity may still be considered substantially homologous with native human epsilon globin, and thus may be an epsilon globin, if it has a greater sequence identity than would be expected from chance and also has the characteristic higher structure of native human epsilon globin and similar biological activity. Likewise, a "gamma globin" has at least about 75% sequence identity with native human gamma globin. However, a polypeptide of lesser sequence identity may still be considered substantially homologous with native human gamma globin, and thus may be a gamma globin, if it has a greater sequence identity than would be expected from chance and also has the characteristic higher structure of native human gamma globin and similar biological activity. Additionally, a "zeta globin" has at least about 75% sequence identity with native human zeta globin. However, a polypeptide of lesser sequence identity may still be considered substantially homologous with native human zeta globin, and thus may be an zeta globin, if it has a greater sequence identity than would be expected from chance and also has the characteristic higher structure of native human zeta globin and similar biological activity.

"Altered affinity" means the affinity of a recombinant hemoglobin for a gaseous ligand that is at least 10% different from the affinity of naturally occurring human hemoglobin for that same gaseous ligand under the same measurement conditions.

"Cancer therapy" is defined, for the purposes of this invention, as any treatment designed to kill tumor cells in a patient. Cancer therapies include radiation and chemotherapies.

A "cytopenic condition" or "cytopenia" is defined as a clinically significant reduction in the numbers, volume, functionality, or distribution of any circulating blood cell type. Cytopenia is intended to embrace at least anemia, thrombocytopenia, neutropenia, and leukopenia.

"Decreased aggregate formation" is defined as the formation of not more than two milligrams precipitate per gram of total hemoglobin in an approximately 10 g/dl deoxyhemoglobin solution, with an initial methemoglobin content of about 10%, stored at 25° C. for at least three months.

"Deoxyhemoglobin" or "unliganded hemoglobin" means any hemoglobin to which no exogenous ligand is bound to the alpha globin, the beta globin, and/or any functional heme prosthetic group. "Liganded hemoglobin" means hemoglobin to which an exogenous ligand is bound at the heme groups. Common preferred ligands include, but are not limited to oxygen, carbon monoxide, nitric oxide and the like.

"Distal heme pocket" means that portion of the heme pocket above the plane of the heme that contains the free coordination site of the iron where exogenous ligand molecules can combine reversibly with the iron atom and which contains such residues as histidine E7 and valine E11. Likewise, the "proximal heme pocket" is described by those residues below the plane of the heme and contains such residues as the proximal histidine at position F8.

"Embryonic hemoglobin" means a hemoglobin with at least 1 subunit that is expressed in nature predominantly only during embryonic development, such as gamma globin, zeta globin, or epsilon globin.

"Focal heart lesions," as used herein, refers to the number of individual lesion areas in a section of the rhesus monkey heart examined (usually about 1.0 cm×1.5 cm×4–6 µm). When three or fewer heart lesions are present per section examined, the heart lesion is described as focal.

"Head injury" is defined, for the purposes of this invention, as any injury to the head (including the brain), which is the result of any exterior force being applied to the head, such as a physical force. Examples of head injury would be a contusion or wounding of the brain from an accident. Head injury usually results in an increase in intracranial pressure and a decrease in cerebral perfusion pressure.

"Hematopoiesis," for the purposes of this invention, is a generic term for the process of formation and development of blood cells from progenitor cells as well as formation of progenitor cells of those blood cells. Blood cells include but are not limited to erythrocytes, reticulocytes, monocytes, neutrophils, megakaryotes, eosinophils, basophils, B-cells, macrophages, granulocytes, mast cells, thrombocytes, and leukocytes. Progenitor cells include, but are not limited to burst forming units—erythroid (BFU-E), colony forming units—erythroid (CFU-E), colony forming units—megakaryote (CFU-Meg), colony forming units—granulocyte-macrophage (CFU-GM), colony forming units—macrophage (CFU-M), colony forming units—granulocyte (CFU-G), colony forming units—granulocyte, erythroid, macrophage, megakaryote (CFU-GEMM), colony forming units—monocyte (CFU-M), colony forming units—eosinophil (CFU-Eo), colony forming units—spleen (CFU-S), colony forming units—basophil (CFU-B), pluripotent stem cells, totipotent stem cells, myeloid stem cells, and lymphoid stem cells. "Erythropoiesis" for the purposes of the appended claims is defined as that part of the hematopoietic pathway that leads to the formation of red blood cells. "Thrombopoiesis" for the purposes of the appended claims is defined as that part of the hematopoietic pathway that leads to the formation of thrombocytes. "Leukopoiesis" for the purposes of the appended claims is defined as that part of the hematopoietic pathway that leads to the formation of leukocytes. The process for the formation of other cells of the blood circulation are analogously defined and are distinguished by the use of the suffix "poiesis" or "poietic". Hematopoiesis may be measured by an increase in progenitor cells as shown by an increase in total number of cells per given volume. For example, in the blood circulation, an increase can mean an increase in the total number of cells, the size of individual cells or, specifically for erythroid cells, the hemoglobin content of individual cells. For example, for erythroid cells, this increase is at least 6% over the baseline level (the size or concentration of the cell type of interest measured prior to treatment), more preferably 10% above the baseline level, still more preferably 20% above the baseline level, most preferably to essentially normal levels in vivo.

"Heme pocket" means that pocket formed around the heme prosthetic group of each globin subunit described by the surrounding residues and is meant to include residues within about 6 Å of the heme moiety.

"Hemoglobin," as used in this application, refers generally to a molecule based on $\alpha_2\beta_2$ wild-type hemoglobin which may include any of several genetic and chemical modifications, such as point mutations in the α or β subunits, fusion of two or more α or β subunits into a single polypeptide chain (i.e., di-α or di-di α hemoglobins), and intra or inter-molecular chemical crosslinking. It may also refer to a molecule wherein an alpha and/or beta subunit is replaced with a delta globin, an epsilon globin, a gamma globin, and/or a zeta globin subunit.

For the purposes of this invention, unless indicated otherwise by context, "naturally occurring human hemoglobin," "native hemoglobin," "wild type hemoglobin" or "conventional hemoglobin" refer to human hemoglobin $A_0$ whose alpha and beta globin amino acid sequences are given in FIG. 1 of U.S. Pat. No. 5,028,588. Note that it is conventional to identify the helical segments of the globin subunits by letters, for example, the proximal histidine of the alpha chain or the beta chain is termed F8 (residue 8 of helix F). The non-helical segments are identified by letter pairs, indicating which helical segments they connect, for example, non-helical segment BC connects helix B and helix C. The helical notation and corresponding amino acids for alpha and beta globin are shown in Table 4 of U.S. Pat. No. 5,028,588.

"Hypovolemia" is defined, for the purposes of this invention, as an abnormally decreased volume of circulating fluid (blood or plasma) in the body. This condition may result from "hemorrhage," or the escape of blood from the vessels.

"Ischemia" is defined, for the purposes of this invention, as a deficiency of blood in a part of the body, usually caused by a functional constriction or actual obstruction of a blood vessel.

"Lesion free" hemoglobin, as used herein, is defined as a hemoglobin which, upon administration at a dose of 2000 mg/kg to rhesus monkeys (*Macaca mulatta*) under the conditions described in Example 10, causes no heart lesions in 95% of test subjects.

"Low gastrointestinal effect" hemoglobin, as used herein, is defined as a hemoglobin which, upon administration at a dose of 1500 mg/kg to conscious Sprague Dawley rats under the conditions described in Example 11, causes a decrease in gastric emptying of less than 10% as compared to the administration of 1500 mg/kg of human serum albumin.

"Low pressor effect" hemoglobin, as used herein, is defined as a hemoglobin which, upon administration at a dose of 2000 mg/kg to Sprague Dawley rats under the conditions described in Example 12, causes an increase in mean arterial pressure of less than 10 mm Hg.

"Methemoglobin" or "oxidized hemoglobin" means any hemoglobin in which the iron has been oxidized to the ferric state.

A "mild heart lesion," as used herein, is defined as an area of myocardial necrosis of six heart muscle cells to about fifty heart muscle cells across.

A "minimal heart lesion," as used herein, is defined as an area of myocardial necrosis no more than five heart muscle cells across.

"Multifocal heart lesions," as used herein, refers to the number of individual lesion areas in a section of the rhesus monkey heart examined (usually about 1.0 cm×1.5 cm×4–6 μm). When more than three heart lesions are present per section examined, the heart lesion is described as multifocal.

"Mutant hemoglobin" means hemoglobin comprising alpha-like globin proteins and/or beta-like globin proteins, whether monomeric or polymeric, whose amino acid sequence has at least one mutation from the wild-type hemoglobin for any particular species, such as human, bovine or porcine. Mutant hemoglobins also include those hemoglobins containing a genetically fused dimeric polypeptide, such as the di-α (α-gly-α) polypeptide. Such alterations to the hemoglobin molecule are fully described in U.S. Pat. No. 5,844,089. In addition, the term "hemoglobin-like protein" is used to describe hemoglobins comprising globin subunits with mutations or genetically fused globin subunits. "Globin-like" polypeptide, protein, or subunit, similarly refers to a mutant or genetically fused hemoglobin globin subunit.

"Mutations" are substitutions, deletions or additions of one or more amino acids to the amino acid sequence that constitutes wild-type human hemoglobin or that of other species.

"Myocardial necrosis" is defined as at least minimal to moderate myofiber necrosis (cell death) with a focal to multifocal distribution and accompanied by a mononuclear inflammatory infiltrate (as leucocytes or macrophages) at some of the sites.

"Oxidation" means an increase in the oxidation state of the iron in the heme of any or all of the subunits making up the hemoglobin tetramer from the ferrous ($Fe^{+2}$) to the ferric form ($Fe^{+3}$). Autooxidation is a slow oxidation that occurs spontaneously in the presence of oxygen. However, oxidation can be accelerated greatly by the presence of other exogenous oxidizing agents, most notably nitric oxide and hydrogen peroxide.

"Oxyhemoglobin" means hemoglobin in which an oxygen molecule is bound to the functional oxygen binding sites in each subunit.

"Recombinant hemoglobin" means hemoglobin, whether native or mutant, comprising alpha-like globin proteins and/or beta-like globin proteins, at least one of which is obtained by expression of a globin gene carried by a recombinant DNA molecule in a cell other than the cell in which that hemoglobin gene and/or hemoglobin protein is naturally found. In other words, the hemoglobin gene is heterologous to the host in which it is expressed. For example, the expression of any human hemoglobin gene in any cell other than a human red blood cell would be considered to be a recombinant hemoglobin. Also, for example, all non-naturally occurring hemoglobins are recombinant hemoglobins.

"Perfusion" is defined, for the purposes of this invention, as the passage of fluid through the vessels of an organ or tissue.

"Physical tissue damage" is defined, for the purposes of this invention, as an injury to the tissues of a body resulting from applied force, extreme thermal change, or the application of corrosive chemical agents. Examples of physical tissue damage include wounds, contusions, burns, and frostbite.

"R-state hemoglobin" is the high affinity state of hemoglobin and is the dominant form of hemoglobin when exogenous ligands are bound to the heme prosthetic groups. The ligand is typically oxygen, thus this state is known as the "oxy" or "R" (for relaxed) state.

"Reduced endotoxin effect" hemoglobin, as used herein, is defined as a hemoglobin which, upon administration at a dose of 1000 mg/kg to mice with co-administration of 5 mg/kg of lipopolysaccharide under the conditions described in Example 13, causes a decrease in survival at 48 hours of less than 20% as compared to the administration of 1000 mg/kg of human serum albumin with co-administration of 5 mg/kg of lipopolysaccharide.

"Reduced gastrointestinal effect" hemoglobin, as used herein, is defined as a hemoglobin which, upon administration at a dose of 1500 mg/kg to conscious Sprague Dawley rats under the conditions described in Example 11, causes a decrease in gastric emptying of less than 20% as compared to the administration of 1500 mg/kg of human serum albumin.

"Reduced lesion" hemoglobin, as used herein, is defined as a hemoglobin which, upon administration at a dose of 2000 mg/kg to rhesus monkeys (*Macaca mulatta*) under the conditions described in Example 10, causes no more than minimal (focal or multifocal) heart lesions. Hemoglobins which cause the formation of mild lesions in any of the rhesus monkey test subjects are not considered to be reduced lesion hemoglobins.

"Reduced pressor effect" hemoglobin, as used herein, is defined as a hemoglobin which, upon administration at a dose of 2000 mg/kg to Sprague Dawley rats under the conditions described in Example 12, causes an increase in mean arterial pressure of less than 20 mm Hg.

"Shock" is defined, for the purposes of this invention, as a condition of profound hemodynamic and metabolic disturbance characterized by a failure of the circulatory system to maintain adequate perfusion of vital organs. Shock resulting from an insufficient blood volume to maintain adequate cardiac output, blood pressure, and tissue perfusion is referred to as "hypovolemic shock." Hypovolemic shock resulting from acute hemorrhage is referred to as "hemorrhagic shock." Shock resulting from primary failure of the heart in its pumping function, as in myocardial infarction, severe cardiomyopathy, or mechanical obstruction or compression of the heart is referred to as "cardiogenic shock."

"Stroke" is defined, for the purposes of this invention, as stroke syndrome caused by a stenosis or occlusion of a feeding blood vessel in the brain.

"Surgical device" is defined, for the purposes of this invention, as any mechanical device used in the course of surgery which contains a fluid void volume. A "fluid void volume" is the volume within the surgical device which must be flushed with fluid to remove air in order to render it safe for use in the operation. An example would be a lumen in an angioplasty catheter which is intended to carry blood during the use of that catheter. Another example would be the exchange volume of a blood oxygenator. "Priming" is the process of flushing the fluid void volume with a fluid.

"T-state hemoglobin" is the low affinity state of hemoglobin and is the dominant form of hemoglobin when it is deoxygenated ("deoxy", or "T" (for tense) state).

In the instant specification, several recombinant hemoglobins have been utilized to illustrate the invention. A list of these hemoglobins, along with descriptions of any mutations and basic physical properties, is given in the table below:

TABLE 1

Hemoglobin Nitric oxide Reactivity Data

| Recombinant Hemoglobin | Globin Subunit Description | $k'_{NO,ox}$ ($\mu M^{-1} s^{-1}$) | $P_{50}$ (mmHg) |
|---|---|---|---|
| rHb0.1 | di$\alpha$V1M/$\beta$V1M[1] | 58 | 10 |
| rHb1.1 | di$\alpha$/$\beta$N108K | 58 | 32 |
| SGE2821 | di$\alpha$(L29F, H58Q)[2]/$\beta$L106W | 12 | 44 |
| SGE2822 | di-di$\alpha$(L29F, H58Q)/$\beta$L106W | 11 | 37 |
| SGE2971 | di-di$\alpha$(L29W, H58Q)/$\beta$V67W, K82D | 2.5 | 49 |
| SGE3010 | di$\alpha$(L29W, H58Q)/$\beta$V67W, K82D | 2.5 | 52 |
| SGE3011 | di$\alpha$(L29W, H58Q)/$\beta$V67W | 2.5 | 43 |
| SGE3343 | di-di$\alpha$/$\beta$K82D, N108K | 58 | 38 |
| SGE3345 | di$\alpha$/$\beta$K82D, N108K | 58 | 44 |
| SGE3653 | di$\alpha$(L29F, H58Q)/$\beta$V67W | 15/2[4] | 29 |
| SGE3927 | di$\alpha$(L29W, H58Q), K158C[3]/$\beta$V67W, T87Q, C93A | 2.5 | 34 |
| SGE3937 | di$\alpha$(L29W, H58Q)/$\beta$S9C, V67W, D73K, K82D, T87Q, C93A | 2.5 | ~38 |
| SGE3959 | di$\alpha$(L29W, H58Q)/$\beta$V67W, T87Q | 2.5 | 43 |
| SGE3487 | di$\alpha$(L29W, H58Q)/$\beta$V67W, T87Q | 2.5 | ~34 |
| SGE3928 | di$\alpha$(L29W, H58Q)/delta V67W | 2.5 | 30 |
| SGE3938 | di$\alpha$(L29W, H58Q)/delta V67W, K82D | 2.5 | 45 |

[1]The n-terminal Val → Met mutation, a result of expression in bacteria, is to be understood in all other hemoglobins listed in the table.
[2]The mutations listed in parentheses are present in each alpha sequence of the di $\alpha$ or di-di $\alpha$ subunit.
[3]This mutation is only present in the second alpha sequence of the di $\alpha$ subunit.
[4]The values for $k'_{NO,ox}$ ($\mu M^{-1} s^{-1}$) are in this case expressed as two values, which reflects one rate (15) for $\alpha$ subunits and a different rate (2) for $\beta$ subunits.

Introduction

The invention generally relates to hemoglobins exhibiting certain physico-chemical characteristics which produce reduced or no heart lesions, reduced or low gastrointestinal effects, reduced or low pressor effects, and/or reduced endotoxin effects, when administered in therapeutic applications to mammals, and pharmaceutical compositions comprising such hemoglobins. These hemoglobins may be generally referred to as "reduced side effect" hemoglobins. The hemoglobins are preferably recombinantly produced hemoglobins with mutations which beneficially effect their physico-chemical characteristics. In addition, the more preferred hemoglobins of the invention, with the lowest incidence and severity of biological side effects, are intermolecularly crosslinked or polymerized.

In a preferred embodiment, the present invention utilizes mutant hemoglobins that eliminate or produced significantly reduced numbers of heart lesions in the rhesus monkey test as described below. Thus, the mutant hemoglobins preferred in the present invention are also referred to herein as "reduced lesion mutants." Most preferably, these hemoglobins produce no heart lesions in the rhesus monkey test. These mutant hemoglobins most preferred in the present invention are also referred to as "lesion free mutants." In another preferred embodiment, the present invention utilizes hemoglobins which cause a reduced mean arterial blood pressure increase, or a reduced pressor effect, when administered as a therapeutic agent. Thus, these hemoglobins of the present invention are referred to herein as "reduced pressor effect" hemoglobin. Most preferably, these hemoglobins produce greatly reduced arterial blood pressure effects, as measured by comparison to the administration of a comparable amount of human serum albumin. These mutant hemoglobins most preferred in the present invention are also referred to as "low pressor effect" hemoglobin.

In another preferred embodiment, the present invention utilizes hemoglobins with reduced deleterious gastrointestinal effects, such as upper gastrointestinal discomfort including mid-epigastric discomfort, abdominal pain and/or dyspepsia and/or lower gastrointestinal discomfort including lower abdominal pain, flatulence and/or diarrhea, when administered as a therapeutic agent. Thus, these hemoglobins of the present invention are referred to herein as "reduced gastrointestinal effect" hemoglobin. Most preferably, these hemoglobins produce greatly reduced gastrointestinal side effects, as measured by the gastric emptying test in rats. These mutant hemoglobins most preferred in the present invention are also referred to as "low gastrointestinal effect" hemoglobin.

In another preferred embodiment, the present invention utilizes hemoglobins which cause reduced endotoxin hypersensitivity effects. Thus, these hemoglobins of the present invention are referred to herein as "reduced endotoxin effect" hemoglobin.

In more preferred embodiment, the present invention utilizes hemoglobins which have combinations or permutations of the above biological characteristics, in either a reduced or low to zero degree. These hemoglobins can be generally referred to as "multiple reduced side effect" hemoglobins.

In one embodiment of the present invention, a physiologically acceptable solution of reduced side effect recombinant hemoglobins may be used as a blood substitute. Because of their oxygen carrying capacity and freedom from infective agents, such solutions are an important supplement to treatments of whole blood infusion. In addition, the reduced lesion and lesion free mutant hemoglobins eliminate or significantly reduce the lesion-creating response when administered as an oxygen carrying blood substitute typically caused by other extracellular hemoglobins. In addition to its general use as a blood substitute, recombinant reduced side effect hemoglobin solutions may also be used as oxygen-carrying solutions to treat hypovolemia and hemorrhagic or hypovolemic shock, and cardiogenic shock.

Because the distribution in the vasculature of extracellular hemoglobins is not limited by the size of the red blood cells, the hemoglobins of the present invention can be used to deliver oxygen to areas that red blood cells cannot penetrate. These areas can include any tissue areas that are located downstream of obstructions to red blood cell flow, such as areas downstream of thrombi, sickle cell occlusions, arterial occlusions, angioplasty balloons, surgical instrumentation, any tissues that are suffering from oxygen starvation or are hypoxic, and the like. Additionally, all types of tissue ischemia can be treated using the methods of the instant invention. Such tissue ischemias include, for example, stroke, emerging stroke, transient ischemic attacks, myocardial stunning and hibernation, acute or unstable angina, emerging angina, infarct, and the like. The recovery of tissues from physical damage such as burns can also be accelerated by pretreatment with recombinant hemoglobin, which allows increased perfusion and oxygenation of the tissues.

Use of hemoglobins of the present invention for treatment of sickle cell anemia patients overcomes disadvantages of current therapies. Sickle cell anemia patients in vasoocclusive crisis are currently treated by transfusion of red blood cells in conjunction with dilution and pain management. Cell-free hemoglobin products not only deliver oxygen preventing further sickling (as do red blood cells), they also penetrate vessels already occluded with deformed red cells to better alleviate pain and minimize tissue damage. Also, frequent transfusions in the sickle cell anemia population result in alloimmunization to red cells and to platelets, an adverse effect that would be avoided by use of cell-free hemoglobin. Reduced side effect hemoglobins offer a significant therapeutic advantage over cell-free hemoglobins with wild-type nitric oxide kinetics in treatment of sickle cell anemia patients, since they elicit a lesser degree of vasoconstriction or none at all. This is clearly an advantage in the treatment of vasoocclusive crisis, and is also an advantage in other treatments of sickle cell anemia patients in situations where there is a risk of sudden onset of vasoocclusive crisis. For example, cell-free hemoglobins may be used in place of packed red cells for preoperative transfusion of sickle cell anemia patients to minimize risk of anesthesia. Cell-free hemoglobin may also be administered periodically to minimize risk of stroke.

In one embodiment of the present invention, reduced side effect mutant hemoglobins can be used to treat anemia, both by providing additional oxygen carrying capacity in a patient that is suffering from anemia, and/or by stimulating hematopoiesis as described in PCT publication WO 95/24213, incorporated herein by reference. When used to stimulate hematopoiesis, administration rates can be slow because the dosage of hemoglobin is much smaller than dosages that can be required to treat hemorrhage. Therefore the reduced side effect hemoglobins of the instant invention can be used for applications requiring administration to a patient of high volumes of hemoglobin as well as in situations where only a small volume of the hemoglobin of the instant invention is administered.

In addition, the present invention provides for several specialized uses of reduced side effect hemoglobin. Reduced side effect hemoglobins can be used as an adjunct with radiation or chemotherapy to enhance the effectiveness of these cancer treatments. Reduced side effect hemoglobin preparations may also be used to treat head injury in mammals, to increase cerebral perfusion pressure and decrease intracranial pressure.

Reduced side effect hemoglobins can be formulated for use in various therapeutic applications. Representative formulations suitable for carrying out the methods of the instant invention are described in Milne, et al., WO 95/14038 and Gerber et al., U.S. Pat. No. 5,914,391, both herein incorporated by reference. In order to avoid complications in administration, the hemoglobin compositions for use in the present invention should be high purity, i.e. free from stroma and pyrogens. Preferably, the compositions should have an endotoxin level of no more than 0.25 EU/ml, as measured by the LAL (*limulus* amebocyte lysate) test. In addition, in order for the reduced side effect hemoglobin compositions of the present invention to carry oxygen effectively, the methemoglobin content must be controlled. Preferably, the reduced side effect hemoglobin compositions of the present invention have a methemoglobin content of less than 15%, more preferably less than 10%, and most preferably less than 5%, when used in the applications described below. For use in the invention, reduced side effect hemoglobins may be incorporated in conventional pharmaceutical formulations (e.g. injectable solutions) for use in treating mammals in need thereof. Pharmaceutical compositions can be administered by subcutaneous, intravenous, or intramuscular injection, or as large volume parenteral solutions and the like.

For example, a parenteral therapeutic composition may comprise a sterile isotonic saline solution containing between 0.1 percent and 90 percent weight to volume of recombinant reduced side effect hemoglobin. A preferred extracelluar hemoglobin solution of recombinant reduced side effect hemoglobin contains from about 5 percent to about 20 percent, more preferably from about 5 percent to about 17 percent, more preferably from about 8 to about 14 percent, and most preferably about 10 percent hemoglobin in solution (% weight per volume). The selection of percent hemoglobin depends on the oncotic properties of the chosen hemoglobin product. It is preferred that the hemoglobin solutions formulated for use in the present invention be normo-oncontic to hyperoncotic. The percent hemoglobin may be adjusted to obtain the desired oncotic pressure for each indication. Applicants have found concentrations of about 8–14 g/dl of the recombinant reduced side effect hemoglobins used in the examples to provide the correct oncotic pressure. However, concentrations from about 1 to about 20 g/dl hemoglobin are suitable for use in the present invention.

A typical dose of recombinant reduced side effect hemoglobin as a therapeutic agent can be from about 1 to about 15,000 milligrams of hemoglobin per kilogram of patient body weight. More usually, when used as an oxygen carrying composition, or as a blood substitute, the dosage will range between 100 to 7500 mg/kg patient body weight, more preferably 500 to 5000 mg/kg body weight, and most preferably 700 to 3000 mg/kg body weight. Thus, a typical dose for a human patient might be from a gram to over 1000 grams. It will be appreciated that the unit content of active ingredients contained in an individual dose of each dosage form need not in itself constitute an effective amount, as the necessary effective amount could be reached by administration of a number of individual doses. The selection of dosage depends upon the dosage form utilized, the condition being treated, and the particular purpose to be achieved according to the determination of those skilled in the art.

For use in the present invention, the reduced side effect hemoglobin can be dialyzed or exchanged by ultrafiltration into a physiologically acceptable solution. More preferably, the hemoglobins of the present invention are formulated at a concentration of 50–150 g/l. The solution generally comprises a physiologically compatible electrolyte vehicle isosmotic with whole blood and which maintains the reversible oxygen-carrying and delivery properties of the hemoglobin. The physiologically acceptable solution can be, for example, physiological saline, a saline-glucose mixture, Ringer's solution, lactated Ringer's solution, Locke-Ringer's solution, Krebs-Ringer's solution, Hartmann's balanced saline, heparinized sodium citrate-citric acid-dextrose solution, and polymeric plasma substitutes, such as polyethylene oxide, polyvinyl pyrrolidone, polyvinyl alcohol and ethylene oxide-propylene glycol condensates. Each formulation according to the present invention may additionally comprise inert constituents including pharmaceutically-acceptable carriers, diluents, fillers, salts, and other materials well-known in the art, the selection of which depends on the dosage form utilized, the condition being treated, the particular purpose to be achieved according to the determination of the ordinarily skilled artisan in the field and the properties of such additives. For example, in addition to recombinant mutant hemoglobin, a physiologically acceptable solution also includes 0–200 mM of one or more physiological buffers, 0–200 mM of one or more carbohydrates, 0–200 mM of one or more alcohols or poly alcohols, 0–200 mM of one or more physiologically acceptable salts, and 0–1% of one or more surfactants, 0–20 mM of a reducing agent, and is at pH 6.7–7.9. More preferably, a physiologically acceptable solution contains, in addition to recombinant reduced side effect hemoglobin, 0–50 mM sodium gluconate, 0–50 mM of one or more carbohydrates (e.g. glucose, mannitol, sorbitol or others known to the art), 0–300 mM of one or more chloride salts and, optionally, 0–0.5% surfactant, e.g. Tween™ [polysorbate 80], and/or 0–20 mM N-acetyl cysteine. Even more preferably, a physiologically acceptable solution contains, in addition to recombinant reduced side effect hemoglobin, 0–50 mM sodium gluconate, 0–200 mM sodium chloride, 0–25 mM potassium chloride, and, optionally, 0–0.5% surfactant, e.g. Tween™ [polysorbate 80] and/or 0–20 mM N-acetyl cysteine, pH 6.9–7.8. Most preferably, a physiologically acceptable solution includes, in addition to recombinant reduced side effect hemoglobin, 24 mM sodium gluconate, 115 mM sodium chloride 4 mM potassium chloride and, optionally, 0.025% Tween™ 80 and/or 9 mM N-acetyl cysteine, pH 7.0. This most preferred physiologically acceptable solution is referred to herein as "formulation buffer." Other components may be added if required, such as reducing agents, anti-oxidants, anti-bacterial agents, oncotic pressure agents (e.g. albumin or polyethylene glycols) and other physiologically acceptable salts and sugars. An alternative suitable formulation for purified recombinant reduced side effect hemoglobin is in a solution of 150 mM NaCl, 5 mM sodium phosphate, pH 7.4.

Administration of recombinant reduced side effect hemoglobin can occur for a period of seconds to hours depending on the purpose of the hemoglobin usage. For example, when used as an oxygen carrier for the treatment of severe hemorrhage, the usual time course of administration is as rapidly as possible. Typical infusion rates for hemoglobin solutions as oxygen therapeutics can be from about 100 ml/hour to about 3000 ml/hour, preferably from about 1 ml/kg/hour to about 300 ml/kg/hour, most preferably from about 1 ml/kg/hour to about 25 ml/kg/hour.

Reduced Heart Lesion and Lesion Free Hemoglobins

Candidates for use in the therapeutic applications of the present invention are screened for the occurrence of myocardial necrosis during administration. Preferably, a preliminary screen is conducted in a less sensitive test animal such as a rabbit or pig. However, to closely emulate administration to humans, the rhesus monkey, a sensitive primate model, is used. In the primate, the myocardial lesions which have been observed after extracellular hemoglobin infusion are typically described as a minimal to moderate myocardial degeneration, characterized by cytoplasmic swelling and vacuolization of myofibers, occurring primarily in the left ventricle and/or septum. The lesions are usually focal or multifocal in distribution. Often the degeneration is associated with foci of coagulative myofiber necrosis which display a homogeneous to granular eosinophilic straining cytoplasm. Enlargement of the nuclei (karyomegaly) of myocytes and minimal to mild interstitial fibrosis are also frequently associated with the degenerative lesions.

To quantify the characteristics of the cardiac lesions using anatomic pathology, two parameters in particular, incidence and severity, are enlisted. Incidence is the number of hearts which exhibit any evidence of lesion formation divided by the number of hearts examined (e.g. 2/4). Severity is a measure of lesion intensity and extent, which is graded by the evaluating pathologist on an ascending scale of 0–4. Lesions of Grade 1 are considered minimal, Grade 2 are considered mild, Grade 3 are moderate, and Grade 4 lesions are severe. In a given group of tissue specimens, an overall average severity score is also calculated by summing the severity grades for each affected heart and dividing the sum by the total number of hearts evaluated in that group.

Above the no-effect level of about 100 mg/kg for wild type hemoglobin in rhesus monkeys, a dose-response relationship is observed, with a 100% incidence reached at 700 mg/kg. At the highest dose level evaluated in routine screens (2000 mg/kg), the incidence and overall severity are comparable to that observed around 700 mg/kg, suggesting a maximal response at 700 mg/kg (i.e., at substantially higher doses than the first effects doses, no increase in the severity of the lesion is observed).

To examine the severity of the lesions quantitatively, a morphometry study may be conducted in rhesus monkeys after the infusion of 2000 mg/kg of candidate hemoglobin. Five or more animals are infused intravenously with 20 mL/kg of a 10% hemoglobin solution at a rate of 1.0 mL/kg/min. The animals are sacrificed 7 days post-infusion, and the heart tissue collected, fixed, sectioned and examined by morphometric analysis [(Lilja, 1992)].

Applicants have found that certain hemoglobins produce markedly fewer heart lesions when administered to rhesus monkeys in a large dose (2000 mg/kg), as shown in Table 2. These reduced lesion hemoglobins are typically those with very low nitric oxide kinetics (<5 $\mu M^{-1}s^{-1}$). In addition, hemoglobins which have moderate nitric oxide kinetics (<15 $\mu M^{-1}s^{-1}$) and which are polymerized, produce mild heart lesions. Thus, polymerized hemoglobin mutants with low nitric oxide kinetics (<10 $\mu M^{-1}s^{-1}$) should be reduced lesion hemoglobins for use in the present invention. Applicants have also found that hemoglobins with very low nitric oxide kinetics (<5 $\mu M^{-1}s^{-1}$) which are polymerized become lesion free hemoglobins. Although not bound to any particular theory, applicants propose that these hemoglobins are large enough to prevent extensive extravasation into surrounding tissues, and have sufficiently low nitric oxide kinetics that the few molecules which do extravasate produce effects which are relatively innoxious to the myocardial fibers.

In addition, changes in the chemical cross-linking reagent, or other chemical modifications of the hemoglobin, may also detrimentally effect heart lesion production. However, applicants have found overall that polymerization of low nitric oxide kinetic hemoglobins is a productive method of producing lesion free hemoglobins for use in therapeutic compositions. Although applicants have utilized genetic methods to alter the nitric oxide reactivity of hemoglobin, it is contemplated that other methods, such as chemical modification, could be utilized to accomplish the same result.

Reduced and Low Pressor Effect Hemoglobins

Candidate hemoglobins for use in the present invention should also be tested for their hemodynamic effects. Applicants have found the Sprague Dawley rat top-load study, 2000 mg/kg useful for observing the hemodynamic side effects of candidate hemoglobins. Arterial blood pressure is measured through an arterial catheter, and cardiac output is measured by a pulsed Doppler flow probe on the ascending aortas after the rats are infused with the candidate hemoglobin. Blood pressure and flow data are averaged over an observation period of 90 minutes. Total vascular resistance is calculated by dividing the change in blood pressure by the change in cardiac output.

Figure 8:
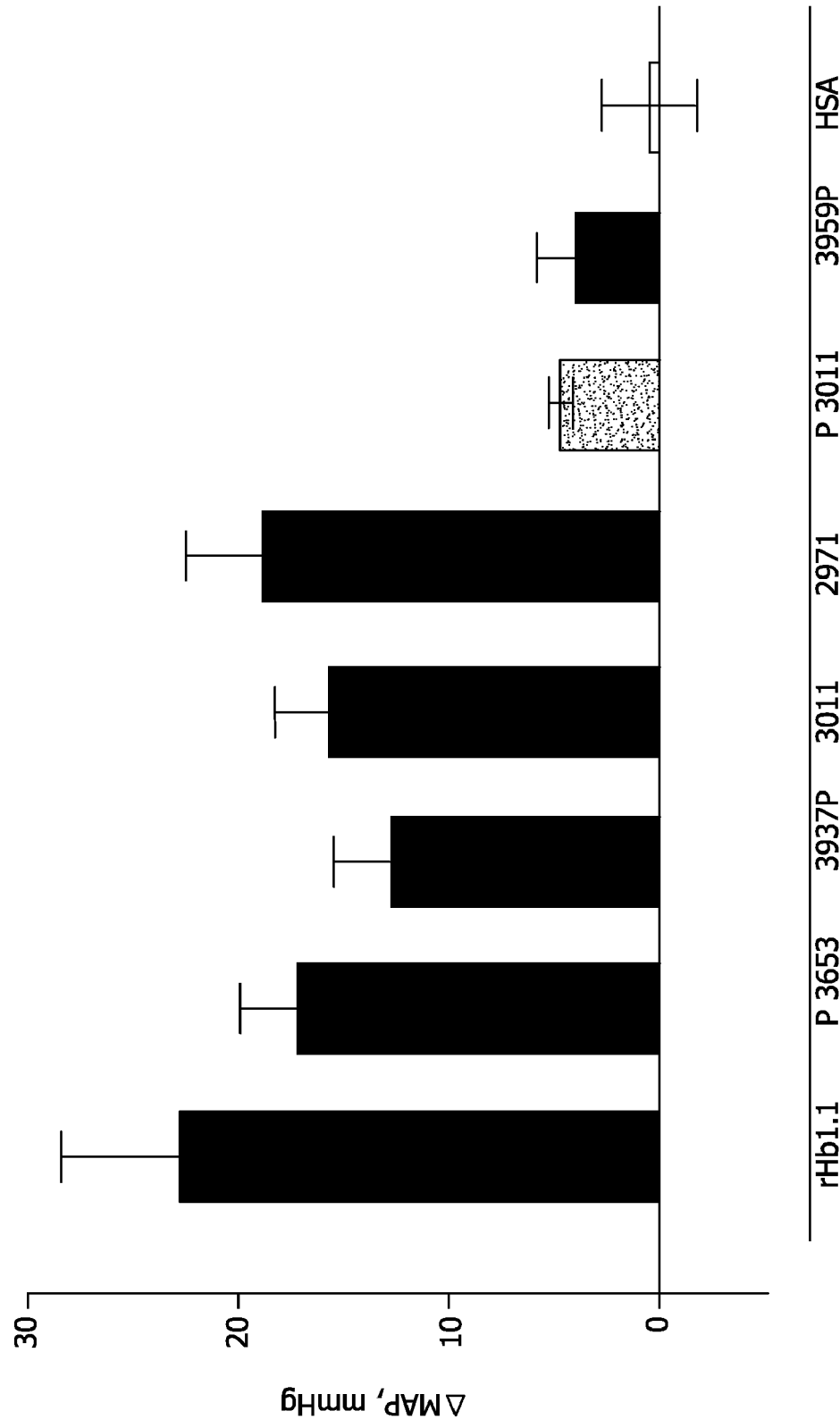
FIG. 8 shows the mean arterial pressure (MAP) responses in Sprague Dawley rats to recombinant hemoglobin compositions and human serum albumin. HSA was administered as an injection volume and oncotic control. Protein doses were 2000 mg/kg for the recombinant hemoglobins and for HSA. The change in MAP was calculated from the average change in blood pressure from 10 to 90 minutes following administration from baseline (average arterial pressure for the period starting 30 minutes prior to administration).

As can be seen from FIG. 8, both polymerization of the hemoglobin molecule and the nitric oxide kinetics of the hemoglobin moderate the pressor effect of the hemoglobin compositions. For instance, SGE3011, which has relatively low nitric oxide kinetics (<5 $\mu M^{-1}s^{-1}$), produced a mean arterial pressure (MAP) increase of 16 mm Hg as compared to HSA, while glutaraldehyde polymerized SGE3011 produced an increase of just 4.5 mm Hg. Similarly, rHb1.1, with wild type nitric oxide kinetics, exhibited a somewhat greater increase (23±5 mm Hg) than polymerized SGE3653 (17 mm Hg), with intermediate nitric oxide kinetics, which in turn exhibited a greater increase than monomeric SGE3011. As shown by BMA-PEG polymerized SGE3959, a low nitric oxide reactivity hemoglobin can be a reduced pressor effect hemoglobin. Also, a monomeric or dimeric hemoglobin with very low nitric oxide kinetics (SGE3011 and SGE2971) can be a reduced pressor effect hemoglobin. However, applicants have found that both low nitric oxide kinetics (<5 $\mu M^{-1}s^{-1}$) and polymerization are preferred in order to produce a low pressor effect hemoglobin. As can be seen from FIG. 8, only polymerized SGE3011 and SGE3959 produced a MAP increase of less than 10 mm Hg over baseline at a dose of 2000 mg/kg.

Reduced and Low Gastrointestinal Effect Hemoglobin

Candidate hemoglobins for use in the present application should also be tested for gastrointestinal side effects. The gastric emptying test in male Sprague-Dawley rats has been found to be an effective measure of the effect of extracellular hemoglobin solutions on the functioning of the smooth muscles of the gastrointestinal tract. In this test, the rats are administered the test hemoglobin solution, force-fed a liquid meal, allowed time to digest the meal, and then sacrificed. The amount of the liquid meal retained in the stomach (weight of the stomach and meal minus the weight of the stomach alone) is compared to the weight of the original meal to assess the portion of the meal which has passed through the digestive tract. A more detailed description of the test protocol is given in Example 11.

Figure 7:
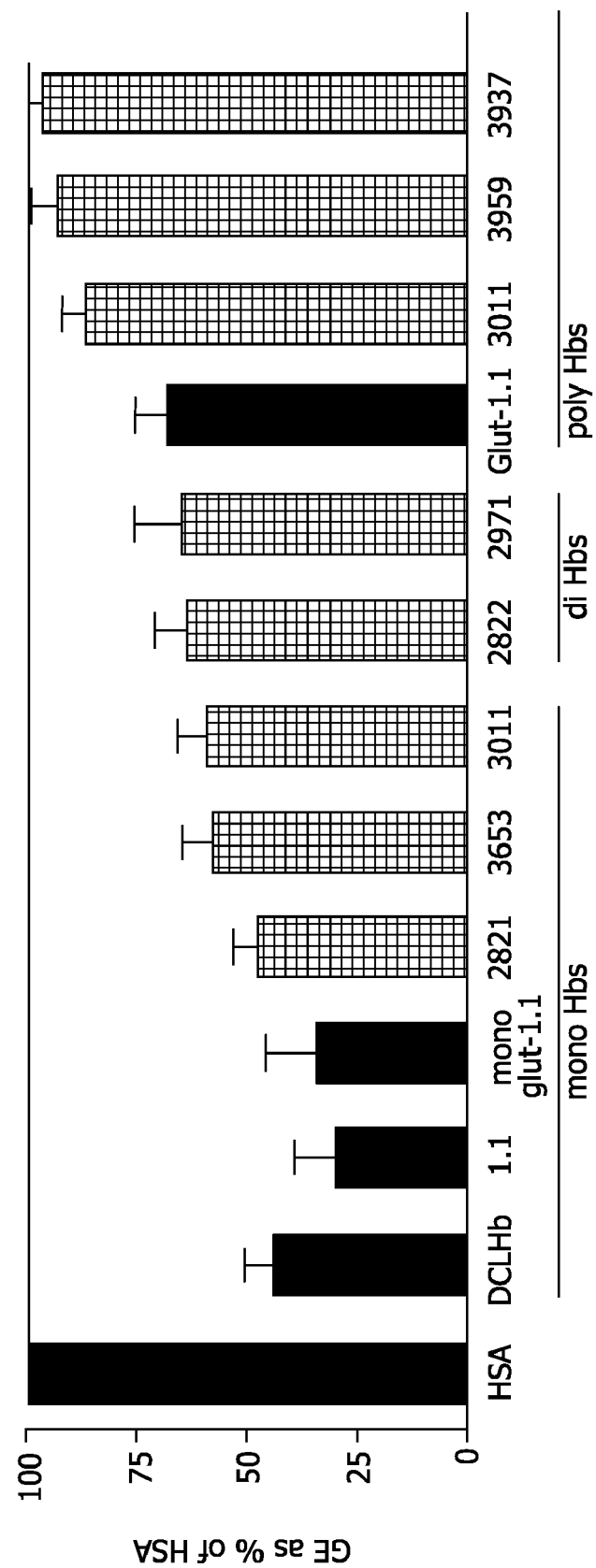
FIG. 7 shows the gastric emptying effects in Sprague Dawley rats of several recombinant hemoglobin compositions, diaspirin crosslinked hemoglobin (DCLHb) and human serum albumin (HSA). Protein doses were 1500 mg/kg for each hemoglobin composition and for HSA. "Mono Hbs" refers to the single-tetramer hemoglobin species (MW about 64,000), "di Hbs" indicate two hemoglobin tetramers that are genetically fused (MW about 128,000) and "polyhbs" indicate two or more hemoglobin tetramers that are chemically crosslinked. The gastric emptying effect of the tested hemoglobin compositions is expressed as a percentage of control HSA.

As can be seen from FIG. 7, both polymerization of the hemoglobin molecule and the nitric oxide kinetics of the hemoglobin have an effect on gastrointestinal dysmotility. For instance, SGE3011, which has relatively low nitric oxide kinetics (<5 $\mu M^{-1}s^{-1}$), had a gastric emptying of only 58.3% as compared to HSA, while the dimer SGE2971 (with the same nitric oxide kinetics) exhibited 64.3% emptying, and glutaraldehyde polymerized SGE3011 exhibited an emptying of 86.6%. Similarly, rHb1.1, with wild type nitric oxide kinetics, exhibited far less emptying (29.6%) than SGE2821 (46.9%), with intermediate nitric oxide kinetics, which in turn exhibited less emptying than SGE3011. However, applicants have found that both low nitric oxide kinetics (<5 $\mu M^{-1}s^{-1}$) and polymerization are preferred in order to produce a reduced or low gastric effect hemoglobin. As can be seen from FIG. 7, only polymerized SGE3011, SGE3959 and SGE3937 were within 20% of the HSA gastric emptying rate.

Low Endotoxin Effect Hemoglobins

Applicants have observed that the administration of extracellular hemoglobin compositions, such as rHb1.1, causes mammals to become hypersensitive to endotoxin, producing high mortality rates in rodents well below the established $LD_{50}$ of the standard lipopolysaccharide. In order to screen for this side effect, applicants have found that coadministration of a large dose of the recombinant hemoglobin candidate composition (1000 mg/kg) and lipopolysaccharide (5 mg/kg) to BALB/c mice provides a reasonable measure of endotoxin hypersensitivity. After coadministration, the mice are observed for 48 hours, and a mortality rate determined. A more complete description of the test is given in Example 13.

Figure 10:
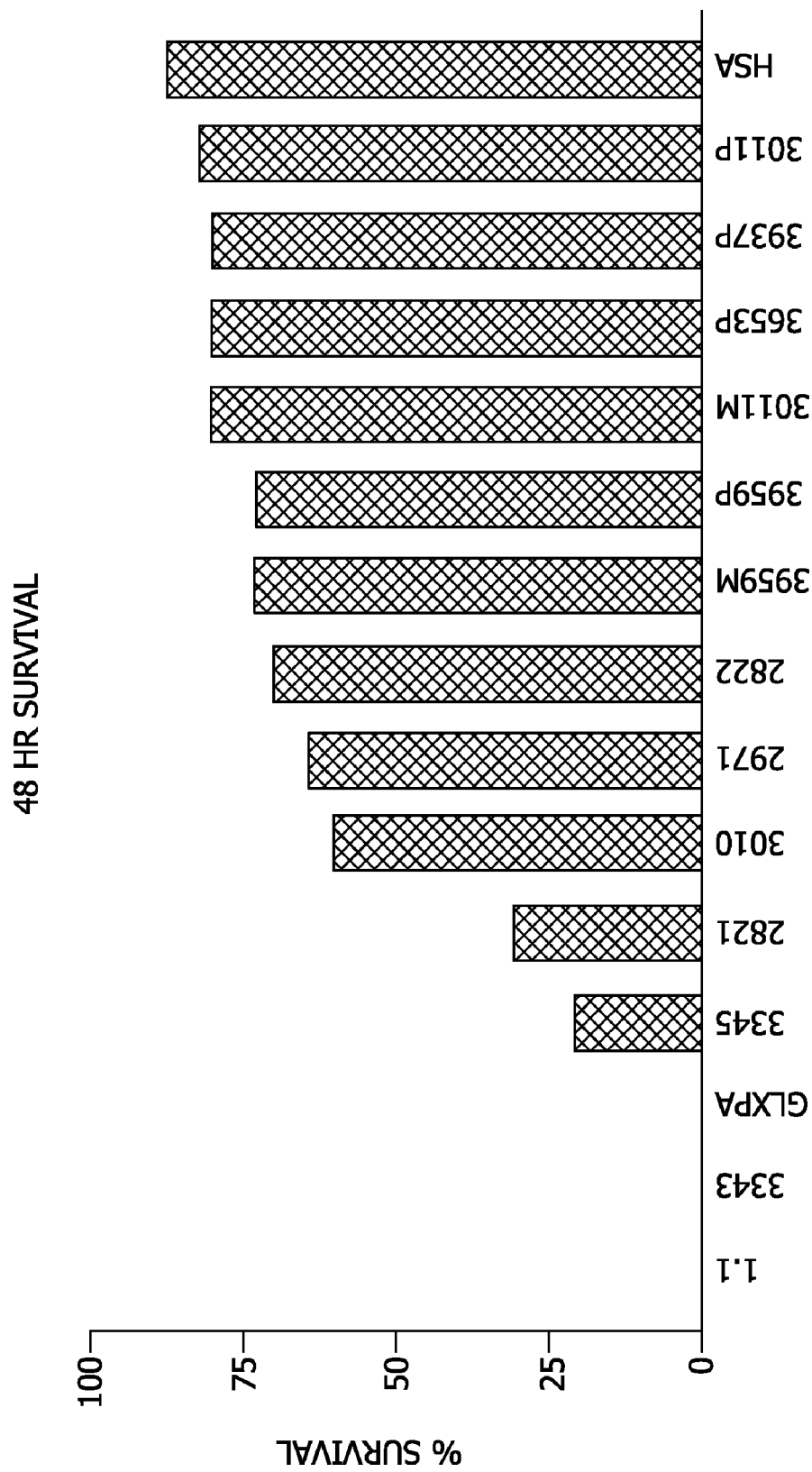
FIG. 10 depicts the 48 hour survival rate of inbred BALB/cByJ mice injected with 5 mg/kg purified LPS and 1000 mg/kg of test hemoglobin solutions as set forth in Table 6. Mice injected with 5 mg/kg purified LPS and 1000 mg/kg HSA were used as a control.

As shown in FIG. 10, hemoglobins with low (<15 $\mu M^{-1}s^{-1}$) or very low (<5 $\mu M^{-1}s^{-1}$) nitric oxide reactivity demonstrate a reduced endotoxin effect as compared to those with native nitric oxide reactivity, such as rHb1.1 and SGE3345. In addition, dimerization reduces the endotoxin effect of the hemoglobins tested, and polymerization greatly reduces the endotoxin effect of low nitric oxide reactivity mutant hemoglobins. For instance, the polymerized low nitric oxide reactivity mutant SGE3653 has an endotoxin effect similar to that of monomeric or polymeric very low nitric oxide reactivity hemoglobin SGE3011. Thus, production of reduced endotoxin effect hemoglobins can be accomplished by utilizing very low nitric oxide reactivity mutations (<5 $\mu M^{-1}s^{-1}$), or by polymerizing low nitric oxide reactivity mutants.

Preferred Recombinant Mutant Hemoglobin for Use in the Invention

Recombinant hemoglobin mutants which exhibit reduced side effects preferably have one or more mutations in or around the heme pocket which reduce their rate of reactivity with nitric oxide. In addition, in order to further reduce the side effects of these hemoglobins, in one embodiment they preferably are polymerized to form polymerized mutant hemoglobins having an average molecular weight between 65 kD and 650 kD. In one embodiment, the hemoglobin is preferably polymerized to form polymerized mutant hemoglobins having an average molecular weight between 130 kD and 500 kD, more preferably between 190 kD and 350 kD. In another embodiment, the hemoglobin preferably includes about 40 to about 60% derivatized monomeric hemoglobin with an average molecular weight between 65 and less than 130 kD, and about 40 to about 60% oligomeric hemoglobin, which comprises two or more hemoglobin-like proteins, with an average molecular weight between 130 and 650 KD. As outlined below, several heme pocket mutants have been discovered which exhibit low to very low nitric oxide kinetics.

Heme is an iron-containing porphyrin that serves as a prosthetic group in proteins such as hemoglobin, myoglobin and the cytochromes. In hemoglobin, the heme appears in a cleft between the E and F helices in the globin subunits. The heme iron is linked covalently to the imidazole nitrogen of the "proximal" F8 histidine, while the distal E7 histidine and E11 valine appear near the access of oxygen to the heme pocket. The residues of the heme pocket include those residues that are on a nearest atom-to-nearest atom basis within 6 angstroms, and preferably within 4 angstroms, of the heme moiety (Fermi, et al. (1984) J. Mol. Biol. 175: 159–174). For alpha globin, the heme pocket residues include:

Distal Residues:

| First Shell | Second Shell |
|---|---|
| B10 Leu | B13 Met |
| CE1 Phe | E10 Lys |
| E7 His | E14 Ala |
| E11 Val | G12 Leu |
| G8 Leu | B14 Phe |
|  | B9 Ala |

Proximal Residues:

| First Shell | Second Shell |
|---|---|
| F8 His | C7 Tyr |
|  | F4 Leu |
|  | F7 Leu |
|  | FG3 Leu |
|  | FG5 Val |
|  | G4 Asn |
|  | G5 Phe |
|  | H15 Val |
|  | H19 Leu |

Distal Residues:

| First Shell | Second Shell |
|---|---|
| B10 Leu | B13 Leu |
| CD1 Phe | CD3 Ser |
| E7 His | B14 Leu |
| E11 Val | CD4 Phe |
| G8 Leu | E10 Lys |
|  | E14 Ala |
|  | G12 Leu |
|  | B9 Ala |

Proximal Residues:

| First Shell | Second Shell |
|---|---|
| F8 His | C7 Phe |
|  | F4 Leu |
|  | F7 Leu |
|  | FG3 Leu |
|  | FG5 Val |
|  | G4 Asn |
|  | G5 Phe |
|  | G12 Leu |
|  | H15 Val |
|  | H19 Leu |

The first shell residues are those residues in close or direct contact with the heme iron atom and/or the bound ligand, while second shell residues are those amino acids which are not in direct contact with the heme or the bound ligand, but are in direct contact with first shell residues. The term "heme pocket residues" includes these first and second shell residues.

In designing the reduced side effect hemoglobins utilized in the present invention, two independent protein engineering strategies were used to vary ligand affinities and rates of reaction: (1) manipulation of the intrinsic kinetics and affinities of nitric oxide and oxygen, respectively, by making novel substitutions in the distal pockets of the subunits, and (2) adjustment of the position of the allosteric R/T equilibrium with mutations at key points away from the heme groups. Changes in hemoglobin allostery are specific for oxygen binding kinetics and affinity, and the R/T equilibrium has no effect on nitric oxide scavenging. The distal pocket substitutions affect entry and exit rates of nitric oxide and oxygen by varying steric hindrance and hydrogen bonding.

Thus, the general strategy for identifying amino acid mutations for inclusion in the reduced side effects hemoglobin of the present invention is set forth as follows:

a) making mutations that cause one or more amino acid substitutions in the distal heme pockets of α, β, or delta globin subunits;

b) incorporating DNA fragments containing these mutations into a suitable expression vector, then introducing this vector into an appropriate host cell;

c) culturing the host cell to express soluble hemoglobin followed by purification of the hemoglobin;

d) measuring in vitro reactivity of purified hemoglobin with nitric oxide;

e) selecting the proper α mutations to pair with the proper β mutations or delta mutations;

h) optionally, selecting other mutations to adjust the $P_{50}$ or rate of oxygen dissociation;

i) in vivo testing for oxygen delivery and hemodynamic data; and j) conducting testing to verify the reduced side effect and retention of oxygen delivery as needed.

The general strategy for identifying amino acid mutations delineated above illustrates the process for selection of mutations in the alpha, beta or delta globin subunit. However, this strategy is also applicable for identifying mutations in other globin subunits such as gamma globin, epsilon globin, and/or zeta globin, which are within the scope of the present invention.

Any of the mutations described herein, or in the anti-aggregation mutant section below, can be accomplished by a number of methods that are known in the art. Mutations can be made at the codon level by alteration of the nucleotide sequence that codes for a given amino acid. Substitution of an amino acid at any given position in a protein can be achieved by altering the codon for that particular amino acid. This substitution can be accomplished by site directed mutagenesis using, for example: (1) the Amersham technique (Amersham mutagenesis kit, Amersham, Inc., Cleveland, Ohio) based on the methods of Taylor et al., Nucl. Acids Res. (1985) 13: 8749–8764; Taylor et al., (1985) Nucl. Acids Res. 13: 8764–8785; Nakamaye and Eckstein, (1986) Nucl. Acids Res. 14: 9679–9698; and Dente et al., in *DNA Cloning*, Glover, Ed., IRL Press (1985) pages 791–802, (2) the Promega kit (Promega Inc., Madison, Wis.) or (3) the Biorad kit (Biorad Inc., Richmond, Calif.), based on the methods of Kunkel, (1985) Proc. Natl. Acad. Sci. USA 82: 488; Kunkel et al., (1987) Meth. Enzymol. 154: 367; Kunkel, U.S. Pat. No. 4,873,192. It can also be accomplished by other commercially available or non-commercial means which incorporate the technique of site-directed mutagenesis using mutant oligonucleotides to achieve mutagenesis or as described in the Examples below.

Site directed mutagenesis can also be accomplished using PCR based mutagenesis such as that described in Zhengbin et al., pages 205–207 in *PCR Methods and Applications, Cold Spring Harbor Laboratory Press*, New York (1992); Jones and Howard, (1990) *BioTechniques* 8(2):178 (1990); Jones and Howard, *BioTechniques* 10: 62–66 (1991), or as described in the examples below. Site directed mutagenesis can also be accomplished using cassette mutagenesis with techniques that are known to those of skill in the art.

Any suitable host cell can be transformed with a plasmid containing the desired mutation(s) by methods known to those skilled in the art or as described in the examples below. Suitable host cells include, for example, bacterial, yeast, plant, mammalian and insect cells. *E. coli* cells are particularly useful for expressing the novel mutant hemoglobins. Preferably, when multiple subunits are expressed in bacteria, it is desirable, but not required, that the subunits be co-expressed in the same cell polycistronically as described in U.S. Pat. No. 5,559,907. It is preferable in *E. coli* to use a single promoter to drive the expression of the genes encoding the desired proteins.

The reaction of nitric oxide with oxyhemoglobin forms of the mutants often yielded biphasic reaction timecourses due to different reactivities of the two subunit types in the hemoglobin tetramer. Fitting these reaction timecourses to a two-exponential function yielded the reaction rates of both the wild-type and mutant subunits. By repeating this process for a large number of mutant constructs, a number of mutants in each subunit type were identified exhibiting a wide range of rate constants for nitric oxide reactivity ($k'_{NO, ox}$). The reduced side effect hemoglobins preferred for use in the present invention should have a rate constant for reaction of nitric oxide with oxyhemoglobin ($k'_{NO, ox}$) less than conventional hemoglobin. Preferably, the rate constant is less than about 20 $\mu M^{-1}s^{-1}$, more preferably less than 15 $\mu M^{-1}s^{-1}$, more preferably less than 10 $\mu M^{-1}s^{-1}$, and most preferably less than 5 $\mu M^{-1}s^{-1}$. After purifying and screening the large number of mutants, the following list of alpha and beta globin mutants and delta globin mutant combinations thereof were identified as having sufficiently reduced nitric oxide reactivity compared to conventional hemoglobin to be of particular use in the present invention (below about 20 $\mu M^{-1}s^{-1}$, as measured when the mutant subunit is paired with the corresponding native hemoglobin subunit). The mutations in bold are considered to be very low nitric oxide reactivity mutants (~3 $\mu M^{-1}s^{-1}$ in α and 3–6 $\mu M^{-1}s^{-1}$ in β), which will usually produce a very low reactivity hemoglobin (<5 $\mu M^{-1}s^{-1}$) when combined.

α Globin Mutations:
B10(Leu→Trp)+E7(His→Gln)
B10(Leu→Phe)
B10(Leu→Trp)
B10(Leu→Tyr)
B10(Leu→Trp)+E11(Val→Phe)
B10(Leu→Trp)+E11(Val→Phe)+G8(Leu→Ile)
B10(Leu→Trp)+E11(Val→Phe)+G8(Leu→Ala)
B10(Leu→Trp)+E11(Val→Leu)+G8(Leu→Phe)
B10(Leu→Trp)+E11(Val→Trp)
B10(Leu→Trp)+E11(Val→Trp)+G8(Leu→Trp)
B10(Leu→Trp)+E7(His→Gln)+E11(Val→Met)+G8(Leu→Val)
B10(Leu→Trp)+E7(His→Gln)+E11(Val→Phe)+G8(Leu→Val)
B10(Leu→Trp)+E7(His→Gln)+E11(Val→Leu)+G8(Leu→Val)
B10(Leu→Trp)+E7(His→Gln)+E11(Val→Leu)+G8(Leu→Trp)
B10(Leu→Phe)+E11(Val→Phe)
B10(Leu→Phe)+E7(His→Gln)+G8(Leu→Trp)
B10(Leu→Phe)+E7(His→Gln)+G8(Leu→Phe)
B10(Leu→Phe)+E7(His→Gln)+E11(Val→Met)
B10(Leu→Phe)+E7(His→Gln)+E11(Val→Met)+G8(Leu→Phe)
B10(Leu→Phe)+E7(His→Gln)+E11(Val→Met)+G8(Leu→Met)
B10(Leu→Phe)+E7(His→Gln)
B10(Leu→Phe)+E7(His→Gln)+E11(Val→Met)+G8(Leu→Ile)
E11(Val→Leu)
E11(Val→Phe)
E11(Val→Trp)
B9(Ala→Phe)

β Globin Mutations:
E11(Val→Trp)
E11(Val→Met)+G8(Leu→Trp)
E11(Val→Met)+G8(Leu→Phe)
B9(Ala→Leu)+E11(Val→Met)+G8(Leu→Trp)
G8(Leu→Phe)+G12(Leu→Trp)
E11(Val→Leu)+G8(Leu→Trp)
B9(Ala→Leu)+E11(Val→Leu)+G8(Leu→Trp)
G8(Leu→Trp)+G12(Leu→Trp)
B9(Ala→Leu)+E11(Val→Leu)
B9(Ala→Phe)+E11(Val→Leu)
B9(Ala→Trp)+E11(Val→Leu)
E11(Val→Leu)+G8(Leu→Phe)
E11(Val→Phe)+G8(Leu→Phe)
E7(His→Gln)+E11(Val→Trp)
G8(Leu→Trp)
G8(Leu→Phe)
B9(Ala→Phe)
B9(Ala→Trp)
B9(Ala→Leu)
B9(Ala→Met)
E11(Val→Phe)
E11(Val→Leu)
E11(Val→Met)
B13(Leu→Met)+E11(Val→Trp)
B10(Leu→Phe)
B10(Leu→Phe)+B14(Leu→Phe)
B10(Leu→Phe)+E4(Val→Leu)
B10(Leu→Phe)+E4(Val→Trp)
B10(Leu→Trp)+E4(Val→Leu)
B9(Ala→Leu)+G8(Leu→Trp)
B9(Ala→Trp)+G8(Leu→Phe)
B9(Ala→Phe)+G8(Leu→Trp)
B9(Ala→Trp)+G8(Leu→Trp)
E7(His→Gln)+E11(Val→Met)+G8(Leu→Trp)
B10(Leu→Ala)+E7(His→Phe)+G8(Leu→Trp)
E11(Val→Trp)+G8(Leu→Trp)

δ Globin Mutations:
E11(Val→Trp)

The above list of representative nitric oxide mutants is not intended to be exhaustive. Any mutation to alpha, beta, delta, epsilon, gamma and/or zeta which results in the production of reduced side effect hemoglobin is within the scope of the present invention. The designations used to reference the mutations first identify the helix, then the residue number within the helix, followed by the wildtype amino acid and the substituted amino acid. For example, E11(Val→Leu) refers to the eleventh residue of the E helix in which wildtype valine is substituted with leucine. While not being bound to a particular theory, it is believed that following administration of cell-free hemoglobin, a competition exists for the available nitric oxide between guanylyl cyclase and ferrous oxy- and deoxyhemoglobin (extravasation of the hemoglobin into or through the endothelium may be required). Those recombinant hemoglobins that have lower rates of reaction with nitric oxide are less potent competitors for nitric oxide. Consequently, the reduced side effect hemoglobins of the present invention are useful for a variety of applications due to their intrinsic lower reactivities, as they produce little or no perturbation in the natural turnover of nitric oxide, but remain capable of binding and delivering oxygen.

Any of the above alpha globin mutations can be combined with any of the above beta or delta globin mutations, or any of the above alpha globins can be combined with a known beta or delta globin and vice versa to obtain desirable kinetics for the production of reduced side effect hemoglobins. In addition, it is believed that any of the mutations identified for beta globin may be made to delta globin, gamma globin or epsilon globin to obtain desirable kinetics for production of reduced side effect hemoglobins. Equally, it is believed that any mutation identified for alpha globin may be made to zeta globin to obtain desirable kinetics for production of reduced side effect hemoglobins. Applicants have also found that it is advantageous to place the above mutations in di-α hemoglobin constructs in order to prevent the dissociation of the mutant hemoglobins into αβ dimers. Also, di-diα and larger genetically fused hemoglobins may be made with any combination of the above mutations to produce low nitric oxide reactivity hemoglobins with higher molecular weights.

The applicants have also demonstrate that if the amino acid substitutions used to reduce nitric oxide scavenging have an undesirable effect on oxygen delivery, the $P_{50}$ and rate of oxygen dissociation can be "corrected" by other strategically placed amino acid substitutions. The $P_{50}$ of cell free normal human hemoglobin $A_o$, <10, is too low to effectively deliver oxygen to the tissues of the blood and function as a blood substitute. Preferably, the reduced side effect hemoglobins of the present invention have a $P_{50}$ of 20–50, more preferably in the range of 25–45. Thus, at the alveolar partial oxygen pressure, the reduced side effect hemoglobin can pick up oxygen in the lungs and effectively deliver it to distant tissues of the body. Oxygen kinetics and equilibria can be manipulated by changing the position of the allosteric equilibrium, or by altering the intrinsic binding kinetics and affinity of the subunits. Mutations away from the distal heme pockets can be used to change the relative stabilities of the high-affinity "R" and low-affinity "T" allosteric states, which can lower or raise the oxygen affinity of the hemoglobin. List of mutations which are known to increase and decrease oxygen affinity can be found in U.S. Pat. No. 5,028,588, hereby incorporated by reference. Hemoglobin allostery has a significant effect on oxygen binding, but no effect on nitric oxide scavenging.

The following combinations of mutations have desirable nitric oxide reaction kinetics, and include other mutations which alter $P_{50}$:

αB10(Leu→Trp)+αE7(His→Gln)+βE11(Val→Trp)+βEF6 (Lys→Asp)
αB10(Leu→Trp)+αE7(His→Gln)+βE11(Val→Trp)+βF9 (Cys→Ala)
αB10(Leu→Trp)+αE7(His→Gln)+βE11(Val→Trp)+βF9 (Cys→Ser)
αB10(Leu→Trp)+αE7(His→Gln)+βE11(Val→Trp)+βF9 (Cys→Met)
αB10(Leu→Trp)+αE7(His→Gln)+βE11(Val→Trp)+βFG1 (Asp→Asn)
αB10(Leu→Trp)+αE7(His→Gln)+βE11(Val→Trp)+βHC3 (His→Gln)
αB10(Leu→Trp)+αE7(His→Gln)+βE11(Val→Trp)+βNA2 (His→Arg)
αB10(Leu→Phe)+βE11(Val→eTrp)+βG4(Asn→Tyr)
αB10(Leu→Phe)+βE11(Val→Trp)+βG10(Asn→Lys)
αB10(Leu→Phe)+βE11(Val→Trp)+βEF6(Lys→Asp)

In addition, hybrid di-α's (where two different alpha heme pockets are combined within the same di α genetically fused subunit) may be used, such as:

$α_1$B10(Leu→Phe)+$α_2$B10(Leu→Trp)+$α_2$E7(His→Gln)
$α_1$B10(Leu→Phe)+$α_2$B10(Leu→Trp)
$α_1$B10(Leu→Phe)+(Gly,Gly)+$α_2$B10(Leu→Trp)
$α_1$B10(Leu→Phe)+(Gly,Gly,Gly)+$α_2$B10(Leu→Trp)

The first two di-α subunits listed above have a single glycine linker between a globin domains. The third and fourth di-α subunits, as indicated, have linkers that comprise two and three glycine residues between α globin domains, respectively. These di-α subunits may be combined with various mutant beta and/or delta subunits to produce the hemoglobin compositions of the invention.

In addition to mutations which shift the $P_{50}$ of the hemoglobin mutant to acceptable levels for use as a therapeutic, other additional mutations may be desireable. For instance, mutations which increase the level of soluble hemoglobin expression in bacterial hosts, such as βD73E, βK82D, and βK82G, alone and in combinations, may be added to the above hemoglobins. A more thorough discussion of expression enhancing mutations may be found in WO 98/50430. In addition, applicants have discovered that hemoglobin with the mutation βK82D (Providence mutation) have lower serum lipase levels.

Crosslinking the Hemoglobins of the Invention

Mammalian hemoglobin is generally a tetramer composed of two alpha globin subunits (α1, α2) and two beta globin subunits (β1, β2). There is no sequence difference between α1 and α2 or between β1 and β2. The subunits of hemoglobin are noncovalently associated by Van der Waals forces, hydrogen bonds and, for deoxyhemoglobin (hemoglobin that is not carrying oxygen), salt bridges. Tetrameric hemoglobin is known to dissociate into α1β1 and α2β2 dimers which are eliminated from the bloodstream by renal filtration. This renal filtration of unmodified mammalian hemoglobin dimers can lead to renal failure and death. Hemoglobin dimers can extravasate easily into the tissues and be lost from the circulatory system. Intravascular retention of hemoglobin has been improved by for example, genetic fusion of the subunits of the tetramer in di-α or di-β subunits as taught by Hoffman, S. J and Nagai, K. in U.S. Pat. No. 5,028,588, Hoffman, et al., U.S. Pat. No. 5,545,727, and Anderson, D. et al., U.S. patent application Ser. No. 789,179, filed Nov. 8, 1991 or by chemical crosslinking of subunits within a single tetramer or between two or more tetramers (Bonhard, L. and Kothe, N., U.S. Pat. No. 4,777,244; Bonhard, K. and Boysen, U., U.S. Pat. No. 4,336,248; Bonsen, P., et al., U.S. Pat. Nos. 4,001,401, 4,053,590, and 4,001,200; Bucci, E., et al., U.S. Pat. No. 4,584,130; Feller, W., et al., U.S. Pat. No. 4,920,194; Feola, M. et al., PCT publication PCT/US90/07442; Garlick, R. L. et al., PCT publication PCT/US91/07155; Ilan, E. et al., EP publication EP 0361719; Iwasaki, K., et al.; U.S. Pat. 4,670,417 and EP Patent EP 0206448; Kluger, R. and Wodzinska, J., PCT publication PCT/CA92/00221 and U.S. Pat. No. 5,250,665; Kothe, N. et al., U.S. Pat. No. 3,525,272; Morris, K. C. et al., U.S. Pat. No. 4,061,736; Pepper, D. S. and McDonald, S. L., EP publication EP 0459788; Scannon, P. J., U.S. Pat. No. 4,473,496; Sehgal, L. R. et al., U.S. Pat. No. 4,826,811; Tye, R. W., U.S. Pat. No. 4,529,719; Walder, J. A. U.S. Pat. Nos. 4,598,064 and 4,600,531 and Ilan, E., EP Patent EP 0361719; among others). In one method, chemical crosslinking is accomplished by the use of an aliphatic dialdehyde. Dialdehydes cross-link proteins by reacting with —NH$_2$ groups to form Schiff's bases. In particular, glutaraldehyde modifies primary amines, which on proteins are available as N-terminal amines and ε-amines of lysine residues. X-ray crystallography of hemoglobin has shown that the N-ternini and the β and di-α subunits and the majority of the lysine residues are on the surface of the hemoglobin molecule and available to react with a crosslinker. A number of reaction parameters affect the characteristics of the final product. These parameters are known to those skilled in the art and include the hemoglobin concentration the length of the cross-linker molecule, the pH at which the reaction is conducted, the temperature of the reaction, the time allowed for the reaction to take place, and the molar ratio of hemoglobin to the cross-linker. In any of these forms, dissociation of hemoglobin into α1β1 and α2β2 dimers is prevented, thus increasing the intravascular retention of the protein and reducing renal toxicity.

As previously mentioned, the recombinant hemoglobins used in the instant invention are preferably intermolecularly crosslinked by methods known in the art, or can contain genetically fused globin subunits which form dimer or higher order hemoglobins, such as di-di-α subunits. These hemoglobins are preferably used according to the present invention to assist in limiting the extravasation or in reducing the colloid osmotic pressure of the hemoglobin composition. Applicants have found that very low nitric oxide kinetics alone are sometimes not sufficient to produce hemoglobins which are lesion free, reduced or low gastrointestinal effect, or low pressor effect. Often, increasing the mean molecular size of the hemoglobin to prevent extravasation is also required. Although dimerization of hemoglobins through the genetic fusion of two di-α subunits (di-di α hemoglobins) reduces the side effects of the hemoglobins used in the present invention, it does not usually produce low side-effect hemoglobins with respect to heart lesion, blood pressure, or gastrointestinal side effects. Therefore, polymerization of low nitric oxide reactivity hemoglobins is used in order to produce the more preferred low side effect hemoglobins. In addition, as illustrated in the rat blood pressure experiments, see FIGS. 8 and 9, polymerization can be used to produce reduced side effect hemoglobins from hemoglobin monomers which have less preferred nitric oxide kinetics.

Figure 12:
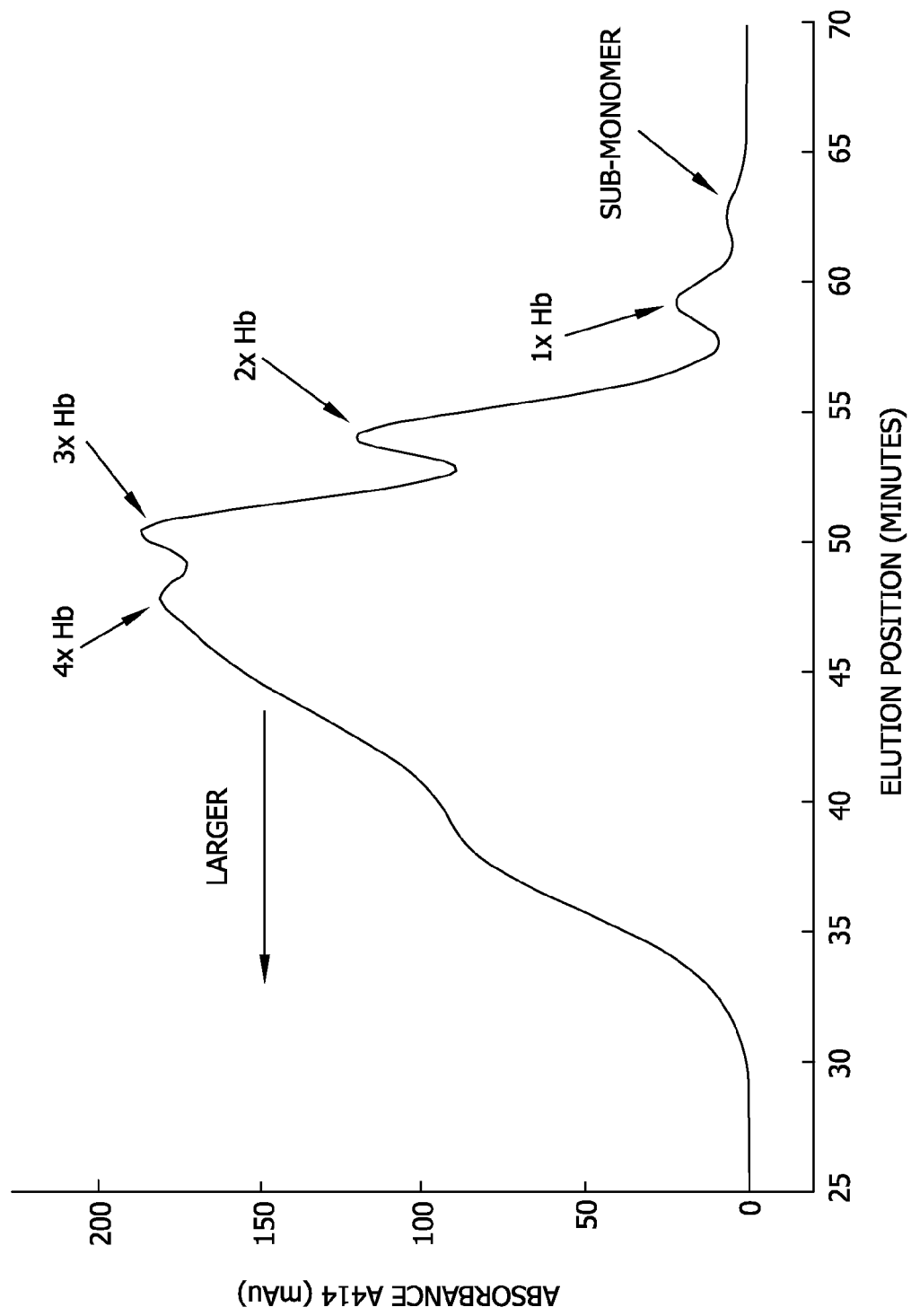
FIG. 12 is a size exclusion chromatogram of glutaraldehyde-polymerized SGE3011. Linear regression analysis of the chromatograph suggests that the majority of hemoglobin contained in glutaraldehyde-polymerized SGE3011 comprise 3 to 12 chemically crosslinked $di\alpha\beta_2$ hemoglobin monomers. Approximately 11.6% of the hemoglobin is dimerized hemoglobin, and approximately 1.8% is monomer.
Figure 13:
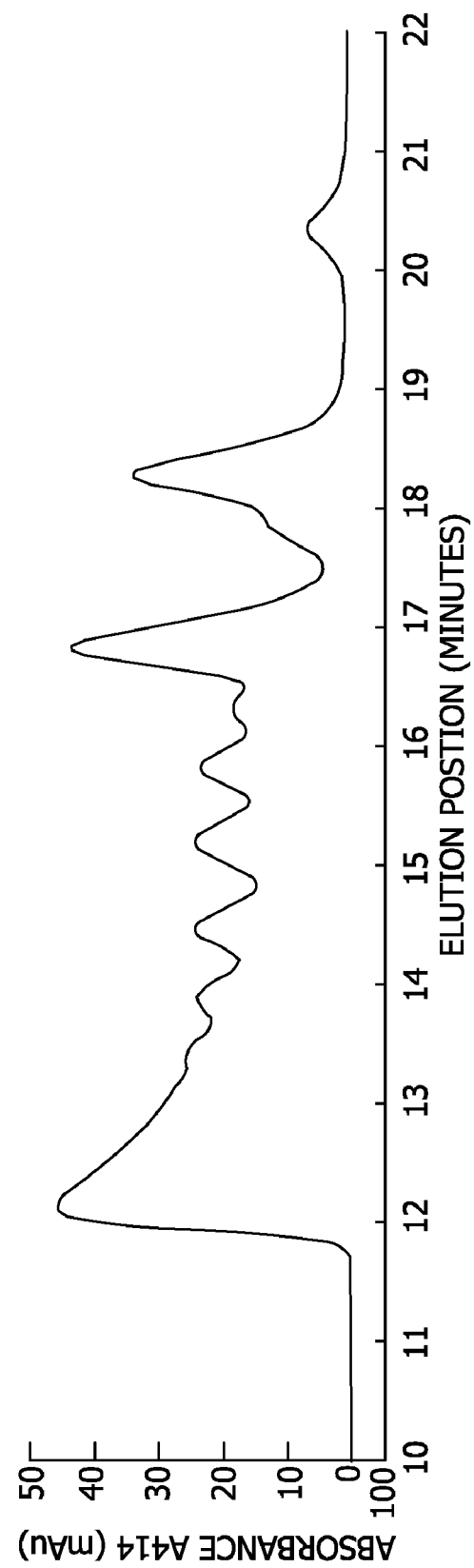
FIG. 13 is a size exclusion chromatogram of BM-PEG polymerized SGE3937. Linear regression analysis of the chromatograph suggests that the majority of hemoglobin contained in BM-PEG polymerized SGE3937 comprise three to seven chemically crosslinked $di\alpha\beta_2$ hemoglobin monomers (average 4.7). Approximately 13% of the hemoglobin is dimerized hemoglobin, and approximately 1.5% is monomer.

In one embodiment of the present invention, it is preferred that the polymerized hemoglobin has an average molecular weight between 130 kD and 500 kD, more preferably between 190 kD and 350 kD. FIG. 12, glutaraldehyde polymerized SGE3011, FIG. 13, bismaleimide polyethyleneglycol (BM-PEG) polymerized SGE3937, and FIG. 14, 4M-pentaerythritol polymerized SGE3927, illustrate molecular weight profiles for the hemoglobin composition of this embodiment of the invention. Compositions of this embodiment which comprise a majority of hemoglobins in the trimer to septamer form function as reduced side effect hemoglobins. Preferably, less than one third of the hemoglobin composition of this embodiment comprises hemoglobin dimers and monomers. More preferably, hemoglobin dimers comprise less than 20% of the hemoglobin composition, and hemoglobin monomers comprise less than 5% of the hemoglobin composition. Macromolecular hemoglobin polymers, of 20-mer size or larger, can cause the aggregation of blood cells and other biological problems. Therefore, the hemoglobin composition preferably contains no appreciable quantity of hemoglobin species which are 20-mers or larger.

Figure 15:
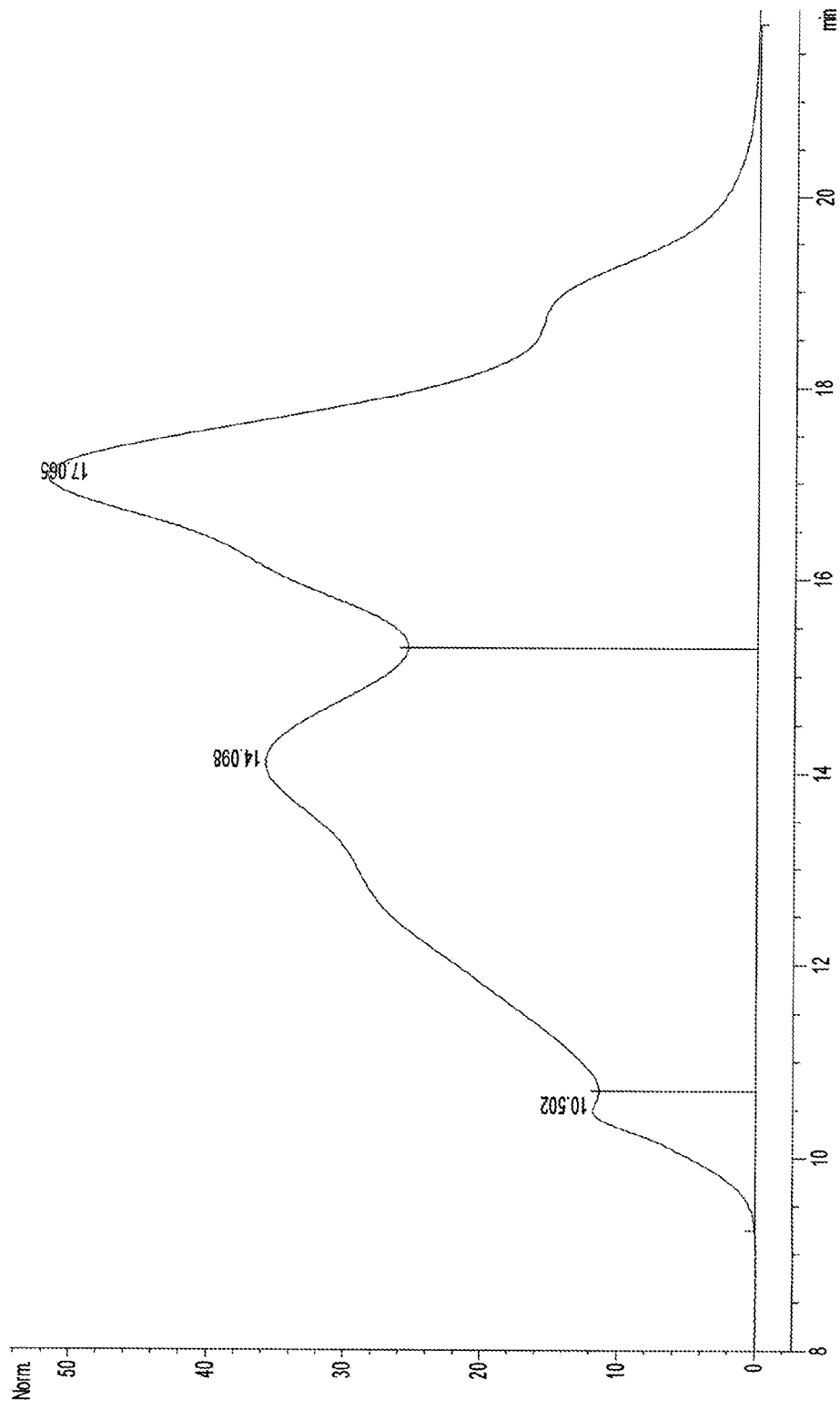
FIG. 15 is a size exclusion chromatogram of BMA-PEG polymerized SGE3959. Protein chemical analysis of the molecular species present suggests that approximately one-half of the molecules are monomers, one-third of the molecules are dimers and the remainder are trimers and higher order multimers.
Figure 16:
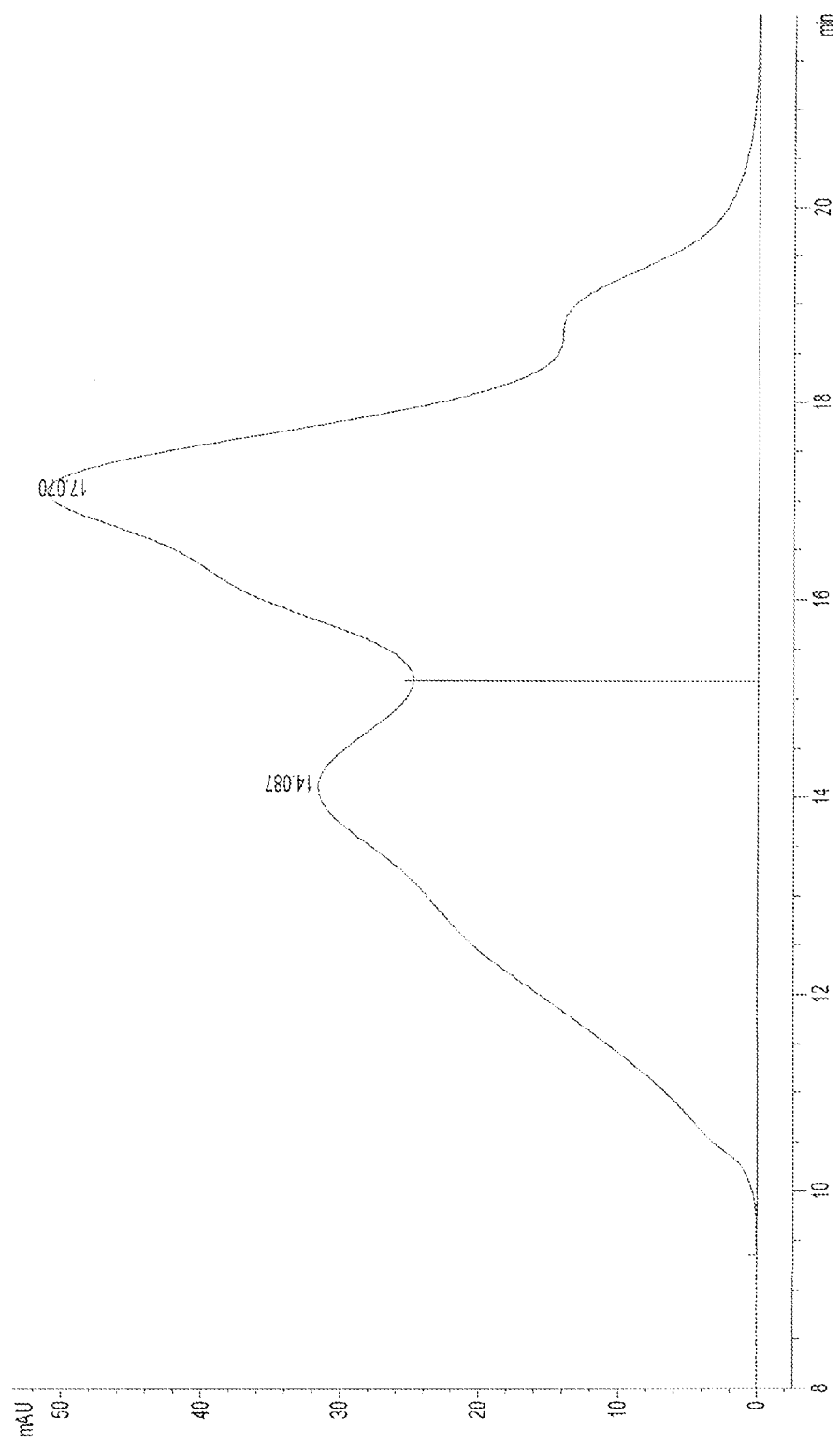
FIG. 16 is a size exclusion chromatogram of BMA-PEG polymerized SGE3487. Protein chemical analysis of the molecular species present suggests that approximately one-half of the molecules are monomers, one-third of the molecules are drimers and the remainder are trimers and higher order multimers.

In yet another embodiment, it is preferred that the polymerized hemoglobin has an average molecular weight between 65 kD and 650 kD, more preferably the hemoglobin composition has a molecular weight distribution of between 40% and 60% derivatized monomeric hemoglobin in the range of between 65 kD and less than 130 kD and the remainder as oligomeric hemoglobin in the range of between 130 kD and 650 kD. FIG. 15, BMA-PEG polymerized SGE3959, and FIG. 16 BMA-PEG polymerized SGE3487, depict molecular weight profiles for a hemoglobin composition of this embodiment of the invention. Polymerization of hemoglobin with BMA-PEG results in a heterogenous composition of polymerized hemoglobin with varying degrees of PEG-decoration (e.g. hemoglobin derivatized with PEG) as well as intra-molecular and inter-molecular PEG cross-links. The average ratio of moles of PEG molecules per mole of hemoglobin monomer is generally between 2 to 1 and 11 to 1, more preferably about 3 to 1. Compositions of this embodiment, in contrast to the hemoglobin of the embodiment set forth above, comprise a majority of hemoglobin in the monomer to trimer form to function as reduced side effect hemoglobin. Preferably, about 80% of the hemoglobin composition of this embodiment comprises hemoglobin dimers and monomers. More preferably, hemoglobin monomers comprise about 50% of the hemoglobin composition, and hemoglobin dimers comprise about 30% of the hemoglobin composition with the remainder of the hemoglobin comprising trimers and higher order multimers. However, as described in the embodiment above, Applicants have found that macromolecular hemoglobin polymers, of 20-mer size or larger, can cause the aggregation of blood cells and other biological problems. Therefore, the hemoglobin composition preferably contains no appreciable quantity of hemoglobin species which are 20-mers or larger.

A variety of chemical crosslinkers may be used to polymerize the hemoglobins of the present invention. In general, the applicants have found that any biologically inert, hydrophilic crosslinking reagent is suitable for use as a polymerizing agent. One crosslinker which has been used by the applicants is glutaraldehyde, which cross-links hemoglobin molecules between surface lysine groups. Example 6 illustrates a glutaraldehyde crosslinking procedure for the production of reduced or low side effect hemoglobins. Other protocols for glutaraldehyde crosslinking are known in the art. Although glutaraldehyde crosslinking of low nitric oxide reactivity hemoglobin produces low side effect hemoglobins, as exemplified by glutaraldehyde-polymerized SGE3011, it is not the most preferred method of crosslinking. The native hemoglobin molecule, and most mutant hemoglobins, has 42 surface lysine sites with which the glutaraldehyde crosslinking reagent can react. And, as pointed out above, glutaraldehyde will also intramolecularly crosslink hemoglobins between subunits. This tends to create a very chemically heterogenous product. Also, known glutaraldehyde crosslinked hemoglobins have caused immunogenic reactions in laboratory testing, and have been purified of monomeric hemoglobin and very large hemoglobin polymers to reduce their immunogenicity. Therefore, crosslinking reagents which are more directed and site-specific are preferred for producing the hemoglobins of the present invention.

Sulfhydryl reactive crosslinking reagents have proven preferable for polymerization. Normally, only two hemoglobin cysteine residues are reactive, the β93 residues. Thus, only two sites for sulfhydryl cross-linking naturally exist on the hemoglobin molecule. By eliminating this surface cysteine, and mutating another surface amino acid residue to cysteine, a variety of specific crosslinking sites may be created on the hemoglobin molecule, including the Porto Alegre site (S9C) used in SGE3937. Suggestions for surface cysteine mutation sites and a discussion regarding selection criteria may be found in U.S. Pat. No. 5,844,089, hereby incorporated by reference. In addition, asymmetric or symmetric cysteine mutations in a di-α subunit may be crosslinked. These surface cysteine residues may be oxidatively crosslinked to each other. Alternatively, several sulfhydryl-specific crosslinking reagents have been developed for use with cysteine residues on proteins. Bismaleimide polyethylene glycols have been used by the applicants, as described in Examples 7, 21 and 22 to polymerize SGE3959 (at β C93), SGE3487 (at β C93) and SGE3937 (at β S9C). In addition, other sulfhydryl-reactive reagents such as vinyl sulfones, and pentafluorobenzene sulfamates may be used to crosslink the surface cysteines of the recombinant hemoglobins used in the invention.

Figure 14:
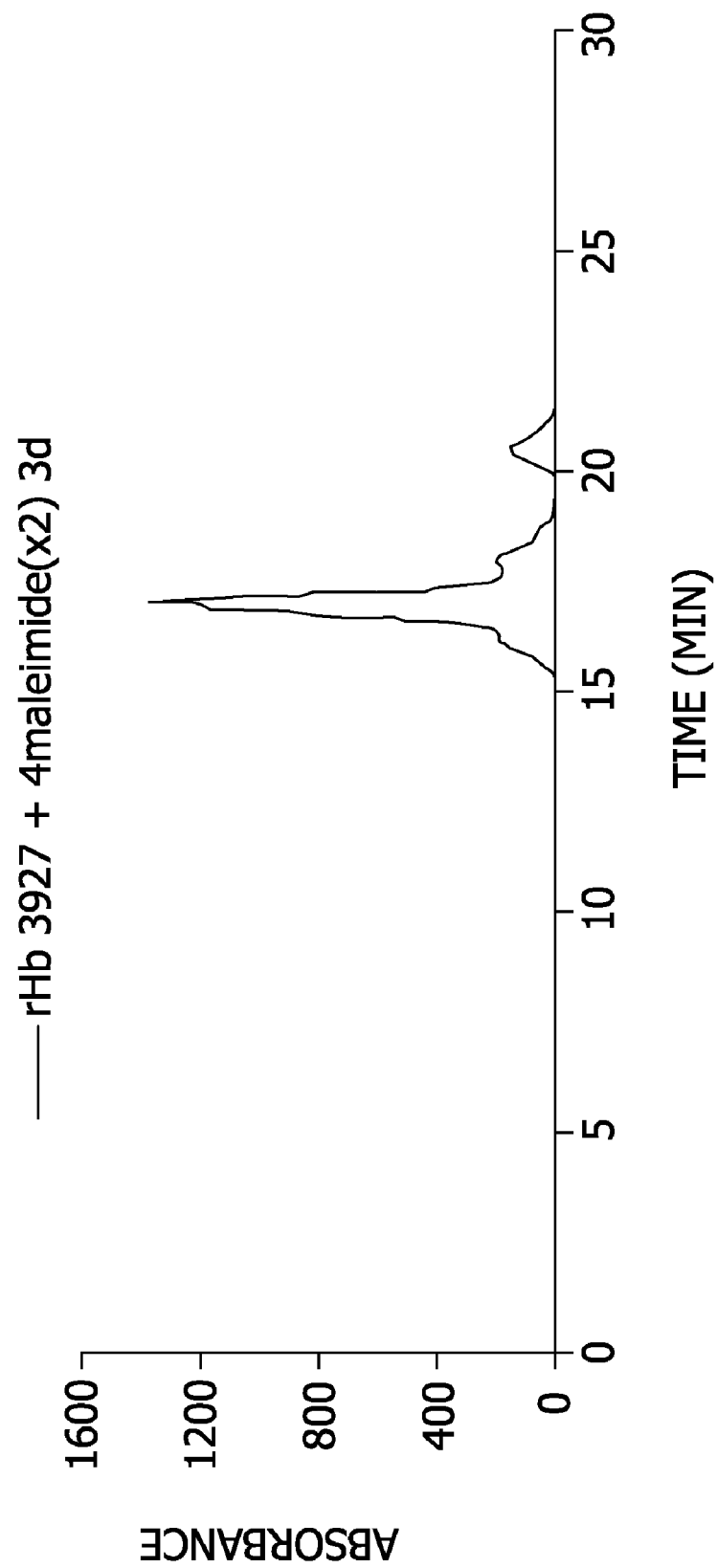
FIG. 14 is a size exclusion chromatogram of 4M-pentaerythritol polymerized SGE3927. Linear regression analysis of the chromatograph suggests that 9.2% of the polymer is tetrahb, 74.4% of the polymer is triHb, 10.0% of the polymer is dihb, and only 6.4% is monomeric Hb.

Linkers used for polymerization of the hemoglobins of the present invention may be of varying sizes. Shorter linkers, such as $BM(PEG)_3$, may be useful if circularization of the monomer by reaction of both sulfhydryl reactive groups of the crosslinker with cysteines on the same hemoglobin, is to be avoided. If shorter linkers are used, they need to span the distance between the crosslinked hemoglobins to prevent steric strain. In linking the p S9C site between two hemoglobins, for instance a linker which is about 14–17 angstroms in length should be used. In addition to bifunctional crosslinkers, polyfunctional crosslinkers may be used as well to produce the hemoglobins of the present invention. For instance, the applicants have used tetrakis-(3-maleimidopropyl)pentaerythritol, a four armed polyfunctional linker agent, to polymerize SGE3927 at an asymmetrical cysteine in the di a subunit, as described in Example 20. Crosslinking with this molecule creates a primarily trimeric polymerized hemoglobin. Applicants expect that utilizing linkers with longer "arms," in order to overcome probably steric interference in crosslinking, would create tetrameric products. The advantages of a polyfunctional/asymmetric di a mutant strategy is that a more homogenous hemoglobin composition can be obtained. The applicants obtained over 70% of a single species, as illustrated in FIG. 14. Polyfunctional linkers with other sulfhydryl reactive groups, such as vinyl sulfones (e.g., tetra(vinyl sulfone) PEG or glycerol (PEG-vinyl sulfone)$_3$), could also be used.

The Administration of Reduced Side Effect Hemoglobin as a Blood Substitute

The present invention provides for the use of reduced side effect hemoglobins in compositions useful as substitutes for red blood cells for any application in which oxygen delivery is desired or red blood cells are used. The reduced side effect hemoglobins can also be formulated as oxygen carrying therapeutics and used for the treatment of hemorrhages, traumas and surgeries where blood volume is lost and either fluid volume or oxygen carrying capacity or both must be replaced. Reduced side effect hemoglobins can also be used as replacement for blood that is removed during surgical procedures where the patient's blood is removed and saved for reinfusion at the end of surgery or during recovery (acute normovolemic hemodilution or hemoaugmentation). In addition, the reduced side effect hemoglobins of the instant invention can be used to increase the amount of blood that can be predonated prior to surgery, by acting to replace some of the oxygen carrying capacity that is donated. Moreover, because the reduced side effect hemoglobins of the instant invention can be made pharmaceutically acceptable, they can be used not only as blood substitutes that deliver oxygen but also as simple volume expanders that provide oncotic pressure due to the presence of the large hemoglobin protein molecule.

As a guideline for the use of reduced side effect hemoglobins as blood substitutes according to the present invention, a 10% solution of reduced side effect hemoglobin should be infused at a rate of 1 ml/kg/hour to the desired total patient blood volume. The person of ordinary skill in the art treating the patient would be able to make a determination as to the desirable total patient blood volume. In the case of an emergency transfusion in a trauma setting, the amount infused would often be approximately the blood volume lost in order to maintain normovolemia. However, in preoperative circumstances, the recombinant reduced side effect hemoglobin solution should be used similarly to a crystalloid solution. An amount of recombinant reduced side effect hemoglobin solution between about 1 ml and 100 ml per kilogram of patient weight of recombinant hemoglobin solution may be administered intravenously or intraarterially as a bolus injection or as a continuous infusion to induce the desired hypervolemic state. When used to prime a cardiac pump or other machinery in preparation for surgery, the recombinant hemoglobin solution should be used similarly to whole blood. In addition, the blood substitute compositions may be used in other ex vivo applications where oxygenation is desired, such as the perfusion of organs for transplant.

The Administration of Reduced Side Effect Hemoglobin to Treat Hypovolemia or Shock In one embodiment of the invention, pharmaceutical compositions comprising recombinant hemoglobin of the invention may be used to treat hypovolemic or hemorrhagic conditions, with or without concurrent shock. In addition, these compositions may be used to treat cardiogenic shock. The usefulness of these compositions in this capacity stems from the fact that normovolemic conditions may be restored with a solution which both carries oxygen in physiologically beneficial quantities, and provides sufficient oncotic pressure to maintain the vascular pressure of the patient. In addition, the preferred embodiments of the invention, comprising reduced side effect hemoglobins, do not produce heart lesions, or induce a nitric oxide mediated pressor effect.

As a general guideline for treating hypovolemia or hypovolemic shock, from about 50–100 ml up to the total estimated lost blood volume of 10% reduced side effect hemoglobin solution should be injected intravenously as a bolus. Preferably, the reduced side effect hemoglobin is administered at a dose of about 100 to about 7,500 mg/kg of body weight, more preferably about 500 to about 5,000 mg/kg of body weight. most preferably about 700 to about 3,000 mg/kg of body weight. The reduced side effect hemoglobin is preferably administered during the first three hours after the development of a shock state. The reduced side effect hemoglobin solution is most preferably injected within the first, or "golden," hour of the shock state to minimize the duration of decreased oxygen delivery. Cuff blood pressure should be monitored at routine intervals until stabilized. Other cardiopulmonary parameters should also be monitored according to standard practice. Other standard therapeutics may be administered , as desired or indicated. In cases of acute hypovolemia, re-administration of reduced side effect hemoglobin solution or transfusion with whole blood within the window of reduced side effect hemoglobin retention in the system of the patient may be necessary.

As a guideline for treating conditions of cardiogenic shock, the practitioner should inject one or more 50 ml (5000 mg) IV boluses, and/or infuse up to 6000 ml (300 g) of 10% hemoglobin solution (or equivalent) at a rate of 1 ml/kg/min to achieve and maintain the desired effect. The reduced side effect hemoglobin is most preferably administered as early as possible after the development of a shock state to minimize the duration of decreased perfusion. Blood pressure should be monitored (directly or indirectly) every 15 minutes after administration until peak pressure is obtained. Other cardiopulmonary parameters may be monitored according to standard practice. Other standard therapeutics may be administered, as desired or indicated.

The Administration of Reduced Side Effect Hemoglobin to Increase Tissue Perfusion in order to Treat Stroke, Ischemia, or Tissue Damage Another aspect of the present invention relates to perfusion of tissues, and specifically to the therapeutic use of hemoglobin in low doses to increase tissue perfusion.

Perfusion is supplying an organ or tissue with oxygen and nutrients via blood or a suitable fluid through arteries and capillaries. Flow may be expressed as the ratio of pressure to resistance. If adequate oxygen and nutrients are not reaching tissues and organs, therapies to improve perfusion may be employed. This invention provides a method to therapeutically increase perfusion in a mammal comprising administering reduced side effect hemoglobin at a dose ranging from about 30 mg to about 15,000 mg per kilogram of body weight. Preferably, the reduced side effect hemoglobin is administered at a dose of about 100 to about 7,500 mg/kg of body weight, more preferably about 500 to about 5,000 mg/kg of body weight. most preferably about 700 to about 3,000 mg/kg of body weight.

An advantage of using the preferred reduced side effect hemoglobins of the invention is that perfusion of tissues can be increased without inducing a nitric oxide mediated pressor effect or the creation of heart lesions. The increase in tissue perfusion is partially due to the ability of the relatively small hemoglobin molecules to bypass clots and obstructions which erythrocytes cannot. Applicants do not limit themselves to these theories of action, however, and contemplate the possible existence of other mechanisms for the increased perfusion effect.

The use of the present invention to increase tissue perfusion has many clinical implications. A primary application is in stroke victims, in order to allow for brain tissue oxygenation distal to the vessel clot until it is dissolved naturally or by therapeutic interventions. Other instances of tissue ischemia, especially cases of myocardial ischemias, would benefit from the increased tissue perfusion offered by the present invention. It has also been found that patients who have been exposed to tissue damage, such as burns and wounds, can greatly benefit from increased perfusion of the damaged tissue, which increases available oxygen for repair of the damage.

Use of hemoglobin to maintain adequate perfusion in a critical care setting involves slow infusion of a crystalloid/hemoglobin solution to deliver a minimum of about 30 mg hemoglobin per kg of body weight. The dose administered should give a rise in mean arterial blood pressure about equal to normal physiologic levels. As used herein the term blood pressure shall mean the mean arterial blood pressure.

As a guideline for the treatment of a patient to increase perfusion in stroke conditions, or to treat other ischemias or tissue damage, at least 200 ml (20 g) of 10% reduced side effect hemoglobin (or equivalent) should be infused intravenously at a rate of 1 ml/kg/min to achieve and maintain the desired perfusion effect. Administration of the recombinant hemoglobin solution should begin as early as possible following the cerebrovascular accident to minimize the duration of decreased cerebral perfusion, in instances of stroke. When treating other ischemic disorders, the infusion of hemoglobin should likewise be administered as quickly as possible after the onset of the ischemic event. Cardiopulmonary parameters may be monitored according to standard practice. Other standard therapeutics may be administered as desired or indicated.

The Administration of Reduced Side Effect Hemoglobin in the Management of Sickle Cell Anemia Patients Sickle Cell Crisis. As a guideline for the use of the reduced side effect hemoglobin as an oxygen carrying hemoglobin therapeutic according to the present invention, a 10% solution of the hemoglobin should be infused intravenously as a bolus administration of 100–3,000 ml. The hemoglobin solution can either be administered as a topload (additional to present blood volume) or as a volume replacement (e.g. blood loss, volume exchange or acute normovolemic hemodilution). The physician care-giver skilled in the art of evaluating sickle cell anemia patients would initiate therapy with the hemoglobin solution immediately upon the patient's presentation of sickle cell crisis (vasoocclusive crisis). Alternately, hemoglobin therapy would be initiated upon presentation of a sickle cell anemia patient suffering from another illness (e.g., infection, fever, hypoxia) which would have an associated reasonable expectation for the development of an acute sickle cell crisis. The hemoglobin would be administered with a therapeutic aim of enhancing oxygen delivery to the tissues and vital organs. The desired beneficial endpoints would include: relief of pain; decreased requirements for analgesic medications; shortened hospitalization; avoidance or diminishing of pulmonary complications (e.g. acute chest syndrome); and, avoidance or diminishing of major end-organ vasoocclusive events (e.g. acute ischemic stroke).

Acute Ischemic Stroke associated with Acute Sickle Cell Crisis. As a guideline for the use of the reduced side effect hemoglobin as an oxygen carrying hemoglobin therapeutic according to the present invention, a 10% solution of the hemoglobin should be used intravenously as a bolus administration of 100–3,000 ml. The hemoglobin solution can either be administered as a topload (additional to present blood volume) or as a volume replacement (e.g., volume exchange or acute normovolemic hemodilution). The physician care-giver skilled in the art of evaluating sickle cell anemia patients would initiate therapy with the hemoglobin solution immediately upon the patient's presentation of an acute cerebral ischemic event associated with a sickle cell crisis (vasoocclusive crisis). The hemoglobin would be administered with a therapeutic aim of enhancing oxygen delivery to the ischemic area of the brain. The desired beneficial endpoints would include significant reduction in the neurologic sequelae, morbidity and mortality associated with the acute ischemic stroke episode.

Preoperative preparation for Sickle Cell Anemia patients. As a guideline for the use of the reduced side effect hemoglobin as an oxygen carrying hemoglobin therapeutic according to the present invention, a 10% solution of the hemoglobin should be infused intravenously as a bolus administration of 100–3,000 ml. The hemoglobin solution can either be administered as a topload (additional to present blood volume) or as a volume replacement (e.g. blood loss, volume exchange or acute normovolemic hemodilution). The physician care-giver skilled in the art of evaluation sickle cell anemia patients would initiate therapy with the hemoglobin solution prior to elective or emergency surgery. The hemoglobin would be administered with a therapeutic aim of enhancing oxygen deliver to the tissues and vital organs an prevention of the precipitation of sickle cell crisis (vasoocclusive crisis). The desired beneficial endpoints would include: prevention of a post-operative sickle cell crisis; decreased requirements for analgesic medications; shortened hospitalization; avoidance or diminishing of pulmonary complications (e.g. acute chest syndrome); and, avoidance or diminishing of major end-organ vasoocclusive events (e.g. acute ischemic stroke).

The Administration of Reduced Side Effect Hemoglobin to Treat Anemia, Stimulate Hematopoiesis, and Alleviate Cachexia The present invention also relates to a method of stimulating hematopoiesis in a mammal comprising administration of a therapeutically effective amount of an essentially pure reduced side effect hemoglobin. Pharmaceutical preparations of reduced side effect hemoglobins can be useful, either alone or in combination with other components, to stimulate hematopoiesis; or to treat mammals suffering from a cytopenia, such as anemia or thrombocytopenia;

Acute blood losses such as menstruation, trauma or surgical blood loss may result in anemia wherein the blood is deficient in red blood cells, in hemoglobin or in total volume (hematocrit <40%, hemoglobin <12 grams/dl, red blood cells <4×106/ul, or mean cell volume <80 fl; Nathan, D. G. (1992) in *Cecil Textbook of Medicine*, J. B. Wyngaarden, L. H. Smith and J. C. Bennett, ed., W. B. Saunders Co., Philadelphia, pages 817–836). The red cell mass (total red blood cells, either total number, weight or volume) acts as an organ that delivers oxygen to tissues. Red cell mass and the rate of red blood cell production are closely coupled to the supply and demand for oxygen in body tissues. Red blood cell production is stimulated by low tissue tension of oxygen. Anemic conditions result in reduced oxygen levels in tissues (hypoxia). Hypoxia in the kidney is sensed by the renal parenchyma which stimulates the release of erythropoietin from the kidney. Erythropoietin is the major regulatory hormone of erythropoiesis produced in response to hypoxia resulting from alterations in the red cell mass. (Erslev, A. J. (1990) in *Hematology*, W. J. Williams, E. Beutler, A. J. Erslev and M. A. Lichtman eds, McGraw-Hill, Inc. New York, pp 389–407). In chronic renal failure there is inadequate production of erythropoietin resulting in only marginal erythropoiesis and symptomatic chronic anemia.

Other deficits in specific circulating cell types may occur as well. Leukopenia, a general term that describes decreases in any one of a number of different leukocyte cell populations, may result from a de-coupling of the process of demargination and the rate of replacement of cells differentiated from progenitor bone marrow cell lines (Bagby, G. C. (1992) in *Cecil Textbook of Medicine*, J. B. Wyngaarden, L. H. Smith and J. C. Bennett, ed. W. B. Saunders Co., Philadelphia, pages 914–920). Neutropenia, a decrease in circulating neutrophils to <2×109 cells per liter, results in a greatly increased risk of severe bacterial infection (Kaplan, M. E. (1992) in *Cecil Textbook of Medicine*, J. B. Wyngaarden, L. H. Smith and J. C. Bennett, ed. W. B. Saunders Co, Philadelphia, pages 907–914). Thrombocytopenias are defined as decreases in circulating platelet levels to approximately <100,000/ml (Shuman, M. (1992) in *Cecil Textbook of Medicine*, J. B. Wyngaarden, L. H. Smith and J. C. Bennett, ed. W. B. Saunders Co, Philadelphia, pages 987–999). Low circulating thrombocytes may be the result of a number of underlying conditions such as bone marrow injury, the utilization of chemotoxic agents, suppression of the bone marrow due to chemotherapeutic or radiotherapeutic agents, heavy metal poisoning, hemolytic uremic syndrome, HIV infection, tuberculosis, aplastic anemia, thrombotic thrombocytopenic purpura, and immune disorders such as idiopathic thrombocytopenic purpura, leukemias, and myelofibrosis. These thrombocytopenias can result in life-threatening uncontrolled bleeding (Shuman, M. (1992) in *Cecil Textbook of Medicine*, J. B. Wyngaarden, L. H. Smith and J. C. Bennett, ed. W. B. Saunders Co, Philadelphia, pages 987–999).

Hematopoiesis is the process of blood cell production which takes place in the bone marrow. Stem cells in the bone marrow are the progenitor cells for all of the various cell types found in the circulating blood. These stem cells are functionally defined by their capacity to repopulate, on a long-term basis, all of the hematopoietic cell lineages in a lethally irradiated animal [Nicola, N. A. (1993) in Application of Basic Science to Hematopoiesis and the Treatment of Disease, E. D. Thomas and S. K. Carter (ed), Raven Press, NY]. Through a complex series of regulatory events, stem cells differentiate into a number of types of cells including at least red blood cells, leukocytes, lymphocytes, platelets (thrombocytes), monocytes, macrophages, mast cells, basophils, eosinophils, B-lymphocytes and T-lymphocytes. Millions of each type of new blood cells are produced daily and are released into the circulating blood to replace destroyed blood cells and maintain homeostasis. (Nathan, D. G. (1992) in *Cecil Textbook of Medicine*, J. B. Wyngaarden, L. H. Smith and J. C. Bennett, ed., W. B. Saunders Co, Philadelphia, pages 817–836).

The hemoglobin of the present invention is useful for the treatment of cytopenia in a mammal. Administration of low doses of reduced side effect hemoglobin according to the present invention will alleviate cytopenias caused by any of the above conditions. The present invention is particularly useful in reversing the cytopenias induced by AZT therapy, and moreover ameliorating the accompanying cachexia caused by either the AZT therapy or the AIDS disease.

The therapeutically effective quantity of pharmaceutical provided to the individual is sufficient to provide a blood concentration of between 0.0001 micromolar and 1 millimolar of hemoglobin. In contrast to Feola et al., (1992) Surg. Gyn. Obstet. 174: 379–386, who injected over 1.7 gm of hemoglobin per kilogram body weight, the method of the present invention results in hematopoiesis at a low dose of hemoglobin, typically from about 1 ng to 1 gram of hemoglobin per kilogram of patient body weight. Dosages can be from about 0.001–1000 mg hemoglobin/kg body weight, more preferably 0.01 mg-100 mg hemoglobin/kg body weight, most preferably 1 mg to 10 mg hemoglobin/kg body weight. It will be appreciated that the unit content of active ingredients contained in an individual dose of each dosage form need not in itself constitute an effective amount since the necessary effective amount can be reached by administration of a plurality of capsules, tablets, injections, etc. or combinations thereof.

Administration of hemoglobin can occur for a period of minutes to weeks; however the usual time course is over the course of several weeks to gain maximum hematopoietic effect and ameliorate the course of a cytopenia. Typical administration regimes can be from about one to ten weeks, more preferably four to nine weeks, most preferably six to eight weeks. Dosages of hemoglobin can be administered at a frequency of 1 to 7 times per week, more preferably 2 to 5 times per week, most preferably 3 times per week.

The present invention also contemplates the use of additional hematopoietic factors, which when administered in combination with purified hemoglobin, stimulate hematopoiesis to a degree greater than either therapeutic compound alone. Examples of such additional hematopoietic factors include but are not limited to Granulocyte-Macrophage Colony Stimulating Factor (GM-CSF), Macrophage Colony-Stimulating Factor (M-CSF), Granulocyte Colony-Stimulating Factor (G-CSF), Stem Cell Factor (SCF), Erythropoietin (EPO) and Interleukins 1–13 (IL1 to IL13) (Souza, L. M., U.S. Pat. No. 4,810,643; Clark, S. C. and Wong, G. G., U.S. Pat. No. 4,868,119; Blasdale, J. H. C., European Patent EP 355093; Quesenberry, P. J in *Hematology*, W. J. Williams, E. Beutler, A. J. Erslev and M. A. Lichtman (eds) 1990, McGraw-Hill, Inc. New York, pp 129–147; Lin, U.S. Pat. No. 4,703,008; Zsebo, K. M. et al., PCT/US90/05548; Nicola, N. A. (1993) in *Application of Basic Science to Hematopoiesis and the Treatment of Disease*, E. D. Thomas and S. K. Carter (ed), Raven Press, NY; Deeley M., et al., U.S. Pat. No. 5,023,676).

Hemoglobin of the invention can be administered in combination with other hematopoietic factors in the same dosage formulation or individually to achieve maximum therapeutic effect. The optimal dosage regime can be determined by clinicians of ordinary skill in the art.

The Administration of Reduced Side Effect Hemoglobin to Treat Head Injury

The present invention also provides a method for treating head injury in a mammal, comprising administering to a mammal suffering from a head injury an effective amount of a reduced side effect hemoglobin preparation.

Useful doses of hemoglobin for the treatment of head injuries according to the present invention are those that are effective in reducing or eliminating the increase in intracranial pressure (ICP) and/or decrease in cerebral perfusion pressure (CPP) frequently observed following head injury. Hemoglobin doses which effectively reduce intracranial pressure and elevate cerebral perfusion pressure include the range of from about 100 to about 7,500 mg/kg of body weight, more preferably about 500 to about 5,000 mg/kg of body weight. most preferably about 700 to about 3,000 mg/kg of body weight.

Administration of an effective amount of hemoglobin to reduce or eliminate increases in ICP associated with head injury and/or increase CPP by the method of the present invention can be carried out parenterally, for example by intravenous or intraarterial injection, infusion, or arterial cannulization (in appropriate clinical circumstances), peritraumatically or perioperatively. Such effective amount can be administered in a single dose, or in a series of multiple subdoses. The single dose or each of said multiple subdoses can be administered by slow continuous infusion. Administration of hemoglobin to control increases in ICP and/or to increase CPP in head-injured patients can be via such single dose, or multiple subdoses, given within about one minute to about 48 hours after occurrence of the injury, more preferably within about one minute to about 12 hours, most preferably within about one minute to about 3 hours. After initial administration of an effective amount of a hemoglobin preparation, at least one additional effective amount of a hemoglobin preparation can be administered in the same manner as described herein for the initial dose.

The Administration of Reduced Side Effect Hemoglobin to Enhance Cancer Therapies The present invention provides methods of enhancing the effectiveness of cancer treatments such as radiation and/or chemotherapeutic agent therapies. Methods of reducing tumor burden in mammals are also provided. The methods include administering to a mammal in need of such therapy or therapies an effective amount of reduced side effect hemoglobin in combination with a cancer therapy. While the applicants do not hold themselves to any particular theory of the mechanism of this indication, it is thought that the increased oxygenation of the normally hypoxic tumor mass by increased perfusion to the tumor increases the efficacy of radiation and chemotherapies. A significant reduction in the tumorous condition results.

For purposes of the present invention, cancer therapy is understood to mean a therapy specifically designed to combat neoplastic growth. The therapy preferably connotes either radiation or chemotherapy, and combinations thereof. The hemoglobin is preferably administered in combination with a form of radiation therapy and/or chemotherapy. The combination→of therapies principally includes administering the hemoglobin prior to, or, at about the same time as the other cancer therapies.

A parenteral therapeutic composition may comprise a sterile isotonic saline solution containing between 0.1 percent and 90 percent weight to volume of reduced side effect hemoglobin. A preferred extracellular hemoglobin solution of recombinant hemoglobin contains from about 5 percent to 20 percent. The amount of the hemoglobin administered is an amount which significantly enhances cancer therapy. Evidence of enhancement can be deduced by observation or by analytical measurements of increased local muscle/tissue/organ oxygen levels using apparatus designed for such purpose.

As a general guideline, reduced side effect hemoglobin is administered in amounts ranging from about 100 to about 7,500 mg/kg of body weight, more preferably about 500 to about 5,000 mg/kg of body weight. most preferably about 700 to about 3,000 mg/kg of body weight.

Recombinant Mutant Hemoglobins which Prevent Hemoglobin Aggregate Formation

The present invention is also directed to recombinant mutant hemoglobins which are resistant to aggregate formation when stored as deoxygenated solutions for prolonged periods of time. As mentioned above, a common problem encountered with extracellular hemoglobin solutions for therapeutic applications is the formation of aggregates and precipitate over the shelf-life of the therapeutic composition. As the product will be given to a patient intravenously, such aggregates can cause complications if not removed prior to use in a patient. Although chemical additives such as antioxidants and detergents can prevent the formation of hemoglobin aggregates, these additives can also cause adverse reactions in some patients. Therefore, it is desirable to reduce hemoglobin aggregation in solution over the shelf-life of the hemoglobin solution.

Sickle cell mutant hemoglobin (β6 Glu→Val) is known to form aggregates in the deoxy state, creating a gel structure. The primary interaction responsible for gelation occurs between the β6 region and a hydrophobic pocket at the E-F region of the β chain (β85–88). Mutations in this hydrophobic pocket have been studied in conjunction with the sickle cell mutation (Lattupally, et al., *Biochemistry* 36: 15992–98 (1997)). In that study, it was found that the β Thr→Asp mutation and the β Thr→Trp mutation inhibited the formation of aggregates in sickle cell mutant hemoglobin.

Figure 11:
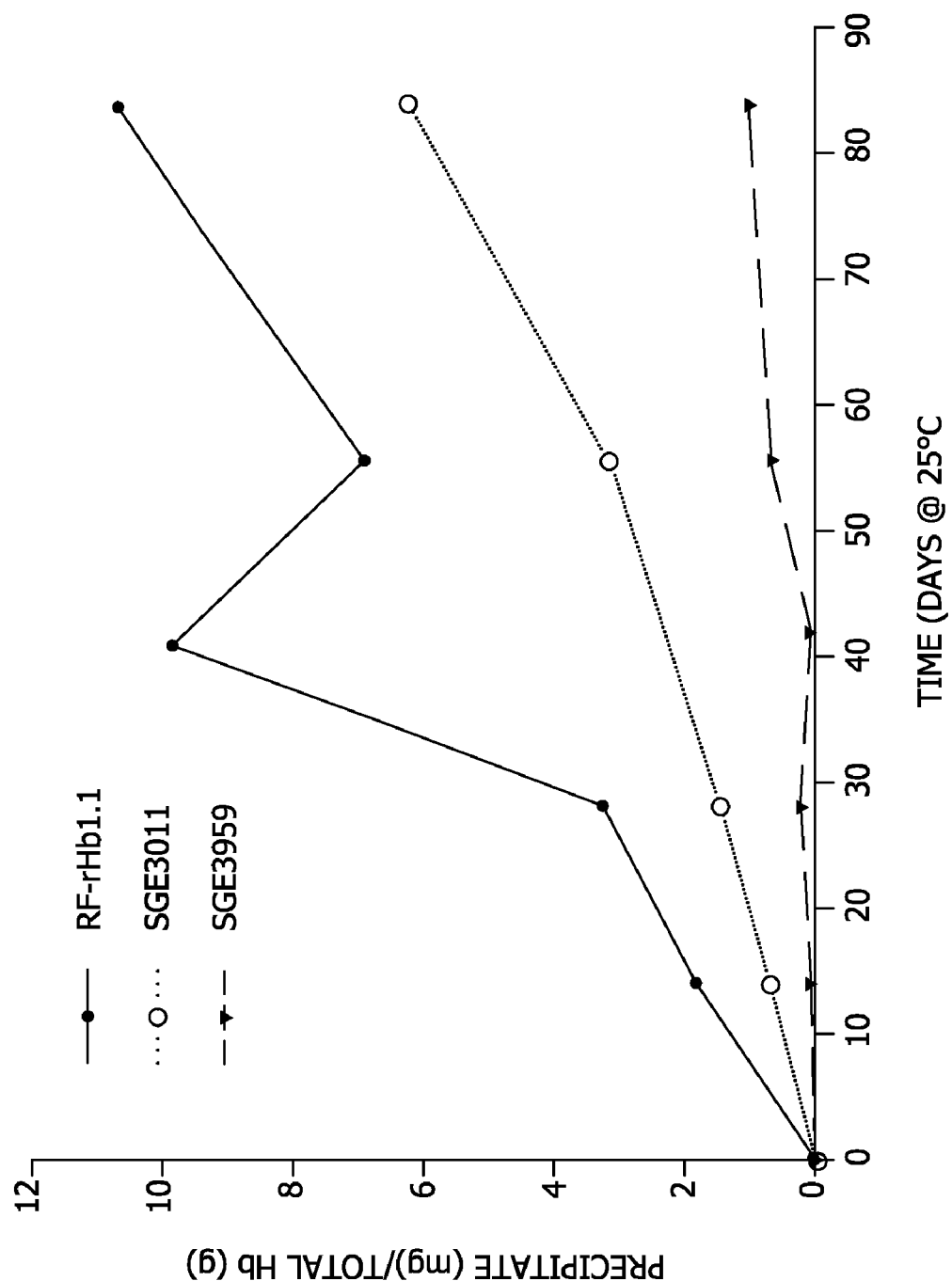
FIG. 11 depicts the comparison of precipitate formation of hemoglobin variants. Hemoglobin compositions containing rHB1.1, SGE3011, and SGE3959 were tested for the formation of hemoglobin aggregates and precipitate over a period of three months. Solutions of all three hemoglobins were stored at a constant temperature of 25° C. for three months and 25 mL samples of each hemoglobin solution were taken at 2, 4, 6, 8, and 12 weeks. Amount of precipitate is expressed as milligrams of precipitate (mg PPT) per gram of total hemoglobin in the sample (gTHb).

Applicants have discovered that mutations which may disrupt this surface hydrophobic pocket can also reduce the formation of aggregates in non-sickling hemoglobins. Specifically, replacing the threonine at position 87 with a hydrophilic amino acid, or the sterically bulky amino acid tryptophan, disrupts the surface hydrophobic pocket, and reduce the aggregation of hemoglobin in solution when stored for extended periods. As shown in FIG. 11, rHb1.1 and SGE3011, which contain a native β subunit hydrophobic pocket, accumulate increasing amounts of aggregated hemoglobin in solution when stored for 90 days. As also demonstrated in FIG. 11, the presence of the β87 Thr→Gln mutation prevents aggregate formation in the SGE3011 molecule. Similar hydrophilic amino acid substitutions would similarly prevent the recombinant mutant hemoglobin from forming aggregates during long term storage. Thus, preferred hemoglobins comprise a mutation chosen from the group consisting of β87 Thr→Asp, Glu, Arg, Lys, His, Tyr, Gln, or Trp. More preferably, such hemoglobins comprise a mutation chosen from the group consisting of β87 Thr→Asp, Gln, Glu, Arg, Lys, or His. Most preferably, such hemoglobins comprise the mutation β87 Thr→Gln. Construction of the β87 Thr→Gln mutant, and the evaluation of hemoglobin aggregation, are described in Examples 3 and 8, below.

EXAMPLE 1

Genetic Construction of Nitric Oxide Mutants

Mutations were introduced into cloned human alpha and beta genes via site directed PCR-based mutagenesis as described in general by Innis et al., *PCR Protocols: A Guide to Methods and Applications* (1990), incorporated herein by reference. In general, the desired mutations were introduced into synthetic DNA oligonucleotides which were synthesized according to the manufacturer's instructions on an Applied Biosystems 392 DNA synthesizer. Following standard deblocking procedure, oligonucleotides were dried by vacuum-centrifugation, resuspended in the desired buffer and diluted to 10–50 pmol/μl in sterile water.

These oligonucleotides were used as primers in PCR reactions where a recombinant plasmid carrying cloned wild type alpha and beta genes, such as pSGE728 (FIG. 1), was used as template DNA. The nature and construction of pSGE728 are described in detail in WO98/50430, which is incorporated herein by reference.

Figure 2:
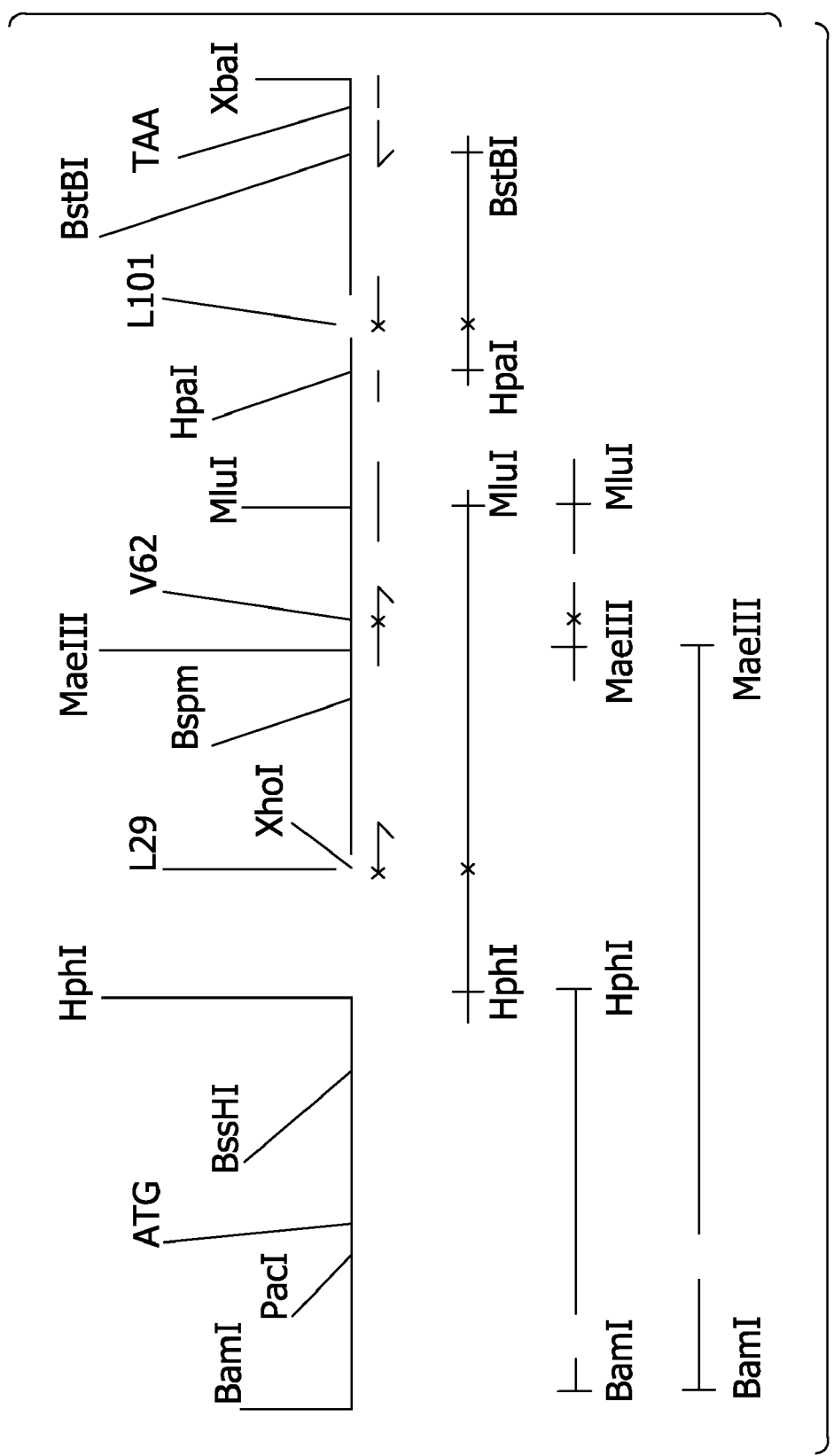
FIG. 2 shows the partial restriction map of the alpha gene inserted into pSGE728.
Figure 3:
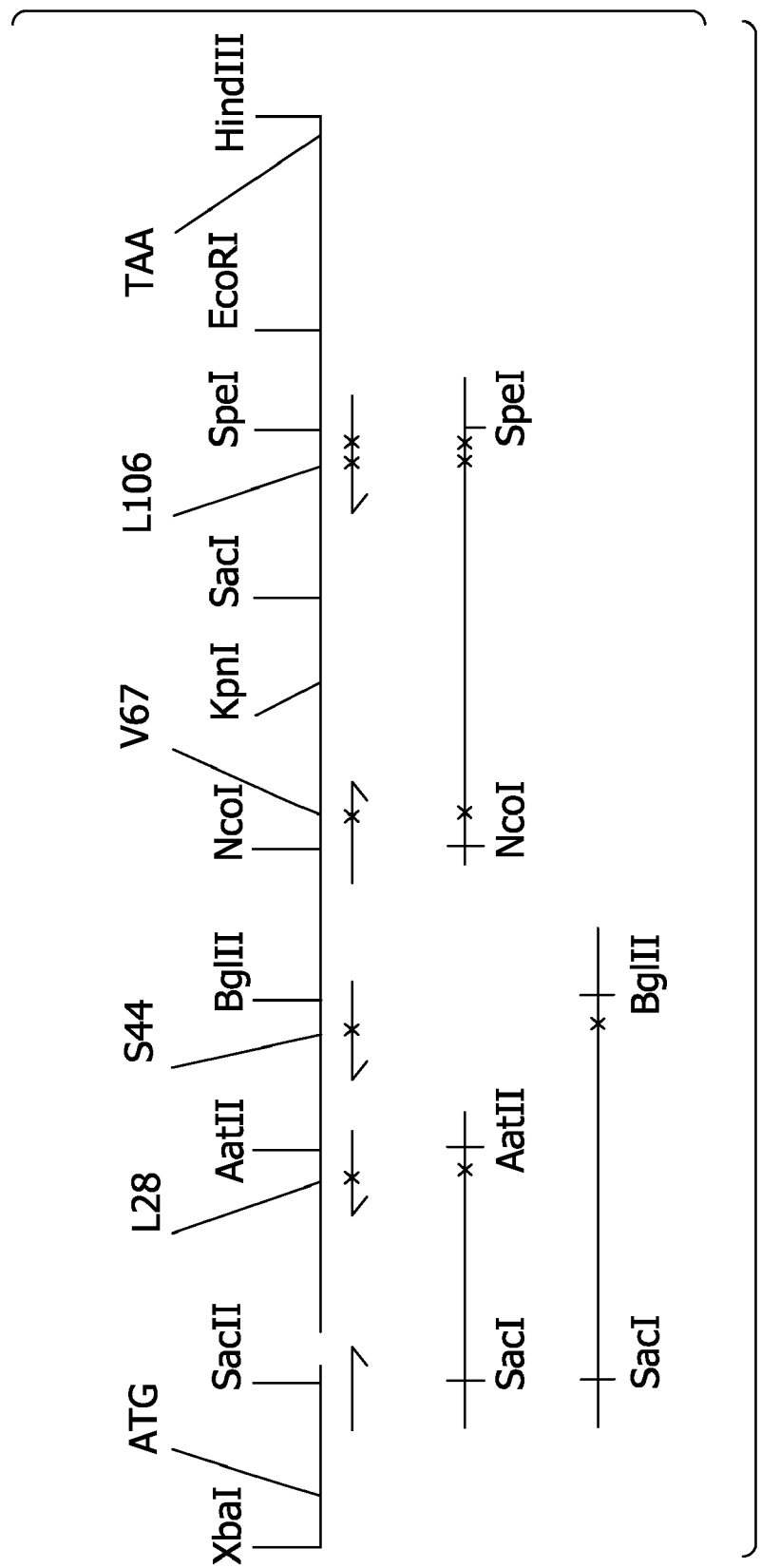
FIG. 3 shows the partial restriction map of the beta gene inserted into pSGE728.
Figure 4:
FIG. 4 is a photomicrograph which shows normal muscle tissue from the left ventricle of a rhesus monkey, 200× magnification. Note the orderly packing of muscle cells, forming the pattern of striated muscle fiber. Also note the lack of lymphocytes and macrophages in normal muscle cell tissue. A monkey whose entire heart consisted of such normal tissue, free of lesions, would receive a heart lesion severity score of "0."
Figure 5:
FIG. 5 is a photomicrograph which shows a minimal heart lesion in muscle tissue from the left ventricle of a rhesus monkey, 200× magnification. Note that the lesion area appears disordered compared to the surrounding normal, striated, muscle tissue, and that the boundaries between the cells in the lesion are no longer distinct. In addition, note the presence of lymphocytes and macrophages in the lesion, seen here above the arrow. The presence of damaged cells, lymphocytes, and macrophages indicate to a pathologist of ordinary skill in the art that the lesion has occurred within the last few days of the monkey's life.
Figure 6:
FIG. 6 is a photomicrograph which shows a mild heart lesion in muscle tissue from the left ventricle of a rhesus monkey, 200× magnification. Note that the lesion area is significantly larger than the minimal heart lesion in FIG. 5. In addition, note the extensive presence of lymphocytes and macrophages in the lesion.

These mutagenic oligonucleotide primers were chosen to span the site at which the mutation(s) was to be introduced and a nearby restriction endonuclease recognition site to facilitate cloning of resulting PCR products carrying mutations of interest. A second oligonucleotide primer was also required in the PCR reaction to allow DNA amplification. This primer also could be designed to contain globin gene mutation(s) or alternatively could consist of wild-type globin gene sequence from a neighboring region of the alpha or beta globin gene. This second primer was also chosen to contain a restriction endonuclease recognition site so that the resulting PCR product could be cloned into appropriately digested pSGE728 for subsequent expression of the mutated alpha or beta globin. Partial restriction maps of the alpha and beta genes from pSGE728 are shown in FIGS. 2 and 3.

The lengths of the mutagenic oligonucleotides were determined by the distance between the site to be mutated and the closest restriction site that could be incorporated into the mutagenic oligonucleotide at a position between the 5-prime end of the oligomer and the site to be mutated. The mutagenic oligomers were typically 30 to 45 nucleotides in length and contained mutations affecting one or two codons although more positions potentially could also be altered if desired. It was generally desirable to place the mutated DNA sequences as far as feasible from the 3-prime end of the oligomer so as to avoid or minimize potential problems during the primer annealing step of the PCR reaction. The mutated nucleotides were generally placed 5–10 nucleotides upstream of the 3-prime end of the mutagenic primer. The globin gene restriction site incorporated near the 5-prime end of the mutagenic oligonucleotide was generally placed 5–12 nucleotides downstream of the 5-prime end to facilitate subsequent digestion of PCR products. Oligonucleotides which were employed solely as primers in PCR (i. e. did not contain mutations) were typically 24–36 nucleotides in length and contained globin gene restriction sites generally located 6–12 nucleotides downstream of the 5-prime end of the oligonucleotide.

PCR reactions were generally performed in an Applied Biosystems GeneAmp 9600. PCR reaction conditions were empirically determined: denaturation was typically at 95° C. for 15–60 seconds, generally annealing temperatures ranged from 45–60° C. for 15–30 seconds with many reactions being run in 50–55° C. range for annealing, and extensions were done at 72° C. for 15–120 seconds.

In some instances the annealing temperature was raised during the course of the reaction: e.g. a reaction might consist of 5 rounds with an annealing temperature of 45° C. followed by 20 rounds at an annealing temperature of 60° C. Typically reactions consisted of a total of 25–30 cycles. The reactions were typically performed in 10 mM Tris-HCl (pH 8.3), 50 mM KCl, 1.5 mM MgCl$_2$ 0.2 mM dNTPs (Pharmacia) and 0.001% gelatin. Oligonucleotide primers were added at concentrations usually 0.5–1.0 μM. Purified plasmid DNA (about 0.1–10 ng per reaction) such as pSGE728 was generally used as template. AmpliTaq® DNA Polymerase (Perkin Elmer) was typically used at 1–10 units per reaction and reaction volumes ranged from 20–100 μl.

Following the PCR reaction the reaction products were purified using the QIAquick PCR Purification Kit (QIAGEN Inc. Santa Clarita, Calif.). The purified products were then subjected to restriction endonuclease digestion with the appropriate enzymes to generate DNA fragments suitable for cloning into similarly cut pSGE728. Restriction digests were performed according to vendor protocols.

The digested PCR fragments could be cloned directly or first subjected to agarose gel electrophoresis and purified out of the agarose gels. Gel composition and electrophoresis conditions were chosen based on the DNA fragment size. Many fragments were about 60–250 base pairs in length and for these fragments resolution in gel electrophoresis is optimal with gels such as 3% NuSeive agarose or 4% Metaphor agarose, both obtained from FMC BioProducts (Rockland, Me.) and used according to vendor protocols. Following electrophoresis, DNA fragments were purified out of agarose gel slices using the QIAEX II Gel Extraction Kit (QIAGEN Inc. Santa Clarita, Calif.) according to the vendor protocols. The vector pSGE728 was also digested with the enzymes appropriate for cloning the mutagenized PCR fragment(s) of interest and similarly gel-purified following more conventional electrophoresis.

Digested and purified mutagenized PCR fragments were ligated with digested and purified pSGE728 vector fragment using T4 DNA ligase (New England BioLabs Beverly, Mass.) according to the vendor protocols and ligation products were used to transform *E coli. E coli* strain JM109 obtained as competent cells from Promega (Madison, Wis.) was often used for this purpose although other strains of *E coli* could also be employed as well as other various methods for preparation of competent cells (Sambrook et al., *Molecular Cloning: A Laboratory Manual* (Cold Springs Harbor, 1989)). Transformants were selected for tetracycline-resistance and could subsequently be sequenced to identify the mutations of interest and confirm the sequence of the mutagenized cloned PCR segment. Plasmid templates were prepared using the QIAprep Spin Miniprep Kit (QIAGEN) and sequenced using the AmpliCycle™ Sequencing Kit (Perkin Elmer, Foster City, Calif.) according to the vendor protocol. Some sequencing was performed manually using Sequenase (United States Biochemical, Cleveland, Ohio) but the preferred method is automated sequencing using the AmpliCycle™ Sequencing Kit (Perkin Elmer, Foster City, Calif.) to perform sequence reactions according to the vendor protocol and analysis on an ABI Prism 377 DNA Sequencer (Applied Biosystems Division of Perkin Elmer, Foster City, Calif.).

Variations of this procedure were sometimes used if a site to be mutated was not located sufficiently close to a restriction site that was unique in pSGE728. In that case a so-called "helper" DNA fragment might be employed to facilitate cloning steps. For example in the alpha gene (FIG. 2) the codon for the V62 position of that protein is somewhat distant from unique restriction sites. Thus, the MaeIII site shown in that figure is not unique to the plasmid but is unique to the segment from the BamHI site to the V62 codon. Therefore, the V62 codon was mutated on a PCR fragment spanning the Mae III through Mlu I segment of the alpha gene and this fragment following MaeIII digestion was ligated to a gel-purified Bam HI-MaeIII fragment of pSGE728. This ligation product was digested with BamHI and MluI (both of which are unique cutters within pSGE728) and the Bam HI-Mlu I fragment was gel purified and ligated to Bam HI-Mlu I- and gel-purified vector fragment of pSGE728. Alternatively V62 mutations could have been incorporated into longer oligonucleotides that spanned unique sites such as MluI.

For construction of large libraries of mutant hemoglobins in which two to four amino acids were simultaneously mutated essentially randomly, similar procedures were followed for mutagenic oligonucleotide design, PCR reactions, and cloning steps. However, it was sometimes desirable to omit restriction sites from certain mutagenic oligomers and instead to incorporate the restriction sites necessary for cloning into pSGE728 via a subsequent PCR amplification with a primer that partially overlapped this particular mutagenic oligomer and spanned a useful restriction site. These amplifications needed to be performed under conditions designed to rigorously exclude environmental contaminants of wild type globin sequences such as pSGE728 and other recombinant plasmids carrying globin sequences. These sorts of environmental contaminants could potentially be preferentially primed in this latter type of amplification because they can anneal to the full length of these oligomer primers whereas the PCR fragments which are the target templates only anneal to a smaller portion of such primers.

In some instances two or more mutagenized PCR segments were ligated together to create segments containing as many as four mutagenized sites prior to cloning into appropriately digested pSGE728 vector. The appropriately sized ligation products were identified and subsequently purified by agarose gel electrophoresis. In some instances the purification step was preceded or followed by PCR amplification using primers that would specifically amplify the ligation product of interest.

To generate a wide spectrum of amino acid substitutions at positions of interest, mutagenic oligomers were synthesized with degeneracies at positions of interest. For "randomization" of a given position two degenerate oligomers were synthesized, one of which contained the sequence N(T/A/C)T at the codon to be randomized while the other contained the sequence (A/T)(T/G)(T/G) at the same position. These two oligomers could be pooled prior to PCR but more usually two independent PCR reactions were used with such pairs and the PCR products roughly quantified (using an AlphaImager™2000 Documentation & Analysis System from Alpha Innotech Corp San Leandro, Calif.) by visualization following gel electrophoresis. Once quantified, roughly equivalent quantities of each fragment could be pooled for subsequent cloning steps. This "randomization" results in 20 different codons generating 16 different amino acid substitutions: there are two codons each for F, I, L, and S; 1 codon for each of D, R, N, A, T, P, C, V, M, H, W, and Y. The amino acids E, K, Q, and G are absent from "randomized" positions in these libraries.

Following ligation into pSGE728 vector and transformation into *E coli*, a number (typically, 24–28) of independent Transformants were picked and the mutagenized PCR segment cloned in each was sequenced. Plasmid templates were prepared using the QIAprep Spin Miniprep Kit (QIAGEN) and sequenced using the AmpliCycle™ Sequencing Kit (Perkin Elmer, Foster City, Calif.) according to the vendor protocol. Sequences were run and analyzed on an ABI Prism 377 DNA Sequencer (Applied Biosystems Division of Perkin Elmer, Foster City, Calif.). Sequences were analyzed to assess the distribution of amino acid substitutions within a given library and the frequencies of PCR-induced and synthetic oligomer-induced errors in DNA sequence. Subsequently clones from libraries were picked and analyzed as described below.

EXAMPLE 2

Construction of α and β Mutants (Di-α and Di-di-α)

Alpha and beta mutations can be combined in derivatives of pSGE728. Typically such combinations can be achieved by cutting mutant derivatives of pSGE728 with appropriate restriction endonucleases that separate the alpha and beta sequences, gel-purifying the restriction fragment containing the beta gene of the mutant beta derivative of pSGE728, gel-purifying the restriction fragment containing the alpha gene of the mutant alpha derivative, ligating these two fragments together, transforming *E coli* and analyzing the resulting transformants to verify the presence of both alpha and beta mutations.

For alpha and beta mutations at residues B10, E11, G8 and E7 such combinations can be made by digesting the mutant derivatives of pSGE728 with BspHI which cuts within the tetracycline-resistance gene and SacII which cuts within the beta gene, about 28 base pairs from the start of the beta coding sequence. Digestion with SacII and BspHI (New England BioLabs, Beverly Mass.) according to the vendor protocols results in two DNA fragments: one 937 bp in length containing a portion of the gene for tetracycline-resistance and nearly all of the beta gene and including the codons for amino acid residues B10, E11, G8 and E7, and the second 2318 bp in length which contains a portion of the gene for tetracycline-resistance and all of the alpha gene. These digestion products can be readily separated by electrophoresis on agarose gels of (0.6–1.0)% using SeaKem® GTG® Gagarose (FMC BioProducts, Rockland, Me.) according to the vendor protocols. Subsequently the 937 bp fragment derived from the beta mutant derivative of pSGE728 can be excised out of the agarose gel and purified using the QIAEX II Gel Extraction Kit (QIAGEN Inc. Santa Clarita, Calif.) according to the vendor protocols.

Similarly the 2318 bp fragment from the pSGE728 derivative carrying the alpha mutation can also be excised from the gel and purified. These two purified fragments can be ligated together using T4 DNA ligase (New England BioLabs Beverly, Mass.) according to the vendor protocols and ligation products were used to transform E coli. E coli strain JM 109 obtained as competent cells from Promega (Madison, Wis.) can be used for this purpose although other strains of E coli could also be employed as well as other various methods for preparation of competent cells (Sambrook et al., supra). Selection for tetracycline resistant transfornants selects for reconstitution of the tetracycline-resistance gene and this is nearly always associated with reconstitution of the beta gene at the SacII site. When individual transformants thus obtained are analyzed by determining DNA sequence for alpha and beta genes and gross plasmid structure, more than 90% are found to be the desired recombinants which have both the alpha and beta mutations. For sequence analysis plasmid templates can be prepared using the QIAprep Spin Miniprep Kit (QIAGEN) and sequenced using the AmpliCycle™ Sequencing Kit (Perkin Elmer, Foster City, Calif.) according to the vendor protocol. Sequences were run and analyzed on an ABI Prism 377 DNA Sequencer (Applied Biosystems Division of Perkin Elmer, foster City, Calif.).

For some purposes it is desirable to produce recombinant hemoglobins carrying amino acid substitutions in both alpha and beta and in which two of the alpha or beta subunits are genetically fused by a linker containing one or more glycine or other amino acid residue, for example as described in U.S. Pat. No. 5,844,089. Preferably, the two alpha subunits are fused to create a "di-alpha" globin. Methods have been described in Looker et al., Nature 356:258–260 (1992) for the construction of such "di-alpha" fusions and these methods could be applied to construct di-alpha versions of any mutant alpha gene. Such di-alpha mutants could readily be combined with any beta mutant of interest as described above.

For some purposes it is desirable to produce recombinant hemoglobins carrying amino acid substitutions in both di-alpha and beta and in which the di-alpha subunits are genetically fused by a peptide linker so that a "di-hemoglobin" or "di-di-alpha" molecule is produced. Methods are described in U.S. Pat. No. 5,844,090, incorporated herein by reference, for the construction of such "di-di-alpha" fusions or other globin fusions to produce di-hemoglobins and these methods could be applied to construct di-di-alpha versions of any mutant alpha gene. Such di-di-alpha mutants could readily be combined with any beta mutant of interest as described above.

EXAMPLE 3

Construction of Recombinant Mutant Hemoglobins SGE3959 SGE3937 and SGE3487

Standard molecular cloning techniques, as described above for the nitric oxide mutant hemoglobins, were used. The following is an outline of the cloning strategy used by the applications to obtain hemoglobins SGE3959 and SGE3937. Alternate cloning strategies could easily be devised by persons of ordinary skill in the molecular genetic arts.

Construction of 3937

Clone S9C into Beta:

In the first step, the Pôrto Alegre mutation (beta Ser9Cys) was cloned using PCR. The PCR template was the 3-gly-di-alpha plasmid from SGE3405. This plasmid contains the Presbyterian (N108K) mutation in the beta gene which was converted to wild-type (N108) in the new Pôrto Alegre construct. A sense PCR primer (JPR34) at the 5' end of the beta gene was designed. This primer included the BspEI cloning site and the new Cys9 codon (note: the SacII cloning site is consequently destroyed). The antisense PCR primer (JPR35) encompassed the SpeI cloning site in the beta gene, encodes for wild-type N108 and converts the Cys93 to Ala. The resultant PCR product was digested with BspEI and SpeI and subcloned into the BspEI/SpeI backbone fragment from SGE3405. The ligation reactions were transformed into JM109, and candidates were miniprepped and sequenced. A correct candidate was transformed into an expression host strain and confirmed by nucleotide sequencing and was designated pSGE1830.

Add S9C to SGE3011:

In the second step, the Pôrto Alegre mutation (beta Ser9Cys) was added to the nitric oxide variant SGE3011 (L29WH58Q 1-gly-di-alpha; V67W beta) by "cut-and-paste" cloning. The backbone fragment was prepared by digesting SGE3011 with restriction enzymes BspEI and NcoI. The insert fragment containing the beta S9C mutation was prepared by digesting pSGE1830 (described above) with BspEI and NcoI. The fragments were ligated together and the resultant plasmid transformed into JM109 and confirmed by nucleotide sequencing of the entire hemoglobin coding region. The final construct was transformed into an expression host strain and confirmed by nucleotide sequencing. The correct candidate was designated strain SGE3744 (pSGE1843).

Add C93A:

The next step involved addition of the beta C93A mutation. This construct was made using "cut-and-paste" cloning. The backbone was the KpnI/EcoRI digested plasmid from SGE3744 (described above). The insert was the ~120 bp KpnI/EcoRI fragment from SGE3731 (the original Porto Alegre clone) which contains the beta C93A sequence. The two fragments were ligated together, transformed into JM109 and the resultant clone verified by restriction digest and sequencing. The correct clone was transformed into an expression host strain, and verified by nucleotide sequencing of the entire hemoglobin coding region. A correct candidate was designated SGE3748 (pSGE1847).

Add Beta T87Q:

The beta T87Q mutation was introduced into the SGE3011 background using PCR. The primers were originally used to introduce T87Q into a rHb1.1 background. The sense primer is CBG124 which is wild-type sequence located at the 5' end of the beta gene. The antisense primer is CBG274, which introduces the T87Q mutation and includes the SacI cloning site. The PCR template was plasmid from SGE3011 (pSGE1410). The PCR product was purified and the ends cleaved with SacII and SacI. A backbone fragment was prepared from pSGE1410 by digestion with SacII and SacI. The SacII/SacI digested PCR product was ligated into the SacII/SacI digested SGE3011 backbone and transformed into JM109. After confirmation by DNA sequence analysis, the correct plasmid was transformed into an expression host strain. The desired variant was verified by nucleotide sequencing and assigned strain number SGE3959 (pSGE3006).

Combine with Beta K82D:

Next it was necessary to add the beta T87Q mutation to a plasmid containing beta K82D. The new variant was constructed by "cut-and-paste" cloning using a BspEI/KpnI backbone from SGE3959 (see above) which includes the SGE3011 NO mutations plus the beta T87Q mutation. The insert fragment was the ~235 bp BspEI/KpnI fragment from SGE3010 which retains the nitric oxide mutation V67W from SGE3011 and adds the Providence K82D mutation to the new variant. The insert fragment was ligated into the backbone fragment. The resultant plasmid was transformed into an expression host strain. The variant was verified by nucleotide sequencing and assigned strain number SGE3965. The resultant hemoglobin is 1-gly-di-alpha -L29WH58Q, beta-V67WK82DT87Q (pSGE3012).

Combine V67WK82DT87Q with S9CC93A:

The next step involved addition of the beta S9C and C93A mutations. This new construct was made by "cut-and-paste" cloning using the BglII/SacI beta fragment from SGE3965 (described above). This fragment was subcloned into a BglII/SacI backbone from SGE3748 (described above). The desired hemoglobin is 1-gly-di-alpha-L29WH58Q; beta-S9CV67WK82DT87QC93A. The ligation reaction was transformed into JM109. Candidates were confirmed by DNA sequence analysis and a correct candidate was transformed into the an expression host strain and was verified by nucleotide sequencing of the entire hemoglobin coding region. The strain was designated SGE3973 (pSGE3019).

Add D73K:

The beta D73K mutation was first cloned in combination with K82D into the plasmid in SGE3011 by PCR. The plasmid of SGE3011 which contains beta V67W was used as a template in the PCR with CBG316 (D73KK82D) and CBG124. The product was cleaned and digested with BspEI and KpnI. The plasmid from SGE3011, which contains dialpha L29WH58Q, beta V67W was digested as above, cleaned, SAP treated, and the large fragment gel purified. This fragment and the PCR product were ligated and the ligation reactions transformed into an expression host strain to produce candidates of the strain designated SGE3925 (pSGE2044).

The plasmid from SGE3973 (above) which contains all of the desired beta mutations except for D73K was digested with BglII and KpnI, cleaned, SAP treated, and the large fragment gel purified. The plasmid from SGE3925 (above), which contains alpha L29WH58Q, beta V67WD73KK82D was digested as above and the small fragment gel purified. These fragments were ligated and the ligation reactions transformed into an expression host strain. Transformants were grown, miniprepped, and the globin coding region was sequenced. A correct transformant was designated SGE3933 and the plasmid was designated pSGE3052.

Transfer to Manufacturing Strain:

pSGE3052 was miniprepared and transformed into an expression host strain of E.coli with one extra chromosomal copy of the hemH gene. Transformants were grown, miniprepared, and the globin coding region was sequenced. A correct transformant was designated SGE3937.

Construction of 3959

Add Beta T87Q:

The beta T87Q mutation was introduced into the SGE3011 background using PCR. The primers were originally used to introduce T87Q into a rHb1.1 background. The sense primer is CBG124 which is wild-type sequence located at the 5' end of the beta gene. The antisense primer is CBG274, which introduces the T87Q mutation and includes the SacI cloning site. The PCR template was plasmid from SGE3011 (pSGE1410). The PCR product was purified and the ends cleaved with SacII and SacI. A backbone fragment was prepared from pSGE1410 by digestion with SacII and SacI. The SacII/SacI digested PCR product was ligated into the SacII/SacI digested SGE3011 backbone and transformed into JM109. After confirmation by DNA sequence analysis, the correct plasmid was transformed into an expression host strain of E.coli with two extra chromosomal copies of the hemH gene and a chromosomal gene conferring spectinomycin resistance. Transformants were grown, miniprepared, and the globin coding region was sequenced. A correct transformant was designated SGE3959 (pSGE3006).

Construction of 3487

SGE3487 is expressed from the same plasmid as SGE3959 (pSGE3006) and results in the expression of hemoglobin with the same protein sequence. Thus, it is constructed in accordance with the protocol set forth for SGE3959. However, SGE3487 is expressed in a different bacterial host strain than SGE3959. SGE3487 is expressed in an E.coli strain that has only one extra chromosomal copy of the hemH gene and does not have a chromosomal gene conferring spectinomycin resistance. The different antibiotic resistance provides a means to select for either SGE3487 or SGE3959.

EXAMPLE 4

Production of Reduced Side Effect Hemoglobin Candidates

To produce large numbers of hemoglobin variants E coli strains containing recombinant plasmids which encode variant hemoglobins, such as derivatives of pSGE728, were typically grown in shake flasks usually at volumes of about 50 ml. Generally defined media supplemented with about 0.2% yeast extract were used for cell growth and tetracycline was added, generally at 15 μg/ml to select for maintenance of the recombinant plasmid. Expression of the hemoglobin genes was induced by addition of IPTG, usually at a concentration of 100 μM and hemin was added to a final concentration of 50 μg/ml generally at the time of induction. Cells were generally grown and induced at 28° C. Cells grown to stationary phase, such as typical saturated overnight cultures, could be directly inoculated (generally at a dilution ranging from 1/50 to 1/1000) into media containing IPTG and hemin or such cultures could be inoculated into media lacking IPTG and hemin, grown to log phase, e.g. 0.4–0.7 OD @ $A_{600}$ and then induced by the addition of IPTG with hemin typically being added to the cultures at the time of induction. Cultures were generally grown under inducing conditions overnight (~14–20 hours) although shorter times, e.g. about 6 hours could also be employed. At the end of this time, cells were pelleted by centrifugation and the cells pelleted were either frozen and stored at −80° C. or processed immediately.

Recombinant hemoglobins were purified by small-scale column chromatography using Fast Flow Zn-Chelating Sepharose (Pharmacia). During the purification, cells, lysates, all buffers and eluted hemoglobins were kept cold on ice as much as possible. Typically, a pellet of a 50 ml culture was resuspended with 1.0 ml ice-cold 25 mM sodium tetraborate and transferred to a 1.7 ml eppendorf tube. Cells were usually lysed by sonication, although enzymatic lysis by lysozyme could also be employed. Sonicated lysates were clarified by centrifugation (generally about 14,000×g for 15–20 minutes at 4° C.) following addition of 20 μl of 20 mM ZnAcetate. Supernatants were loaded onto a ~150–200 μl column that had previously been equilibrated as follows:

- 2–10 column volumes 0.5 M NaOH
- 6–10 column volumes 0.5 M NaCl, 20 mM Tris-HCl pH 8.1 @ 0° C.
- 3–10 column volumes 20 mM ZnAcetate
- 6–10 column volumes 0.5 M NaCl, 20 mM Tris-HCl pH 8.1 @ 0° C.

Following the loading, the column was washed with at least 9 column volumes 0.5 M NaCl, 20 mM Tris-HCl pH 8.1 at 0° C. followed by at least 3 column volumes 0.05 M NaCl, 20 mM Tris-HCl pH 8.1 at 0° C. and then eluted with ~1.0 ml of the desired buffer (e.g. 0.1 M Na phosphate pH 7.0) containing 30 mM EDTA. Hemoglobin was typically recovered in a volume of ~200–400 μl. These samples may be used in various tests. If not used immediately, samples were frozen and stored −80° C. Larger quantities can be prepared using the techniques taught in [produce Milne/Plomer patent cite], incorporated herein by reference.

EXAMPLE 5

Purification of Reduced Side Effect Hemoglobin

All molecules, monomeric and dimeric, were first captured by immobilized metal affinity chromatography (IMAC) and further processed as described in U.S. Pat. No. 5,840,851, incorporated herein by reference. The hemoglobin solution was then diafiltered into the appropriate load buffer for further purification. For monomeric hemoglobins, the appropriate load buffer was 20 mM Tris (pH 9.0) for loading onto an anion exchange column (Q Sepharose FF, Pharmacia, Uppsala, Sweden). The protein which was loaded onto the column at 15 gm/L is washed with three column volumes of 12.5 mM Tris (pH 7.8). The protein was then eluted in two to three volumes of 12.3 mM Tris (pH7.6) or if the pI of the protein is below 7.5 it was eluted in a Bis-Tris buffer at the appropriate pH. pI was used to determine proper wash and elution conditions for each protein, both monomeric and dimeric. Certain mutations on the surface of some of the heme pocket mutants were found to effect this value. For dimeric hemoglobins, the appropriate load buffer was 10 mM KPi (pH 7.0) for loading onto a ceramic hydroxyapatite (CHT) column (BioRad) or 20 mM Tris (pH 8.0) for loading onto a hydrophobic interaction chromatography (HIC) column (BioRad). The protein was loaded onto the CHT column at 20 gm/L, and the column was then washed with eight column volumes of 30–40 mM KPi (7.0). Five column volumes of 85–90 mM Kpi (pH7.0) were used to elute the protein from the column. When the HIC column was used, protein was loaded at 15 gm/L and the column was then washed with five column volumes of 1.2M Ammonium Sulfate/20 mM Tris (pH 8.0). The protein was eluted using 3 column volumes of 1M Ammonium Sulfate/20 mM Tris (pH 8.0). The wash steps for both CHT and HIC columns were developed to allow the monomeric hemoglobin to be eluted while leaving the di-hemoglobins and larger molecules bound to the column. Pools from either column were diafiltered to prepare for loading onto an anion exchange column. The anion exchange step was designed to wash away remaining monomeric hemoglobin from the di-hemoglobin, yielding a di-hemoglobin pool that was 98% pure on a size basis. The anion exchange column is a Super Q 650M (TosoHass). The column is equilibrated with 20 mM Tris (pH9.0) and 15 gm/L of protein was loaded on the column. The column was then washed with three column volumes of 10–15 mM Tris (pH 7.6–7.8) and the protein was eluted in three column volumes of 15–30 mM Tris (pH 7.6–7.8). Or, if pH was between 7.3–7.6 then a Bis-Tris buffer was used. The protein from this point on was handled as described in U.S. Pat. No. 5,840,851. After purification, protein was either polymerized, or diafiltered into formulation buffer for use.

EXAMPLE 6

Preparation of Glutaraldehyde Cross-linked Reduced Side Effect Hemoglobin

The following conditions were utilized to polymerize deoxyhemoglobin SGE3011.

Materials:
2% glutaraldehyde in water, degassed (Made from Sigma Grade I, 25% glutaraldehyde stock). 0.92 M NaBH$_4$ in 0.05 N NaOH, degassed.
Deoxy SGE3011: approx. 300g. at 50±5 g/L in CHT Load Buffer (10 mM KPhos, pH 7.0)

Equipment:
The reaction is performed in the 2nd Ultrafiltration (UF-2) system equipment, comprising an approx. 20 L tank, with recirculation loop, pump, and diafiltration membrane attached:

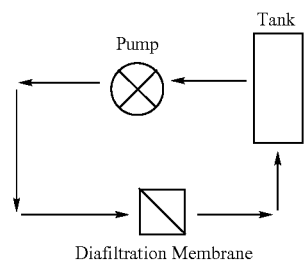

Method:
Glutaraldehyde additions are administered using syringes mounted on a syringe pump, at a site immediately upstream of the recirculation pump inlet. A polymerization reaction starts by performing 3 equivolume additions of 2% glutaraldehyde, 15 or 20 min. apart, to achieve a final 13.5:1 molar excess of glutaraldehyde over hemoglobin at the end of the injection set. Each injection is administered over a 2.5 min. time span.

Mixing is accomplished by regulating the recirculation pump rate. At time zero, the pump is set to 40 Hz. The 40 Hz rate is maintained during the injection series, and for 10 min. thereafter. The rate is then slowed to 20 Hz until monitoring (see below) indicates the reaction is ready to be quenched.

The reaction temperature at time zero is 6–7° C. The temperature increases to 15–17° C. during the phase in which the recirculation pump is mixing the reaction at 40 Hz. The temperature is then maintained at 15–17° C. when the pump is set to 20 Hz.

Monitoring of the reaction involves near-real-time analysis of polymer molecular weight distribution using a fast, high pressure size exclusion chromatography method. At time zero, and every 10 min. thereafter, a 0.25 mL sample is obtained from the reactor, and diluted 40-fold in cold modified Ringer Salts solution (96 mM NaCl, 4 mM KCl). 25 uL of the diluted sample is then run on a Toso-Haas TSK QC-PAK GPC300 SEC-HPLC column. The column buffer is 50 mM NaPhos, 300 mM NaCl, pH 6.6. The column is run at 1.0 mL/min, at 30° C., for 7.5 min.

When the chromatographic monitoring indicates a desired size distribution, the reaction is quenched by bolus injection of $NaBH_4$ (via syringes on the syringe pump) to attain a final 4-fold molar excess of borohydride over total injected glutaraldehyde. The recirculation pump rate is increased to 40 Hz for the injection and for 10 min thereafter, and then decreased back to 10 Hz.

After quenching, the solution is diafiltered through Millipore 10K PES membranes v. 10 TOV of deoxygenated CHT Load Buffer to remove excess borohydride and low molecular weight adducts. The solution is then diafiltered briefly vs. oxygenated CHT Load Buffer to effect rapid hemoglobin oxygenation.

For purification of desired polymers the polymeric mixture is then loaded onto a 14 L BPG300 column (20 cm bed) of BioRad 80 micron particle size Type I ceramic hydroxyapatite (CHT), previously equilibrated in oxygen-saturated CHT Load Buffer. Chromatography then proceeds at 200 cm/hr linear flow rate, at 8° C., under low bioburden conditions, using oxygen-saturated buffers. After loading, the column is washing with 1 column volume (CV) of Load Buffer (10 mM KPhos, pH 7.0) to remove very high MW polymers. The column is subsequently washed with 10 CVs of Wash Buffer (75 mM KPhos, pH 7.0) to remove monomeric hemoglobin. (Some dimeric and higher MW oligomers are also removed at this step). The column is then eluted with 3CVs of 200 mM KPhos, pH 7.8 to release desired polymers. (The pH of the CHT Elution Buffer has varied from 7.0 to 7.8, depending on the pH requirements for the final formulation). The pool of desired polymers is then diafiltered into formulation buffer to remove elution salts and prepare the product for use.

EXAMPLE 7

Preparation of Bismaleimide Tripolvethyleneglvcol Cross-linked Reduced Side Effect Hemoglobin The following conditions were used to polymerize SGE3937.

Materials:

Oxyhemoglobin SGE3937: approx. 400 g. at 40±5 g/L (based on a spectrophotometric determination of hemoglobin concentration) in 15 mM Tris, 150 mM NaCl buffer, pH 7.7.

$BM[PEG]_3$ stock solution: A 0.5 g/L solution was prepared in a Class 100 hood by mixing an appropriate mass of bismaleimide tripolyethyleneglycol ($BM[PEG]_3$) with an appropriate volume of WFI to make a slight excess of reagent (at the desired concentration) over that needed, based on calculation of a 0.9:1 molar ratio of polymerizing reagent-to-hemoglobin. The solution was then filtered through a 0.2 micron membrane.

N-ethyl maleimide: A half-liter solution of 40 mM N-ethyl maleimide (NEM) was prepared by adding 2.5 g NEM powder to 497.5 g WFI. The solution was filtered through a 0.2 micron membrane.

Equipment:

The reaction was performed in a 70 L stainless steel reactor, containing a variable speed mixing agitator, a glycoljacket for temperature regulation, and ports for sample withdrawal, reagent addition, as well as atmospheric control.

Method:

The reactor was maintained at the ambient temperature of the cold room (6–10° C.) throughout the process. An appropriate volume of oxygenated SGE3937 at the targeted initial concentration (40±5 g/L) was transferred from Ultrafiltration system 2 (UF-2) into the reactor under atmospheric conditions. Once hemoglobin volume and concentration parameters within the reactor were verified, the agitator was set such that mixing occurs with a minimum of foam/bubble generation. Meanwhile, the $BM[PEG]_3$ solution was prepared and the volume needed for polymerization to a 0.8:1 molar ratio was transferred to a small pressure can. The pressure can was attached to the reactor via tubing running through a peristaltic pump. The reaction was subsequently initiated by pumping the $BM[PEG]_3$ solution from the pressure can into the reactor, at a speed such that the solution was transferred in a 30 min span.

The reaction was monitored using a ToSoHaas TSK-G3000SWx1 HPLC size exclusion chromatography (SEC) column. At time zero and at 15 min after the initial addition was completed, a 0.25 mL sample was obtained from the reactor and diluted to a 1 g/L concentration. 20 uL of the diluted sample was then run on the column, on a Hewlett-Packard HP1090M chromatography workstation. The column buffer was 50 mM NaPhos, 300 mM NaCl, pH 6.6. The column was run at 0.5 mL/min, at 30° C., for 25 min.

While the initial reaction proceeded, a second aliquot of polymerizing reagent was added to the additions pressure can. The volume added was such to give an additional 0.1× molar equivalent of $BM[PEG]_3$ to the reaction (and a final 0.9:1 molar ratio of polymerizer-to-hemoglobin). After completion of the initial reaction, the volume within the reactor was adjusted (using 15 mM Tris, 150 mM NaCl, pH 7.7) so as to obtain a hemoglobin concentration between 10–15 g/L. The second $BM[PEG]_3$ addition was then initiated, using an addition rate identical to that for the first addition. After an additional 10 min reaction time, another sarnple was withdrawn, diluted and SEC analyzed as described above.

While the second addition and reaction proceeded, the additions pressure can was rinsed well with WFI. An appropriate volume of 40 mM NEM, to obtain a 1.5× molar excess over hemoglobin, was transferred to the pressure can. Upon confirmation of a desired polymer molecular weight distribution, the reaction was quenched by bolus addition of NEM to the reactor. The polymer distribution of the quenched reaction mixture was monitored by SEC as described above.

After quenching, the solution was transferred back into UF-2 under oxy conditions. The polymer solution was ultrafiltered through Millipore 100K regenerated cellulose membranes vs oxygenated formulation buffer to remove excess $BM[PEG]_3$ and NEM. The product was sterile filtered through a 0.2μ filter to prepare the product for final filling.

EXAMPLE 8

Evaluation of Hemoglobin Aggregate Precipitate Formation in Hemoglobin Compositions Stored for Prolonged Periods Hemoglobin compositions containing rHB1.1, SGE3011, or SGE3959 were tested for the formation of hemoglobin aggregates and precipitate over a period of three months. As methemoglobin has been implicated in aggregate formation, 10 g/dl solutions of the three hemoglobins in formulation buffer were standardized to 10% methemoglobin content. The hemoglobin solutions were stored at a constant temperature of 25° C. for three months. 25 mL samples of each hemoglobin solution were taken at 2, 4, 6, 8, and 12 weeks. Each sample was ultracentrifuged at 112,000 g for one hour. The pellet was washed and re-centrifuged for 10 minutes. The pelleted protein precipitate was resolubilized in 0.1% SDS, and the protein absorbance read at 292 mn and protein concentration quantified by comparison to a protein standard curve. The results of the experiment are shown in FIG. 11, as milligrams of precipitate (PPT) per gram of total hemoglobin in the sample (THb). As can be seen in the figure, SGE3959, which contains the β T87Q mutation, produced markedly less precipitate over the three month storage period than the otherwise identical SGE3011 or than rHb1.1.

EXAMPLE 9

Measurement of Reaction Between Oxyhemoglobin and Nitric Oxide

Nitric oxide gas was passed through a column of NaOH pellets and used to thoroughly flush a tonometer. Anaerobic buffer (0.1 M sodium phosphate, pH 7.4) was injected into the tonometer and equilibrated with the nitric oxide to make a stock solution. Dilutions of the stock solution were made in glass syringes containing anaerobic buffer. Time courses of the reaction of oxyhemoglobin with nitric oxide were collected at 420 and 402 nm using an Applied Photophysics stopped-flow device. Temperature was 20° C. Data were collected and analyzed using the software program !SX.17MV supplied by Applied Photophysics.

Table 1 provides nitric oxide reactivity data for various mutant hemoglobins used in the biological experiments described in this application. Additional data for other mutant hemoglobins may be found in WO/98/50430, hereby incorporated by reference in its entirety.

EXAMPLE 10

Evaluation of Heart Lesion Formation after the Administration of Hemoglobin Compositions to Rhesus Monkeys Extracellular hemoglobin formulations (see Table 2 below), prepared as sterile protein solutions, were stored refrigerated at 2–8° C., or frozen, until approximately 30 minutes prior to dosing.

At least five rhesus monkeys (*Macaca mulatta*), preferably of mixed sexes, were used for each hemoglobin composition tested in this study. Animals selected for use in this study were as uniform in age and weight as possible. They were generally approximately 2 to 6 years of age, and their initial body weights ranged from approximately 3 to 6 kg.

For each test conducted, a minimum of 6 animals, from which at least 5 animals were selected for the study, underwent a comprehensive health screen prior to assignment to the study. The animals were lightly sedated with ketamine HCl (to effect) and given a complete physical examination by a staff veterinarian, including abdominal palpation and observations of the condition of integument, respiratory, and cardiovascular systems. The prestudy determination of health status also included evaluation of a standard panel of serum chemistry, hematology and coagulation parameters, as well as an examination of fecal samples for ova and parasites.

For each test conducted, at least five animals were assigned to the study after physical examinations were completed. On Day 1, each animal received a single intravenous infusion of test hemoglobin solution at a rate of 1 mL/kg/minute. The animals were evaluated for changes in clinical signs and clinical pathology indices. All animals were euthanized approximately forty-eight hours postdose. A full necropsy was conducted on all animals, and tissues were collected, preserved, processed and examined.

All animals received a dose of 20 mL/kg of a test hemoglobin solution. Doses were administered into a peripheral vein via intravenous infusion. The animals were temporarily restrained in primate chairs, and a dosing catheter was inserted in a cephalic or saphenous vein of each animal and connected to the dosing syringe. The contents of the syringe were expelled at a controlled rate using a Harvard infusion pump, or its equivalent. The rate of infusion was 1 ml/kg/min (total duration of approximately 20 minutes). The absolute dose volume for each animal was based on the most recent body weight measurement taken up to the day prior to dosing. After dose delivery, the catheter was removed, and each animal was returned to its cage.

Blood samples for evaluation of serum chemistry and/or hematology were collected from all animals prior to the start of infusion, at the end of infusion, and 1, 2, 4, 8, 24, and 48 hours from the start of infusion. Blood samples for evaluation of coagulation parameters were collected on the day of necropsy (immediately prior to euthanasia).

The animals were fasted overnight prior to dosing and blood collection through the 4-hour post-initiation of infusion timepoint; they were fed all of their daily rations following the 4-hour blood collection; and they were fasted again overnight prior to blood collection for both the 24- and 48-hour blood collections.

The animals were terminated by exsanguination while under deep anesthesia induced with ketamine and Bauthanasia-D or equivalent. Food rations were withheld overnight prior to the day of sacrifice, and small amounts of fruit were generally provided during this period. A terminal body weight was obtained at necropsy for all sacrifices. This body weight was used to calculate organ/body weight ratios. A complete gross necropsy was conducted by qualified personnel on all animals sacrificed during the study. The necropsy include examination of carcass and muscular/skeletal system, all external surfaces and orifices, cranial cavity and external surface of the brain, neck with associated organs and tissues, and thoracic, abdominal and pelvic cavities with their associated organs and tissues.

Heart tissues from each animal sacrificed were collected and preserved in neutral-buffered 10% formalin.

For all animals necropsied, tissues were embedded in paraffin, sectioned, stained on hematoxylin and eosin, and examined by light microscopy. Slides were prepared and examined. The results of the histopathology examination, using the criteria explained below, are set forth in Table 2.

To quantify the characteristics of the cardiac lesions using anatomic pathology, two parameters in particular, incidence and severity, were utilized. Incidence was the number of hearts which exhibited any evidence of lesion formation divided by the number of hearts examined (e.g., 2/4). Severity was a measure of lesion intensity and extent, which was graded by the evaluating pathologist on an ascending scale of 0–4. Lesions of Grade 1 are considered minimal, Grade 2 are considered mild, Grade 3 are moderate, and Grade 4 lesions are severe. In a given group of tissue specimens, an overall average severity score was sometimes also calculated by summing the severity grades for each affected heart and dividing by the total number of hearts evaluated in that group.

calculated based upon body weight of the respective animal and administered at a rate of approximately 1 ml/kg/min using an infusion pump. The total amount administered to each animal in the study is set forth in Table 3. The absolute dose volume for each animal was based on the most recent body weight measurement taken up to the day prior to dosing.

Blood samples for evaluation of serum chemistry and/or hematology were collected from all animals prior to the start of infusion, at the end of infusion, and immediately prior to necropsy on Day 2 or Day 14. Blood samples for evaluation of coagulation parameters were collected on the day of necropsy (immediately prior to euthanasia).

TABLE 2

| Molecule | Incidence | Severity Score | Overall Severity | $k'_{NO,OX}$ | di-alpha mutations | beta mutations |
|---|---|---|---|---|---|---|
| HSA | 0/3 | 0.0 | 0.0 | NA | | |
| DCLHb | 3/3 | 2.0 | 2.0 | 70 | | |
| SGE3011[A] | 5/5 | 1.0 | 1.0 | 2.5 | B10Trp, E7Gln | E11Trp |
| SGE3011[B] (glutaraldehyde-decorated) | 1/3 | 1.0 | 0.3 | 2.5 | B10Trp, E7Gln | E11Trp |
| SGE2971[A] (genetically fused dimer) | 2/5 | 1.5 | 0.6 | 2.5 | B10Trp E7Gln | E11Trp, EF6Asp |
| SGE3011[B] (glutaraldehyde-polymerized) | 0/5 | 0.0 | 0.0 | 2.5 | B10Trp, E7Gln | E11Trp |
| SGE3653[C] (glutaraldehyde-polymerized) | 4/5 | 1.8 | 1.4 | 15.2 | B10Phe, E7Gln | E11Trp |
| SGE3959[C] (BMA-PEG polymerized) | 3/5 | 1.7 | 1.0 | 2.5 | B10Trp, E7Gln | E11Trp, F3Gln |
| SGE3937[C] (BM-PEG polymerized oxyhemoglobin) | 0/5 | 0.0 | 0.0 | 2.5 | B10Trp, E7Gln | A6Cys, E11Trp, E17Lys, EF6Asp, F3Gln, F9Ala |

[A]150 mM NaCl, 5 mM NaPi, 3 µM EDTA as excipient, pH 7.5 at 8° C.
[B]50 mM NaCl, 5 mM NaPi, 3 µM EDTA, 0.075% Tween as excipient, pH 7.5 at 8° C.
[C]96 mM NaCl, 4 mM KCl, 24 mM Na D-Gluconate, 3 µM EDTA as excipient The hemoglobin compositions tested that were reduced lesion hemoglobins were SGE3011 and SGE3011 (glutaraldehyde-decorated). Lesion-free hemoglobin compositions tested were SGE3011 (glutaraldehyde-polymerized) and SGE3937 (BM-PEG polymerized oxyhemoglobin).

Evaluation of Heart Lesion Formation after Administration of Hemoglobin Compositions to Rhesus Monkeys, Rats, and Pigs Extracellular SGE3487 or DCLHb® hemoglobin formulations, prepared as sterile protein solutions, were stored refrigerated at 2–8° C., or frozen, until approximately 30 minutes prior to dosing. Human Serum Albumin (HSA) was employed as a control in the study and was handled in accordance with the parameters set forth for SGE3487.

In this animal model, Rhesus monkeys, rats and pigs were employed as test subjects. The animals selected for use were preferably of mixed sexes and were as uniform in age and weight as possible. The number and type of animal utilized in the study is indicated in Table 3.

The animals underwent a comprehensive health screen prior to assignment to the study. The animals were lightly sedated with ketamine HCl (to effect) and given a complete physical examination by a staff veterinarian, including abdominal palpation and observations of the condition of integument, respiratory, and cardiovascular systems. The pre-study determination of health status also included evaluation of a standard panel of serum chemistry, hematology and coagulation parameters, as well as an examination of fecal samples for ova and parasites.

Each animal received a single intravenous infusion of the indicated hemoglobin composition or HSA (as indicated in Table 3) on the first day of the study. Infusion volumes were The animals were terminated by exsanguination while under deep anesthesia induced with ketamine and Bauthanasia-D or equivalent on either Day 2 (48 hours) or Day 14 of the study. Food rations were withheld overnight prior to the day of sacrifice, and small amounts of fruit were generally provided during this period. A terminal body weight was obtained at necropsy for all sacrifices. This body weight was used to calculate organ/body weight ratios. A complete gross necropsy was conducted by qualified personnel on all animals sacrificed during the study. The necropsy include examination of carcass and muscular/skeletal system, all external surfaces and orifices, cranial cavity and external surface of the brain, neck with associated organs and tissues, and thoracic, abdominal and pelvic cavities with their associated organs and tissues.

Heart tissues from each animal sacrificed were collected and preserved in neutral-buffered 10% formalin.

To quantify the characteristics of the cardiac lesions using anatomic pathology, two parameters in particular, incidence and severity, were utilized. Incidence was the number of hearts which exhibited any evidence of lesion formation divided by the number of hearts examined (e.g., 2/4). Severity was a measure of lesion intensity and extent, which was graded by the evaluating pathologist on an ascending scale of 0–4. Lesions of Grade 1 are considered minimal, Grade 2 are considered mild, Grade 3 are moderate, and Grade 4 lesions are severe. In a given group of tissue specimens, an overall average severity score was sometimes also calculated by summing the severity grades for each affected heart and dividing by the total number of hearts evaluated in that group. The results of the study are set forth in Table 3.

TABLE 3

| Animal | Dose of SGE3487[A] (g/kg) | Sacrifice timepoint post-dosing | Number of Animals | Lesion Incidence | Severity |
|---|---|---|---|---|---|
| Rhesus Monkeys | 0.5 | 48 h | 8 | 0 | 0 |
| | 1.0 | 48 h | 8 | 0 | 0 |
| | 2.0 | 48 h | 8 | 0 | 0 |
| Rhesus Monkeys | 0.5 | 14 d | 4 | 0 | 0 |
| | 1.0 | 14 d | 4 | 0 | 0 |
| | 2.0 | 14 d | 4 | 0 | 0 |
| Rats | 1.0 | 48 h | 10 | 1 | 2 |
| | 2.0 | 48 h | 10 | 0 | 0 |
| | 4.0 | 48 h | 10 | 3 | (1, 2, 1) |
| Rats | 1.0 | 14 d | 10 | 0 | 0 |
| | 2.0 | 14 d | 10 | 0 | 0 |
| | 4.0 | 14 d | 10 | 0 | 0 |
| Pigs | HSA 2.0 | 48 h | 4 | 0 | 0 |
| | DCLHb 2.0 | 48 h | 4 | 4 | (2, 2, 2, 2) |
| | SGE3487 1.0 | 48 h | 5 | 0 | 0 |
| | SGE3487 2.0 | 48 h | 5 | 0 | 0 |

[A]96 mM NaCl, 4 mM KCl, 24 mM Na D-Gluconate, 3 μM EDTA as excipient

These results demonstrate that administration of SGE3487 at all doses tested was able to completely attenuate the development of heart lesions in rhesus monkeys and pigs. The data apparently indicating development of lesions in rats is highly suspect and could be the result of a number of putative factors. However, SGE3487's ability to prevent lesion development in the rhesus monkey, a sensitive primate model that closely emulates administration to humans, provides compelling evidence of its ability to prevent or reduce the occurrence of heart lesions in humans.

EXAMPLE 11

Evaluation of the Gastrointestinal Dysmotility Effect of Hemoglobin Compositions in Rats Several hemoglobins, both monomeric and polymeric, were tested for their effect on gastric emptying, as compared to an injection of a similar amount of human serum albumin.

Male Sprague-Dawley rats (Charles River, Raleigh, N.C.) weighing 250–350 g were deprived of food for at least 17 h before experimentation with water available ad libitum. The animals were group housed in cages with wire-mesh bottoms to attenuate coprophagy. Water was removed just prior to experimentation. All rats were studied under conscious, resting conditions.

The nutrient meal was composed of methylcellulose dispersed in ice water to which was added casein, cornstarch, powdered confectioner's sugar, and beef bouillon (Droppleman et al., 1980). Methylcellulose, and casein were purchased from Sigma (St. Louis, Mo.). The mixture was thoroughly blended after the addition of each ingredient to insure proper dispersion and homogeneity. The meal was divided into aliquots and then refrigerated for at least 24 h prior to use to allow trapped air to escape. Aliquots were frozen until needed. The day prior to experimentation, meal aliquots were allowed to thaw in a refrigerator overnight. Just prior to use, the meal was warmed to approximately 28° C. and thoroughly mixed. Each animal received 3 g (approximately 3 ml) of the meal via an intragastric tube.

Each rat was given an IV injection of a test or control article by the tail vein and returned to a cage. Treatment groups included the proteins human serum albumin (10% HSA, control solution), and twelve different recombinant hemoglobin solutions, which were intravenously administered at doses of 1500 mg/kg. Each treatment group consisted of 10–12 rats. Forty-five minutes after test article administration, each rat was orally gavaged with 3 g of a nutrient meal and again returned to a cage. Forty-five minutes after feeding, rats were euthanized by $CO_2$ asphyxiation, and laparotomized to expose the stomach. Upon exposure, the pylorus and cardia were quickly ligated to intragastrically isolate the residual meal. The stomach was removed, weighed, cleared of contents, and the weight (Wt.) was determined again.

Percent emptying of the stomach was expressed as:

% emptied=[(Wt. meal given−(Wt. full stomach−Wt. empty stomach))/Wt. meal given]×100.

The results are shown in the table below.

TABLE 4

GASTRIC EMPTYING ASSAY
(Dose: 1,500 mg/kg)

| Molecule | % Gastric Emptying |
|---|---|
| rHb 1.1 | 29.6 ± 9 |
| rHb 1.1 (Glutaraldehyde decorated) | 33.6 ± 12 |
| DCLHb | 44.2 ± 6 |
| SGE2821 | 46.9 ± 6 |
| SGE3653 | 59.2 ± 8 |
| SGE3011 | 58.3 ± 7 |
| SGE2822 (Genetically fused dimer) | 63.1 ± 8 |
| SGE2971 (Genetically fused dimer) | 64.3 ± 12 |
| rHb1.1 (Glutaraldehyde polymerized) | 68.5 ± 7 |
| SGE3011 (Glutaraldehyde polymerized) | 86.6 ± 6 |
| SGE3959 (BMA-PEG polymerized) | 93.3 ± 6 |
| SGE3937 (BM-PEG polymerized) | 96.8 ± 3 |
| HSA | 100.0 ± — |

As can be seen from the results above, decreased nitric oxide kinetics and polymerization individually improve the gastrointestinal effects of hemoglobin compositions. However, the hemoglobins in the test group which exhibited a reduced or low gastrointestinal effect, as measured in the gastric emptying model, had both low nitric oxide reactivity and were polymerized, such as hemoglobins SGE3011 (glutaraldehyde polymerized), SGE3959 (BMA-PEG polymerized), and SGE3937 (BM-PEG polymerized).

EXAMPLE 12

Evaluation of the Pressor Effect of Hemoglobin Compositions in Rats

Male Sprague-Dawley rats (Charles River, 250–350 g) were used for all experiments. The animals were chronically instrumented with pulsed Doppler flow probes for cardiac output measurement and with indwelling arterial and venous catheters for blood pressure measurement and hemoglobin infusion. The animals were anesthetized (50 mg/kg i.p. pentobarbital sodium), intubated, and artificially ventilated (Columbus Instruments, Columbus, Ohio). Using aseptic techniques, a sternotomy was performed to enable placement of a pulsed Doppler flow probe (Crystal Biotech) on the ascending aorta. An appropriately sized probe was chosen to ensure a secure, non-constrictive fit, and it was tied in place with nylon suture. The flow probe leads were passed through the chest wall, routed subcutaneously to the scapular region, and stored in a pocket under the skin. After the chest was closed and evacuated, the rat was removed from the ventilator, and systemic and topical antibiotics were administered. After a recovery period of at least 5 days, polyethylene catheters (PE 10) were placed in the descending aorta and vena cava via the femoral artery and vein, respectively, under halothane anesthesia. The catheters were routed subcutaneously to the back of the head and stored with the Doppler flow probe leads in a protective plastic container sutured to the skin. Systemic and topical antibiotics were again administered, and an additional 2 days were allowed for recovery.

For all experiments, the animals were studied in a conscious, resting state. On the day of the experiment, each rat was placed in a Plexiglas experimental chamber that was of sufficient size (25×15×12.5 cm) to allow free movement. The chamber was flushed continuously with fresh air, and fresh bedding covered the chamber floor. The catheters and Doppler flow probe leads were fed through the top of the chamber, and both catheters were opened and flushed with sterile, heparinized saline. The arterial catheter was connected to a pressure transducer for arterial pressure measurement, and the venous catheter was connected to a syringe containing hemoglobin or human serum albumin (HSA, Baxter Healthcare Corp.). HSA was used as a negative control with the assumption that it does not consume nitric oxide or directly cause vasoconstriction. The flow probe leads were connected to a modified high-velocity module (HVPD, Crystal Biotech, Northborough, Mass.) that was used in the autotracking mode at a pulse repetition frequency of 125 kHz to avoid detection of spurious, aliasing signals. Arterial pressure, heart rate, and cardiac output were continuously recorded at a sampling frequency of 50 Hz using a Windaq data acquisition system (Dataq Instruments, Columbus, Ohio) and a 160 MHZ Pentium computer (Compaq).

After sufficient time for acclimatization to the experimental surroundings and recording of baseline data (generally 30–60 min), hemoglobin or HSA was infused at a rate of 0.5 m/min until a dose of 2 g/kg was administered. Preliminary experiments had shown that this dose of rHb1.1 elicits a maximal vasoconstrictor response. Arterial pressure, heart rate, and cardiac output data were collected continuously for 90 minutes following completion of the infusion. At the end of the 90 minute data collection period, phenylephrine (3 µg/kg/min, Sigma, St. Louis, Mo.) was infused at a rate of 6 µg/kg/min for 2 minutes to verify proper catheter placement and provide a qualitative indication of the vascular responsiveness of each animal. Animals that did not exhibit a brisk response to phenylephrine were not included in subsequent analysis (<5% occurrence). Each animal received only a single dose of hemoglobin or HSA.

Custom-designed software was used to process the raw hemodynamic data. Mean arterial pressure, heart rate, and mean cardiac output values were determined by averaging data over 30 second intervals every 5 minutes prior to and for 30 minutes following hemoglobin administration. Thereafter, 30 second averages were obtained every 10 minutes until the end of the experiment. All data are shown as mean±s.e.

Both mean arterial pressure and heart rate are expressed as the change from baseline. Baseline values were calculated as the average of the data collected for 30 min prior to hemoglobin or HSA administration. Cardiac output is expressed as % change from baseline. Total peripheral resistance was calculated from mean arterial pressure and cardiac output and is also expressed as the % change from baseline. To facilitate comparisons of the responses to several molecules, the data from 10 to 90 minutes post-administration were averaged for each animal to obtain a "cumulative" response. The baseline and cumulative response data were analyzed by one-way analysis of variance and Newman-Keuls post-hoc tests. For all statistical comparisons, $p < 0.05$ was considered significant.

The mean arterial pressure responses elicited by the polymerized heme pocket variants SGE3011 (glutaraldehyde polymerized) and SGE3959 (BMA-PEG polymerized) were significantly lower than the response elicited by rHb1.1. The responses to these hemoglobins were not significantly different from the response observed following HSA administration. One other polymerized heme variant pocket, SGE3937 (BM-PEG polymerized), also elicited a response that was significantly less than the response obtained in the rHb1.1 group.

Total peripheral resistance responses were similarly altered by changes in the heme pocket structure and by polymerization. All of the hemoglobin variants elicited systemic vasoconstrictor responses that were significantly less than the rHb1.1 response. However, only the response to SGE3959 (BMA-PEG polymerized) was the same as the response obtained with the negative control (HSA). The responses to the other hemoglobin variants were significantly greater than the HSA response. The response to SGE3959 (BMA-PEG polymerized) was also significantly different from the responses obtained with SGE3653 (glutaraldehyde polymerized), SGE3937 (BM-PEG polymerized) and SGE3011. These results indicate that the combination of heme pocket mutations with polymerization and decoration present in the SGE3959 (BMA-PEG polymerized) variant has the greatest effect on the systemic hemodynamic response to a 2 g/kg topload dose, and that these changes essentially eliminated the hemoglobin-induced systemic vasoconstriction.

Figure 9:
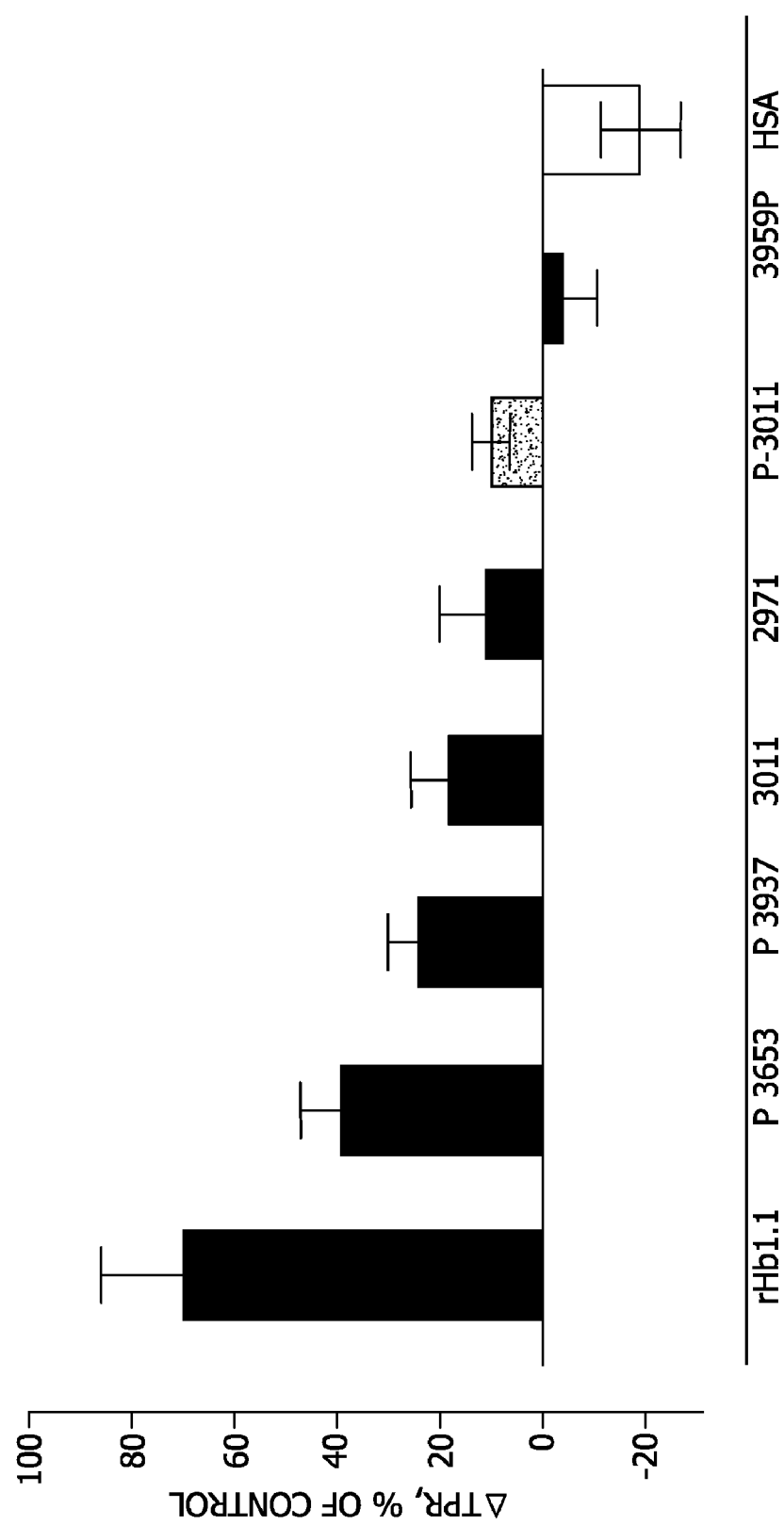
FIG. 9 shows the total peripheral resistance response (TPR) in rats to recombinant hemoglobin compositions and human serum albumin. HSA was administered as a control. Protein doses were 2000 mg/kg for the recombinant hemoglobins and for HSA. The change in TPR is expressed as a percentage of change from baseline. The change in TPR was calculated by dividing the change in MAP from 10 to 90 minutes following administration by the change in mean cardiac output during the same period.

The results are shown in Tables 5 and 6, below, and in FIGS. 8 and 9.

TABLE 5

Mean Arterial Pressure Responses
(2 g/kg topload dose, conscious rats)

| Hemoglobin | Δ MAP, mmHG |
|---|---|
| rHb1.1 | 23.4 ± 5.1 |
| SGE2971 (Genetically fused dimer) | 19.3 ± 3.2 |
| SGE3653 (Glutaraldehyde polymerized) | 17.7 ± 2.3 |
| SGE3011 | 16.0 ± 2.2 |
| SGE3937 (BM-PEG polymerized) | 13.1 ± 2.4 |
| SGE3011 (Glutaraldehyde polymerized) | 4.5 ± 0.6 |
| SGE3959 (BMA-PEG polymerized) | 4.2 ± 1.5 |
| HSA | 0.4 ± 2.2 |

TABLE 6

Total Vascular Resistance Responses
(2 g/kg topload dose, conscious rats)

| Hemoglobin | Δ TPR, % of control |
|---|---|
| rHb1.1 | 72.4 ± 14.2 |
| SGE3653 (Glutaraldehyde-polymerized) | 41.5 ± 6.4 |
| SGE3937 (BM-PEG polymerized) | 26.3 ± 3.7 |
| SGE3011 | 20.2 ± 5.1 |
| SGE2971 (Genetically fused dimer) | 13.2 ± 6.8 |
| SGE3011 (Glutaraldehyde polymerized) | 10.5 ± 3.6 |
| SGE3959 (BMA-PEG polymerized) | −5.2 ± 4.3 |
| HSA | −17.7 ± 7.7 |

Both increasing the average molecular weight and decreasing nitric oxide reactivity independently decrease the pressor effect of extracellular hemoglobin solutions, as has been shown in the data disclosed in WO 98/50430. In the data shown above, the hemoglobins which exhibited a reduced pressor effect (an increase of less than 20 mm Hg over baseline MAP) had either very low nitric oxide kinetics (~2 $\mu M^{-1}s^{-1}$), or intermediate nitric oxide kinetics (<15 $\mu M^{-1}s^{-1}$) and increased molecular size (either dimers or polymers). The hemoglobins which exhibited a low pressor effect (an increase of less than 10 mm Hg over baseline MAP) had both very low nitric oxide kinetics (~2 $\mu M^{-1}s^{-1}$) and were polymerized. It is interesting to note that one hemoglobin which shares these physical characteristics, SGE3937 (BM-PEG polymerized), was not a low pressor effect hemoglobin. Although the combination of mutations which reduce nitric oxide reactivity and polymerization help to produce a low pressor effect hemoglobin, other mutations or alternate chemical modifications may increase a hemoglobin's pressor effect.

EXAMPLE 13

Evaluation of the Endotoxin Effect of Hemoglobin Compositions in Mice

Endotoxins (e.g., lipopolysaccharide or LPS) are biologically active molecules present in Gram-negative bacteria such as *Eschericia coli*. Injection of purified LPS into animals induces a wide variety of physiological activities which can culminate in septic shock and death. The biological effects of endotoxins are caused indirectly through the interaction of endogenous mediators that are formed following interaction of endotoxins with cellular targets.

Inbred BALB/cByJ mice obtained from Jackson Laboratory were used to test for interactions between endotoxins and test hemoglobin compositions. Test hemoglobin compositions comprising rHb1.1, 3343, glutaraldehyde polymerized rHb1.1, 3345, 2821, 3010, 2971, 2822, 3959, BMA-PEG polymerized 3959, 3011, glutaraldehyde polymerized 3653, BM-PEG polymerized 3937, and glutaraldehyde polymerized 3011 were administered to BALB/cByJ mice at a dose of 1 g/kg intravenously via a tail vein. A stock solution of LPS (Sigma 055-B5) was made in phosphate buffered saline. LPS was administered intraperitoneally at a dose of 5 mg/kg immediately after dosing with the test hemoglobin composition or HSA. Mice were observed for mortality up to 48 hrs. The results are illustrated in FIG. 10.

EXAMPLE 14

Treatment of Head Injury

The effects of hemodilution on intracranial pressure, cerebral perfusion pressure, and fluid requirement can be demonstrated in a porcine model of head injury by comparing resuscitation with various reduced side effect hemoglobin solutions.

Swine (approximately 40 kg) are placed under anesthesia and instrumentation to measure mean arterial pressure (MAP), hemoglobin concentration (Hb), intracranial pressure (ICP), cerebral perfusion pressure (CPP), cerebral blood flow (CBF; $H_2$ clearance), and total fluid requirements. Cerebral oxygen delivery ($cO_2$del) is calculated (CBF×arterial oxygen content). Animals receive a focal cryogenic brain injury to simulate a head injury from an external force. After focal cryogenic brain injury, the animals are hemorrhaged to a MAP of 50 torr. They are then randomized to receive a bolus of either 4 cc/kg of Ringer's Lactate (n=6), or a 10% solution of each reduced side effect hemoglobin tested, to maintain MAP. The group receiving Ringer's Lactate also receives blood (which is recovered from the animals during hemorrhage ("shed blood")) one hour after hemorrhage in the form of packed red blood cells. The group receiving a hemoglobin solution of the invention will receive shed blood only if the hemoglobin concentration measured as described above drops below five g/dl. Variables are measured at baseline (BL), five minutes following the creation of the cryogenic brain injury, within an hour after the beginning of hemorrhage, and at intervals following resuscitation.

Applicants expect that each of the groups receiving a hemoglobin of the invention would have a greater CPP and lower ICP following resuscitation. The volume of fluid required to maintain hemodynamic stability 24 hours after injury would be significantly lower in the groups receiving a hemoglobin of the invention than in the group receiving Ringer's Lactate. No statistically significant difference in regional CBF in the lesioned hemisphere would be observed between the groups. Despite a significantly lower Hb concentration in the group receiving a hemoglobin of the invention, cerebral oxygen delivery would not be significantly different from that in the group receiving Ringer's Lactate at any time.

The increased CPP, lower ICP, and lower fluid requirement which is expected to be observed in the group receiving a hemoglobin of the invention would demonstrate that hemodilution with such a hemoglobin preparation can be beneficial in the early management of head injury in mammals.

EXAMPLE 15

Treatment of Hypovolemia

Male Sprague-Dawley rats (350 g) were anesthetized with urethane. Indwelling arterial and venous catheters were placed for continuous monitoring of mean arterial pressure (MAP), heart rate (HR) and withdrawal of blood for production of hypovolemia, blood sampling for blood chemistries and metabolic indices (base deficit). Animals were bled ~10 mL of blood (rate 1 mL/min), and maintained at this state for 90 min to produce an MAP of 35–40 mmHg and a base deficit of −12 mmol/L. Each rat was assigned to one of four treatment groups (n=6 animals per group) that were resuscitated with 100% volume replacement with solutions of:

| | |
|---|---|
| I. | rHb 1.1 |
| II. | rHb 3011 |
| II. | DCLHb |
| IV. | Human Serum Albumin (HSA) |

All solutions were infused at a rate of 1.0 mL/min. All hemoglobin solutions were prepared as in Examples 6 and 7.

Following hemorrhage, the MAP was reduced from a baseline of 100 mmHg to 45 mmHg, but by 30 and 60 min post-resuscitation, MAP rose above baseline to ~125 mmHg in all treatment groups except for HSA rats which remained hypotensive (~75 mmHg).

Following hemorrhage, the HR was decreased from a baseline of 375–390 bpm to 330–350 bpm. Heart rate remained variable in all treatment groups throughout 30 and 60 min post-resuscitation, but all groups remained below the baseline level.

Following hemorrhage, base deficit was reduced from a baseline of −2 mmol/L to −12 mmol/L but by 60 min of resuscitation all treatment groups had partially recovered to −6 to −8 mmol/L.

In summary, a 10% hemoglobin solution of the invention (rHb3011) restored MAP and re-elevated base deficit toward normal in a rat model of hemorrhage and resuscitation. Heart rate did not recover to baseline levels, but remained well within range to support survival.

EXAMPLE 16

Complete Isovolemic Exchange Transfusion Study

This example demonstrates the ability of RL mutant hemoglobins to deliver oxygen in the absence of red blood cells. Anesthetized, male Sprague-Dawley rats were acutely catheterized for hemoglobin infusion, blood withdrawal, arterial pressure measurement, and maintenance of anesthesia and sealed in a respirometer for continuous measurement of oxygen consumption. Hemodynamic parameters and body temperature were monitored continuously throughout the experiment. Periodic arterial and venous blood samples were taken for measurement of blood gases, oxygen content, hemoglobin concentration, and hematocrit. After stabilization and recording of baseline values, complete isovolemic exchange transfusion was carried out (3 ml/min/kg) with hemoglobin variants (8 g/dl) or oncotically matched human serum albumin (HSA) until hematocrit fell from starting levels of approximately 45% to below a nominal value of 2% (approximately 55 min). All hemoglobin solutions were adjusted with HSA to have the same colloid oncotic pressure. Measurements continued for up to 60 minutes following cessation of exchange. At the end of exchange with hemoglobin variants, circulating levels of recombinant hemoglobin were approximately 7–7.5 g/dl. In the animals that received HSA, oxygen consumption declined rapidly as hematocrit declined below 20% and none of the animals survived to the end of exchange. As expected, arterial base excess and the arteriovenous oxygen content difference also declined markedly. Oxygen extraction rose initially before declining as the hemoglobin concentrations fell to low levels (<3 g/dl). In contrast, exchange with hemoglobin variants maintained oxygen consumption at near-control levels. Oxygen extraction increased to compensate for the low circulating hemoglobin concentrations and allowed the arteriovenous oxygen content difference to remain at basal levels. All animals that received RL hemoglobin survived to the nominal end of the experiment (60 minutes post-exchange). These results demonstrate that the RL mutants effectively transport and deliver oxygen and that the kinetics of NO scavenging can be significantly altered without impacting oxygen delivery under basal metabolic conditions.

EXAMPLE 17

The Effect on Infarct Volume Following Focal Cerebral Ischemia in Rats Treated with Reduced Side Effect Hemoglobin Hemoglobin is known to bind nitric oxide, which is implicated as neurotoxic or neuroprotective during cerebral ischemia (Am J Physiol 267:H276–H284, 1994). The effect on cerebral ischemic injury in rats was assessed for four different recombinant hemoglobin compositions.

After approval by the Animal Care Committee, rats were anesthetized with isoflurane. Physiologic parameters were controlled, and before ischemia, rats received one of the following:
1. Control (n=8)—no hematocrit manipulation
2. rHb1.1 (n=6)—hematocrit decreased to 30% with a 10% solution of recombinant rHb1.1 ($k'_{NO\ OX}$=58 $\mu M^{-1} s^{-1}$)
3. SGE3011 (n=7)—hematocrit decreased to 30% with a recombinant 10% monomeric hemoglobin solution having reduced NO reactivity ($k'_{NO\ OX}$=2.5 $\mu M^{-1} s^{-1}$)
4. Glutaraldehyde polymerized rHb1.1 (n=8)—hematocrit decreased to 30% with a 10% solution of glutaraldehyde crosslinked recombinant rHb1.1 ($k'_{NO\ OX}$=58 $\mu M^{-1} s^{-1}$)
5. Polymerized SGE3011 (n=7)—hematocrit decreased to 30% with a 10% recombinant-polymerized hemoglobin solution having reduced NO reactivity ($k'_{NO\ OX}$=2.5 $\mu M^{-1} s^{-1}$)

Via a craniectomy, the middle cerebral artery was occluded for 180 minutes, 120 minutes of reperfusion was allowed, and infarct volume assessed with TTC stain. Infarct volume (mm$^3$, mean±SD) was 194±31 in the Control group, 193±34 in the rHb1.1 group, and 175±44 in the GLX-rHb1.1 group; and was significantly less (142±28) for the rHb3011 group than the Control and rHb1.1 groups; and was significantly less (110±39) in the Poly-rHb3011 group than the Control, rHb1.1, and GLX-rHb1.1 groups.

EXAMPLE 18

Enhancement of Radiation Therapy

The ability of reduced side effect hemoglobin compositions solutions to enhance the effectiveness of radiation therapy may be demonstrated in rats. The reduced side effect hemoglobin compositions are about 10 g/dl hemoglobin.

Sprague-Dawley rats (weighing approximately 200–250 g) are injected with 0.1 ml solution containing approximately 1×10$^7$ osteogenic sarcoma cells in the right hindquarter. The tumors are allowed to grow to about 1.5 cm$^3$ in volume. The rats are divided into several groups (n=about 10 animals per group):
I. Given 10 ml/kg Ringer's lactate without any radiation
II. Given 10 ml/kg of Ringer's lactate and a single 4 Gy gamma radiation dose
III, etc. Given 10 ml/kg of each reduced side effect hemoglobin in solution and a single 4 Gy gamma radiation dose On the day of the experiments, the animals are anesthetized with an initial dose of 1.2 ml/kg of a 3:7 mixture of xylazine (20 mg/ml) and ketamine (100 mg/ml) and thereafter given 0.6 ml of the same anesthesia solution to maintain anesthesia. The animals are placed on heating pads and their body temperature maintained at 38–39 degrees.

All solutions are administered via the tail vein. The radiation is administered two hours later. The osteosarcoma is measured prior to the radiation, after one, two, three, and finally, after four weeks. Osteosarcomas larger than 1.5 cm$^3$ are hypoxic, with surface tissue oxygen tensions from 0–5 torr, as determined by the OxySpot/OxyMap apparatus. Applicants expect that in groups receiving the reduced side effect hemoglobin solutions, greatly reduced sarcoma would be found four weeks after the administration of reduced side effect hemoglobin in combination with the radiation, as compared to the Ringer's control groups, which would show continued tumor growth.

EXAMPLE 19

Enhancement of Chemotherapy

The ability of reduced side effect hemoglobin compositions to enhance the effectiveness of chemotherapy may be demonstrated in rats. The chemotherapeutic agent used in this example is cyclophosphamide (CTX). The reduced side effect hemoglobin composition is about 10% wt/volume hemoglobin.

Sprague-Dawley rats (weighing approximately 200–250 g) are injected with 0.1 ml solution containing approximately $2 \times 10^6$ FsaII fibrosarcoma cells in the right hindquarter. The tumors are allowed to grow to about 1.5 cm$^3$ in volume. The rats are divided into several groups (n=about 10 animals per group):
  I. Given 10 ml/kg Ringer's lactate without any chemotherapeutic
  II. Given 10 ml/kg of Ringer's lactate and 100 mg/kg CTX
  III., etc Given 10 ml/kg of each reduced side effect hemoglobin in solution and 100 mg/kg CTX On the day of the experiments, the animals are anesthetized with an initial dose of 1.2 ml/kg of a 3:7 mixture of xylazine (20 mg/ml) and ketamine (100 mg/ml) and thereafter given 0.6 ml of the same anesthesia solution to maintain anesthesia. The animals are placed on heating pads and their body temperature maintained at 38–39 degrees. Hemoglobin solutions are administered via the tail vein, and the CTX solution is administered by intraperitoneal injection immediately after the hemoglobin solution is administered. The animals are sacrificed 24 hours after treatment to allow for full expression of drug cytotoxicity and repair of potentially lethal damage. The tumors are excised under sterile conditions and single cell suspensions are prepared for a colony forming assay. One week later the plates are stained with crystal violet and colonies of more than 50 cells are counted.

Bone marrow toxicity is determined as follows: bone marrow is taken from the same animals used for the tumor excision assays and colony forming assays are carried out in the same manner. Colonies of at least 50 cells are scored on an acculite colony counter.

Applicants expect that CTX would be observed to kill fibrosarcoma cells. However, co-treatment with reduced side effect hemoglobin compositions would result in a significant increase in fibrosarcoma cell death and toxicity of CTX to bone marrow cells.

EXAMPLE 20

Preparation of tetrakis-(3-maleimidopropyl)pentaerythritol Cross-linked Reduced Side Effect Hemoglobin A 4-arm crosslinker, a tetramaleimide derivatized pentaerythritol (see below), was purchased from Molecular BioSciences, Inc. (catalog number 19847) located in Boulder, Colo. The hemoglobin chosen for this crosslinking experiment, 3927, contained a single surface cysteine at position 158 in the dialpha chain (position 16 in the second alpha domain, in the A helix) with the cysteines at position 93 in the beta subunits mutated to alanine to remove any side reactions. This hemoglobin also contained the heme pocket mutations found in rHb3011, along with initiator methionines, the glycine linker between alpha subunits, and the beta T87Q mutation.

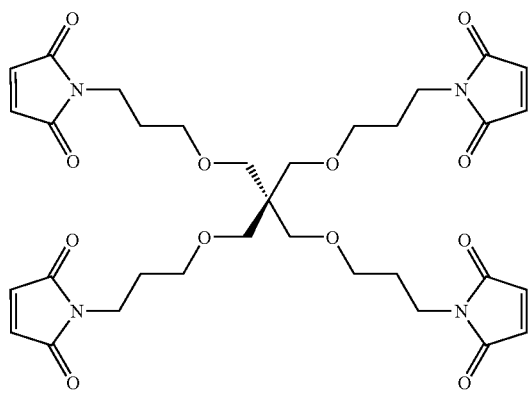

The oxy form of 3927 was run through a Sephadex G25 (Pharmacia PD-10) column equilibrated with 50 mM HEPES pH7.5, then concentrated to 90 g/L ($\epsilon$=0.8372 L g$^{-1}$ cm$^{-1}$ at 540 nm). 150 µL 90 g/L rHb3927 (0.210 µmol) was transferred into a 13×100 mm test tube on ice, and 7.23 µL 5/gL tetramaleimide pentaerythritol in DMSO (0.052 µmol) was added at once with shaking. The test tube was sealed and carbon monoxide was blown over the reaction mixture. The reaction was allowed to stand on ice, and 5 µL aliquots were taken at various timepoints for sizing via HPLC.

The 3927 starting material was a single species, as verified by size exclusion chromatography (SEC). At three hours, the reaction consumed almost two-thirds of the starting material. At 21 hours, SEC gave four peaks, assigned as tetraHb, triHb, diHb, and monoHb (6.4%, 63.9%, 5.8% and 23.9% respectively) with no higher molecular weight moieties. At 22 hours, another 1.71 µL 5 g/L tetramaleimide pentaerythritol in DMSO (0.012 µmol) was added to the reaction in an attempt to decrease the amount of starting material left over. The reaction was allowed to stand on ice over the weekend. The final SEC trace (FIG. 13) gave the same four peaks in a different ratio (9.2% tetraHb, 74.4% triHb, 10.0% diHb, and only 6.4% monoHb).

The reaction of four equivalents of single surface cysteine hemoglobin with one equivalent tetramaleimide pentaerythritol produced a discrete distribution of polymeric hemeoglobin. This discrete polymer was predominately the size of three hemoglobins, with a small amount of the four hemoglobin sized species, possibly due to steric hindrance. A very small amount of the starting hemoglobin was left over, and no size range larger than four hemoglobins was seen. This polymerization strategy, utilizing a mono-functional hemoglobin and a poly-functional multi-armed linker, could be attempted again with a functional group other than maleimide, and/or with longer arms between the core pentaerythritol and the functional group to achieve a tetramer rather than a trimer of hemoglobins.

EXAMPLE 21

Preparation of Bismaleimidoalanyl Polyethylene Glycol 3700 Cross-linked Reduced Side Effect Hemoglobin—SGE3959

Materials:

Deoxy SGE3959: Approx. 0.3 kg. at $\approx$72 g/L (based on a spectrophotometric determination of Hb concentration) in 40 mM sodium borate buffer, pH 9.1–9.2.

BMA-PEG-3700 stock solution: An approximately 103 g/L solution was prepared in a Class 100 hood by mixing BMA-PEG powder with an appropriate volume of WFI and then filtering through a 0.2 micron membrane. The concentration and volume of PEG reagent prepared was such that after addition to the reactor, the reaction mixture would contain Hb at a concentration of 60 g/L and there would be a 5-fold molar excess of BMA-PEG over Hb.

N-Acetyl-1-cysteine: A half-liter solution of 1 M N-acetyl-1-cysteine (NAC) was prepared by adding 81.6 g NAC powder to deoxygenated 1.2 N NaOH to 0.5 L final volume. The solution was filtered through a 0.2 micron membrane, and maintained in a deoxygenated environment until use.

Deoxy gluconate electrolyte solution: A 100 liter solution of gluconate electrolyte solution was prepared by dissolving 0.68 kg of NaCl, 30 gm of KCl, and 0.52 kg of sodium gluconate in WFI. The solution was deoxygenated by thorough bubbling with nitrogen gas.

Deoxy phosphate buffer: A 5 liter solution of phosphate buffer was prepared by dissolving 62 gm of monobasic sodium dihydrogen phosphate and 308 gm of dibasic disodium monohydrogen phosphate in WFI. The solution was deoxygenated by thorough bubbling with nitrogen gas.

Equipment:

The reaction was performed in a 11 L stainless steel reactor, containing a variable speed mixing agitator, an external heating pad for temperature regulation, and ports for sample withdrawal, reagent addition, as well as atmospheric control.

Ultrafiltration of the post-reaction mixture was performed in a chilled ultrafiltration loop holding 2 m$^2$ of Millipore Biomax 30 polyethersulfone membranes, a lobe-type pump, and a 20 liter reservoir under a nitrogen atmosphere.

Methods:

The reactor was purged of oxygen and placed under a nitrogen atmosphere. An appropriate volume of deoxygenated SGE3959 at the targeted initial concentration (72±5 g/L) was transferred into the reactor under oxygen-free conditions. Once hemoglobin volume and concentration parameters within the reactor were verified, the reactor temperature was set to 25° C., and the agitator was set such that mixing occurred with a minimum of foam/bubble generation. Meanwhile, the BMA-PEG solution was prepared and the volume needed for polymerization was transferred to a small pressure can. The pressure can was attached to the reactor via tubing running through a peristaltic pump. The BMA-PEG solution was degassed by sparging the solution with nitrogen gas until oxygen levels within the can dropped to below 30 ppm.

With the reactor at 25° C., the reaction was initiated by pumping the BMA-PEG solution from the pressure can into the reactor, at a speed such that the required volume was transferred in a 5 minute span.

The reaction was monitored using a Pharmacia Superdex200 HR10/30 size exclusion chromatography (SEC) column. At time zero and every 0.5 hr thereafter, a 0.25 mL sample was obtained from the reactor and diluted 40-fold in cold phosphate buffered solution. 20 μL of the diluted sample was then run on the column, on a Hewlett-Packard HP1090M chromatography workstation. The column buffer was 50 mM sodium phosphate, 150 mM NaCl, pH 7.0. The column was run at 0.7 mL/min, at ambient temperature, for 30 min.

While the reaction proceeded, the additions pressure can was rinsed well with WFI. The appropriate volume of 1 M NAC was transferred to the pressure can. The can was then sparged with nitrogen until deoxygenated as described above.

When the chromatographic monitoring indicated a desired size distribution, the reaction was quenched by bolus addition of NAC to attain a 20-fold molar excess over BMA-PEG. Immediately after NAC addition, the reactor temperature was set to 8° C. The reaction mixture was monitored every 0.5 hr thereafter by a spectrophotometric assay for methemoglobin. The quenching reaction was considered complete when methemoglobin levels were minimized (due to reduction by NAC).

After quenching, the reaction mixture was transferred into an ultrafiltration system under deoxy conditions and kept chilled at about 10° C. Using a Millipore Biomax 30 (30 KDa) polyethersulfone membrane, the reaction mixture, at about 80 gm Hb/liter concentration, was diafiltered for 3 diavolumes with deoxy gluconate electrolyte solution. Then, 0.67 liter of deoxy phosphate buffer was added per liter hemoglobin solution to drive the pH into the physiologic range, about pH 7. Diafiltration for an additional 13 diavolumes with gluconate electrolyte solution removed free BMA-PEG, NAC, phosphate and borate from the original reaction mixture. The concentration of the hemoglobin solution was elevated to 100 g/L by removing permeate through the membrane, and then Tween-80 and NAC were added to levels of 0.075% and 9.2 mM, respectively, resulting in formulated product.

The final formulated product was analyzed for size distribution by Superdex200 SEC. The chromatography was performed as described above, with detection at 414 nm wavelength. HPLC integration parameters were set such that a horizontal baseline was drawn and vertical integration lines were dropped from every valley. The resultant chromatogram (see FIG. 15 for a representative profile) was compared to a chromatogram of SEC standard proteins (Bio-Rad catalog no. 151–1901). The protein standards were run under identical conditions, and with detection at 280 nm wavelength, to gauge the apparent molecular size distribution of the polymeric species.

Since the PEG reaction leads to a complex, heterogeneous mixture and since SEC methods separate molecules on the basis of hydrodynamic radius and not on absolute molecular weight, SGE3959 for Injection has been characterized by the shape of its SEC profile (FIG. 15) and by the integrated areas under its SEC peaks.

The SEC profile is characterized by having two main peaks: one with a retention time (RT) of roughly 17 min, and the other with an RT of approx. 14 min. The vertical integration line from the valley touches the baseline at a point corresponding to a time of roughly 15 min. An integrated chromatographic profile thus typically has two demarcated peak areas. The peak with RT of ≈14 min corresponds to PEG-hemoglobins with apparent molecular weight >158 kDa (the gamma globulin standard, with a molecular weight of 158 kDa, has a peak RT of ≈16 min). The majority of material under this peak are polymeric species with apparent molecular weights of <670 kDa (the thyroglobulin standard, with a molecular weight of 670 kDa, has a peak RT of ≈12 min), although a small percentage is of higher apparent mass. The peak with RT of around 17 min corresponds to PEG-hemoglobins with MW >65 kDa (monomer Hb has a peak RT of ≈21 min). Typically, the peak area to the left of the vertical integration line represents ≈40–50% of the total area, while the area to the right of the line accounts for the other 50–60% of the total. Size exclusion chromatography in-line with mass spectroscopy (SEC-MS) has revealed that roughly half of the molecules (the majority of which fall under the peak to the right of the 15 min. line) are PEG-decorated . and/or internally crosslinked monomers. By this analysis, the remaining molecules are dimers, trimers, and higher order multimers, all with various combinations of PEG-decorations as well as intra- and inter-molecular PEG cross-links. The average ratio of moles PEG per mole hemoglobin over the spectrum of species is 3, with a range from about 2 to up to about 11 for heavily-decorated species.

EXAMPLE 22

Preparation of Bismaleimidoalanyl Polyethylene Glycol 3700 Cross-linked Reduced Side Effect Hemoglobin—SGE3487

Materials:

Deoxy SGE3487: Approx. 1 kg. at ≈78 g/L (based on a spectrophotometric determination of Hb concentration) in 40 mM sodium borate buffer, pH 9.1–9.2.

BMA-PEG-3700 stock solution: An approximately 111 g/L solution was prepared in a Class 100 hood by mixing BMA-PEG powder with an appropriate volume of WFI and then filtering through a 0.2 micron membrane. The concentration and volume of the prepared PEG solution was such that after addition to the reactor, the reaction mixture would contain hemoglobin at a concentration of 65 g/L and there would be a 5-fold molar excess of BMA-PEG over hemoglobin.

N-Acetyl-1-cysteine: A 2-liter solution of 1 M N-acetyl-1-cysteine (NAC) was prepared by adding 326.4 g NAC powder to deoxygenated 1.2 N NaOH to 2.0 L final volume. The solution was filtered through a 0.2 micron membrane, and maintained in a deoxygenated environment until use.

Deoxy gluconate electrolyte solution: A 300 liter solution of gluconate electrolyte solution was prepared by dissolving 2.05 kg of NaCl, 90 gm of KCl, and 1.57 kg of sodium gluconate in WFI. The solution was deoxygenated by thorough bubbling with nitrogen gas.

Deoxy phosphate buffer: A 5 liter solution of phosphate buffer was prepared by dissolving 62 gm of monobasic sodium dihydrogen phosphate and 308 gm of dibasic disodium monohydrogen phosphate in WFI. The solution was deoxygenated by thorough bubbling with nitrogen gas.

Equipment:

The reaction was performed in a 22 L stainless steel reactor, containing a variable speed mixing agitator, an external heating pad for temperature regulation, and ports for sample withdrawal, reagent addition, as well as atmospheric control.

Ultrafiltration of the post-reaction mixture was performed in a chilled ultrafiltration loop holding 3 m$^2$ of Millipore PLCHK membranes, a lobe-type pump, and a 20 liter reservoir under a nitrogen atmosphere.

Methods:

The reactor was purged of oxygen and placed under a nitrogen atmosphere. An appropriate volume of deoxygenated SGE3487 at the targeted initial concentration (78±6 g/L) was transferred into the reactor under oxygen-free conditions. Once hemoglobin volume and concentration parameters within the reactor were verified, the reactor temperature was set to 25° C., and the agitator was set such that mixing occurred with a minimum of foam/bubble generation. Meanwhile, the BMA-PEG solution was prepared and the volume needed for polymerization was transferred to a small pressure can. The pressure can was attached to the reactor via tubing running through a peristaltic pump. The BMA-PEG solution was degassed by sparging the solution with nitrogen gas until oxygen levels within the can dropped to below 30 ppm.

With the reactor at 25° C., the reaction was initiated by pumping the BMA-PEG solution from the pressure can into the reactor, at a speed such that the required volume was transferred in a 5 minute span.

The reaction was monitored using a Pharmacia Superdex200 HR10/30 size exclusion chromatography (SEC) column. At time zero and every 0.5 hr thereafter, a 0.25 mL sample was obtained from the reactor and diluted 40-fold in cold phosphate buffered saline. 20 μL of the diluted sample was then run on the column, on a Hewlett-Packard HP1100 chromatography workstation. The column buffer was 50 mM sodium phosphate, 150 mM NaCl, pH 7.0. The column was run at 0.7 mL/min, at ambient temperature, for 30 min.

While the reaction proceeded, the additions pressure can was rinsed well with WFI. The appropriate volume of 1 M NAC was transferred to the pressure can. The can was then sparged with nitrogen until deoxygenated as described above.

The PEG reaction was allowed to proceed for 3.5 hr, after which the reaction was quenched by bolus addition of NAC to attain a 20-fold molar excess over BMA-PEG. The reaction mixture was monitored every 0.5 hr thereafter by a spectrophotometric assay for methemoglobin. The quenching reaction was considered complete when methemoglobin levels were minimized (due to reduction by NAC).

After quenching, the reaction mixture was transferred into an ultrafiltration system under deoxy conditions and chilled to about 10° C. Using a Millipore PLCHK (100 KDa) regenerated cellulose membrane, the reaction mixture, at about 50 gm Hb/liter concentration, was diafiltered for 3 diavolumes with deoxy gluconate electrolyte solution. Then, 0.1 liter of deoxy phosphate buffer was added per liter hemoglobin solution to drive the pH into the physiologic range, about pH 7. Diafiltration for an additional 10 diavolumes with gluconate electrolyte solution removed free BMA-PEG, NAC, phosphate and borate from the original reaction mixture. The concentration of the hemoglobin solution was elevated to 100 g/l by removing permeate through the membrane, and then NAC was added to a final 9.2 mM concentration, resulting in formulated product.

The formulated product (SGE3487 for Injection) was analyzed for size distribution by Superdex200 SEC. The chromatography was performed as described above, with detection at 414 nm wavelength. HPLC integration parameters were set such that a horizontal baseline was drawn and vertical integration lines were dropped from every valley. The resultant chromatogram (see FIG. 16 for a representative profile) was compared to a chromatogram of SEC standard proteins (Bio-Rad catalog no. 151–1901). The protein standards were run under identical conditions, and with detection at 280 nm wavelength, to gauge the apparent molecular size distribution of the polymeric species.

Since the PEG reaction leads to a complex, heterogeneous mixture and since SEC methods separate molecules on the basis of hydrodynamic radius and not on absolute molecular weight, SGE3487 for Injection has been characterized by the shape of its SEC profile (FIG. 16) and by the integrated areas under its SEC peaks.

The SEC profile can be characterized by having two main peaks: one with a retention time (RT) of roughly 17 min, and the other with an RT of approx. 14 min. In most instances a third peak, with an RT of about 10.5 min, is also defined. The vertical integration lines from the valleys touch the baseline at points corresponding to times of roughly 11 and 15 min. An integrated chromatographic profile thus typically has two or three demarcated peak areas. The peak with RT of 10.5 min corresponds to PEG-modified hemoglobins with apparent molecular weight >670 kDa (the thyroglobulin standard, with a molecular weight of 670 kDa, has a peak RT of ≈12 min). The peak with RT of ~14 min corresponds to PEG-hemoglobins with apparent molecular weight >158 kDa (the gamma globulin standard has a peak RT of ≈16 min), and the peak with RT of around 17 min corresponds to PEG-hemoglobins with MW >65 kDa (monomer hemoglobin has a peak RT of ≈21 min). Typically, the peak area to the left of the 15 min. vertical integration line represents ≈50% of the total area, while the area to the right of the line accounts for the other half of the total. Size exclusion chromatography in-line with mass spectroscopy (SEC-MS) has revealed that roughly half of the molecules (the majority of which fall under the peak to the right of the 17 min. line) are PEG-decorated and/or internally crosslinked monomers. By this analysis, the remaining molecules are dimers, trimers, and higher order multimers, all with various combinations of PEG-decorations as well as intra- and inter-molecular PEG cross-links. The average ratio of moles PEG per mole hemoglobin over the spectrum of species is 3, with a range from about 2 to up to about 11 for heavily-decorated species.

EXAMPLE 23

Rat Pancreatic Enzyme Model

Sprague-Dawley male rats weighing approximately 250 to 300 grams were administered various hemoglobin solutions through the tail vein as a top load at a dose of up to 6 ml (100 mg/kg to 2 g/kg) in order to determine the influence of the Providence mutation (βK82D) on serum lipase and serum amylase levels. The rats were administered recombinant hemoglobin 1.1, recombinant hemoglobin 3345, recombinant hemoglobin 3011, or recombinant hemoglobin 3010. Recombinant hemoglobin 1.1 and 3345 are identical in protein sequence other than 3345 contains the Providence mutation. Equally, recombinant hemoglobin 3011 and 3010 are identical in protein sequence other than 3010 contains the Providence mutation. Serum samples were obtained from the rats pre-infusion and at 1, 2, 4, 8, and 24 hours after the administration of the recombinant hemoglobin. Serum amylase and lipase levels were determined using standard clinical assays generally known to those skilled in the field.

Figure 17A:
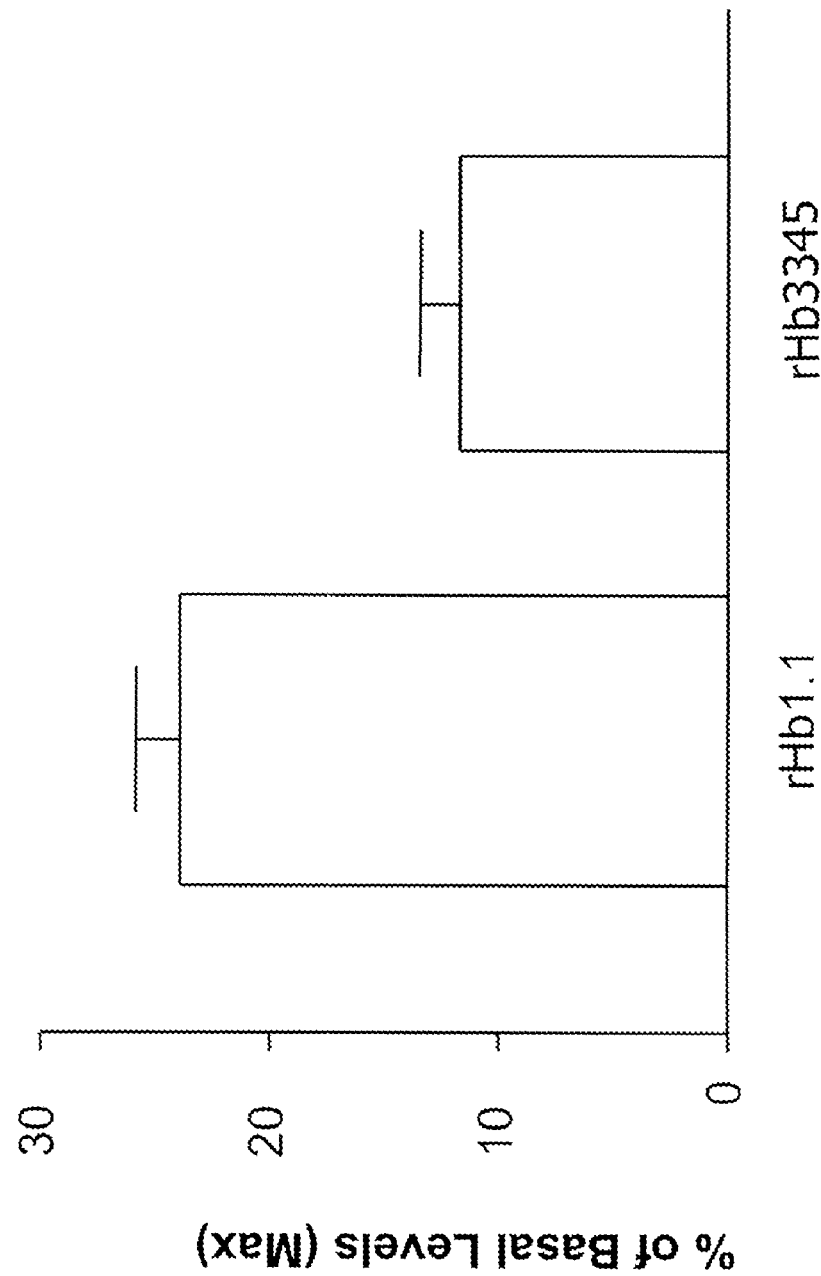
FIGS. 17(a) and 17(b) are graphs depicting the effect of the Providence mutation on serum lipase levels.
Figure 17B:
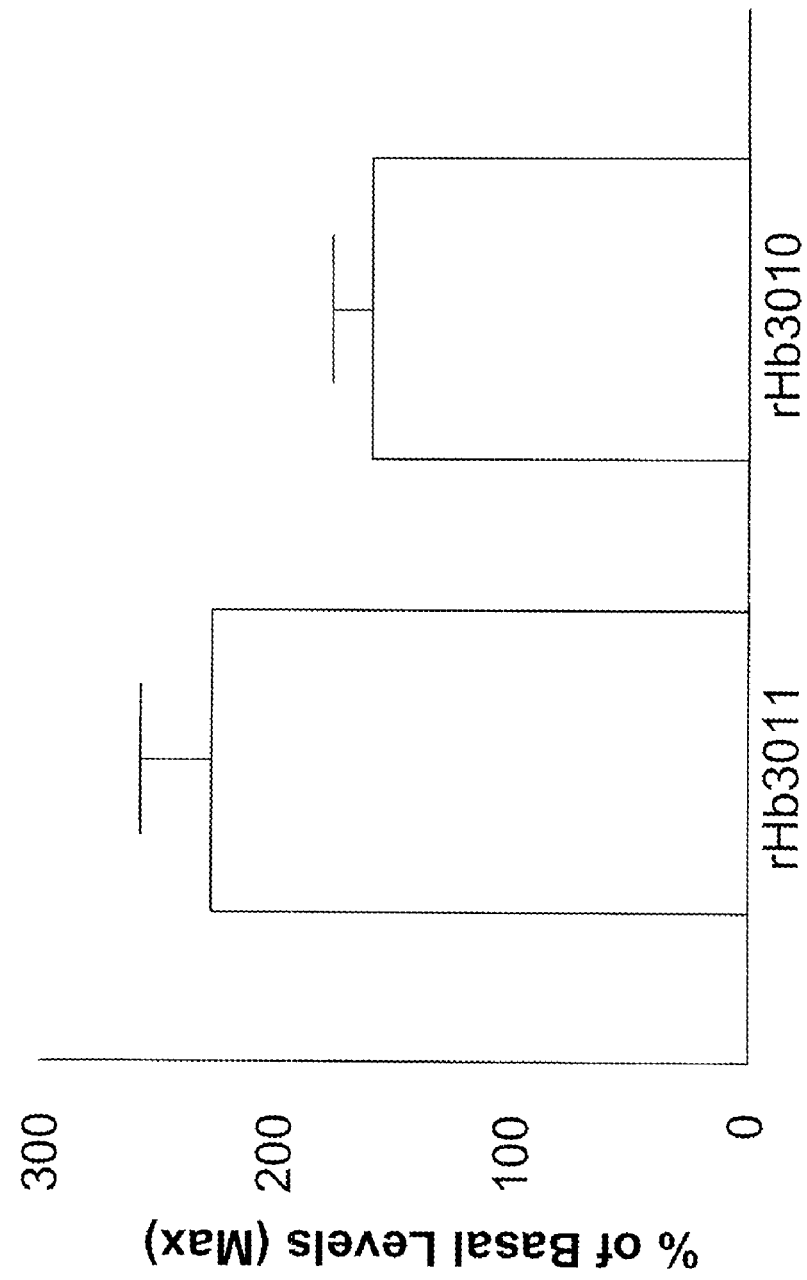

FIGS. 17(a) and 17(b) depict the effect of the Providence mutation on serum lipase levels. Serum lipase levels are lower over the 24 hour observation period if the recombinant hemoglobin administered contains the Providence mutation. The Providence mutation did not effect the levels of serum amylase.

The invention being thus described, it will be obvious that the same can be modified in various ways. Such variations are not to be regarded as a departure from the spirit and scope of the present invention, and all such modifications and equivalents as would be obvious to one skilled in the art are intended to be included within the scope of the following claims.

What is claimed is:

1. A pharmaceutical composition for transporting and releasing oxygen comprising a suspension of from about 5 to about 20 grams of reduced lesion hemoglobin per deciliter of a pharmaceutically acceptable carrier, wherein the hemoglobin is polymerized.

2. The pharmaceutical composition of claim 1 wherein the hemoglobin is reduced gastrointestinal effect hemoglobin, low gastrointestinal effect hemoglobin, low pressor effect hemoglobin, or hemoglobin which exhibits decreased aggregate formation when stored in solution in deoxygenated form for prolonged periods.

3. The pharmaceutical composition of claim 1 wherein the composition: a) is substantially free of red blood cell stroma, b) is substantially free of pyrogens, and c) comprises less than about 10% methemoglobin.

4. The pharmaceutical composition of claim 1 wherein the hemoglobin has an average molecular weight between 65 and 650 kilodaltons.

5. The pharmaceutical composition of claim 1 wherein the hemoglobin is further characterized in that the hemoglobin comprises at least one heme pocket mutation which reduces the rate of NO scavenging when compared to the same molecule without the heme pocket mutation.

6. The pharmaceutical composition of claim 1 wherein the reduced lesion hemoglobin is an oligomeric hemoglobin with a molecular weight distribution of greater than about 50% in the range of 130 to 500 kilodaltons, wherein at least 80% of the oligomeric hemoglobin comprises two or more hemoglobin-like proteins.

7. The pharmaceutical composition of claim 1 wherein the reduced lesion hemoglobin includes about 40 to about 60% derivatized monomeric hemoglobin with an average molecular weight between 65 and less than about 130 kilodaltons, and about 40 to about 60% oligomeric hemoglobin with an average molecular weight between 130 and 650 kilodaltons, wherein the oligomeric hemoglobin comprises two or more hemoglobin-like proteins.

8. A pharmaceutical composition for transporting and releasing oxygen comprising a suspension of from about 5 to about 20 grams of lesion free hemoglobin per deciliter of a pharmaceutically acceptable carrier, wherein the hemoglobin is polymerized.

9. A pharmaceutical composition for transporting and releasing oxygen comprising a suspension of from about 5 to about 20 grams of reduced gastrointestinal effect hemoglobin per deciliter of a pharmaceutically acceptable carrier, wherein the hemoglobin is polymerized.

10. The pharmaceutical composition of claim 9 wherein the hemoglobin is lesion free hemoglobin or reduced lesion hemoglobin.

11. A pharmaceutical composition for transporting and releasing oxygen comprising a suspension of from about 5 to about 20 grams of low gastrointestinal effect hemoglobin per deciliter of a pharmaceutically acceptable carrier, wherein the hemoglobi is polymerized.

12. The pharmaceutical composition of claim 11 wherein the hemoglobin is lesion free hemoglobin or reduced lesion hemoglobin.

13. A pharmaceutical composition for transporting and releasing oxygen comprising a suspension of from about 5 to about 20 grams of reduced pressor effect hemoglobin per deciliter of a pharmaceutically acceptable carrier, wherein the hemoglobin is polymerized and is reduced lesion hemoglobin, low gastrointestinal effect hemoglobin, reduced gastrointestinal effect hemoglobin, lesion free hemoglobin, or hemoglobin which exhibits decreased aggregate formation when stored in solution in deoxygenated form for prolonged periods.

14. A pharmaceutical composition for transporting and releasing oxygen comprising a suspension of from about 5 to about 20 grams of low pressor effect hemoglobin per deciliter of a pharmaceutically acceptable carrier, wherein the hemoglobin is polymerized.

15. The pharmaceutical composition of claim 14 wherein the hemoglobin is reduced lesion hemoglobin or lesion free hemoglobin.

16. A polymerized recombinant hemoglobin which is a reduced lesion hemoglobin.

17. The hemoglobin of claim 16 wherein the hemoglobin exhibits decreased aggregate formation when stored in solution in deoxygenated form for prolonged periods.

18. The hemoglobin of claim 16 wherein the hemoglobin is further characterized in that the hemoglobin comprises at least one heme pocket mutation which reduces the rate of NO scavenging when compared to the same molecule without the heme pocket mutation.

19. A polymerized recombinant hemoglobin which is a lesion free hemoglobin.

20. A polymerized recombinant hemoglobin which is a reduced gastrointestinal effect hemoglobin.

21. The hemoglobin of claim 20 wherein the hemoglobin is lesion free hemoglobin or reduced lesion hemoglobin.

22. A polymerized recombinant hemoglobin which is a low gastrointestinal effect hemoglobin.

23. The hemoglobin of claim 22 wherein the hemoglobin is lesion free hemoglobin or reduced lesion hemoglobin.

24. A polymerized recombinant hemoglobin which is a reduced pressor effect hemoglobin, and which is reduced lesion hemoglobin, lesion free hemoglobin low gastrointestinal effect hemoglobin, reduced gastrointestinal effect hemoglobin, or hemoglobin which exhibits decreased aggregate formation when stored in solution in deoxygenated form for prolonged periods.

25. A polymerized recombinant hemoglobin which is a low pressor effect hemoglobin.

26. The hemoglobin of claim 25 wherein the hemoglobin is lesion free hemoglobin or reduced lesion hemoglobin.

27. A polymerized recombinant hemoglobin which is a reduced endotoxin effect hemoglobin, and which is a lesion free hemoglobin or a reduced lesion hemoglobin.

28. A polymerized recombinant mutant hemoglobin which exhibits decreased aggregate formation when stored in solution in deoxygenated form for prolonged periods, with the proviso that said hemoglobin does not include the mutation β6 Glu→Val.

29. A chemically crosslinked polymerized hemoglobin which comprises at least one heme pocket mutation which reduces the rate of NO scavenging by the polymerized hemoglobin when compared to the same molecule without the heme pocket mutation.

30. The polymerized hemoglobin of claim 29 wherein the hemoglobin is reduced lesion hemoglobin, lesion free hemoglobin, or reduced pressor effect hemoglobin.

31. A pharmaceutical composition for transporting and releasing oxygen comprising a suspension of from about 5 to about 20 grams of reduced endotoxin effect hemoglobin per deciliter of a pharmaceutically acceptable carrier, wherein the hemoglobin is polymerized and is reduced lesion hemoglobin or lesion free hemoglobin.

* * * * *